US012612547B2

(12) United States Patent
Khalil et al.

(10) Patent No.: US 12,612,547 B2
(45) Date of Patent: Apr. 28, 2026

(54) SEMICONDUCTING NANOPARTICLE

(71) Applicant: SAMSUNG ELECTRONICS CO., LTD., Suwon-si (KR)

(72) Inventors: Sanaa Khalil, Jerusalem (IL); Kobi Yaacov Netanel Oded, Jerusalem (IL)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 972 days.

(21) Appl. No.: 17/642,379

(22) PCT Filed: Sep. 10, 2020

(86) PCT No.: PCT/EP2020/075263
§ 371 (c)(1),
(2) Date: Mar. 11, 2022

(87) PCT Pub. No.: WO2021/048244
PCT Pub. Date: Mar. 18, 2021

(65) Prior Publication Data

US 2022/0340810 A1 Oct. 27, 2022

(30) Foreign Application Priority Data

Sep. 13, 2019 (EP) .................................... 19197372

(51) Int. Cl.

| | |
|---|---|
| ***C09K 11/02*** | (2006.01) |
| ***B82Y 20/00*** | (2011.01) |
| ***B82Y 40/00*** | (2011.01) |
| ***C07C 323/52*** | (2006.01) |
| ***H10K 50/00*** | (2023.01) |
| ***H10K 71/00*** | (2023.01) |

(52) U.S. Cl.
CPC .......... *C09K 11/025* (2013.01); *C07C 323/52* (2013.01); *B82Y 20/00* (2013.01); *B82Y 40/00* (2013.01); *H10K 50/00* (2023.02); *H10K 71/00* (2023.02)

(58) Field of Classification Search
CPC ...... C09K 11/02; C09K 11/025; C07C 323/52
See application file for complete search history.

(56) References Cited

U.S. PATENT DOCUMENTS

| | | | | |
|---|---|---|---|---|
| 10,767,107 B2 | 9/2020 | Shin et al. | |
| 11,661,548 B2 * | 5/2023 | Khalil .................... | C09K 11/08 252/301.36 |
| 2009/0073349 A1 * | 3/2009 | Park ....................... | B82Y 40/00 430/311 |
| 2015/0344776 A1 | 12/2015 | Bootman | |
| 2018/0079953 A1 | 3/2018 | Shin et al. | |
| 2021/0363418 A1 | 11/2021 | Khalil et al. | |

FOREIGN PATENT DOCUMENTS

| | | | | |
|---|---|---|---|---|
| CN | 106032468 A | 10/2016 | |
| CN | 108089401 A | 5/2018 | |
| EP | 3255117 A1 * | 12/2017 | ....... G02F 1/133516 |
| KR | 10-2009-0028928 A | 3/2009 | |
| KR | 10-2018-0057943 A | 5/2018 | |
| WO | 2018056632 A1 | 3/2018 | |
| WO | 2019162242 A1 | 8/2019 | |

OTHER PUBLICATIONS

International Search Report for PCT/EP2020/075263 dated Jan. 12, 2021.
Kim, Hwea Yoon et al. "Heat- and water-proof quantum dot/siloxane composite film: Effect of quantum dot-siloxane linkage," Journal of the SID, 2017, vol. 25, No. 2, pp. 108-116.
Crouse, Christopher A. et al., "Influencing Solvent Miscibility and Aqueous Stability of Aluminum Nanoparticles through Surface Functionalization with Acrylic Monomers," Applied Materials & Interfaces, 2010, vol. 2, No. 9, pp. 2560-2569.
Communication issued on May 27, 2025 by the Japan Patent Office in Japanese Patent Application No. 2022-516014.
Communication dated Oct. 28, 2025, issued by Korean Ministry of Intellectual Property in Korean Patent Application No. 10-2022-7011672.
Communication dated Nov. 18, 2025, issued by Japanese Patent Office in Japanese Patent Application No. 2022-516014.

* cited by examiner

*Primary Examiner* — C Melissa Koslow
(74) *Attorney, Agent, or Firm* — Sughrue Mion, PLLC

(57) ABSTRACT

A semiconducting light emitting nanoparticle includes a core, optionally one or more shell layers, and a compound represented by chemical formula (I)

(I)

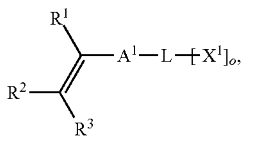

wherein the variables in chemical formula (I) are as described in the specification. A composition includes the aforementioned nanoparticle and at least one further functional material. A formulation includes the aforementioned nanoparticle and at least one solvent. An optical medium and an optical device include the aforementioned nanoparticle.

12 Claims, 2 Drawing Sheets

SEMICONDUCTING NANOPARTICLE

FIELD OF THE INVENTION

The present invention relates to a semiconducting nanoparticle and to a composition and formulation comprising said nanoparticle. Furthermore, the present invention relates to a use of said nanoparticle, to an optical medium and optical device comprising said nanoparticle, and to a process for preparing an optical device.

BACKGROUND ART

The stability of semiconducting light emitting nanoparticles, such as quantum dots (QDs), is essential for their application in electronic devices, optical devices or biomedical devices. Properly stabilized QDs do not significantly lose their photoluminescence intensity when exposed to high temperature, air, moisture and chemicals, which might occur during processing, device fabrication and device operation.

In order to stabilize semiconducting light emitting nanoparticle, in particular QDs, monomeric compounds bearing a functional group that can get chemisorbed on the nanoparticle surface (a so-called "anchor group") and a polymerizable functional group to form a polymerizable monolayer are an interesting class of stabilizer ligands. The advantage of using such bifunctional polymerizable stabilizer ligands is, on the one hand, that the polymerizable monomeric molecules act as a proper stabilizer by binding to the nanoparticle surface and, on the other hand, that they allow for surface polymerization with other suitable monomers, for example with other ligands or molecules from the matrix material, which ensures increased stability of the resulting nanoparticles. That is, the polymerizable functional groups of the surface bound ligands can be polymerized or crosslinked to generate a polymer shell or coating layer which can further enhance the stability of the underlying nanoparticles. Thus, in accordance with the properties of the polymerizable stabilizer ligand used and the polymer shell formed on the nanoparticle surface, the original properties of the nanoparticle core can be greatly altered or modified according to the requirements of application.

Kim et a). ("Heat- and water-proof quantum dot/siloxane composite film: Effect of quantum dot-siloxane linkage", *Journal of the SID,* 25/2, 2017, 108-116) describe CdSe/ZnS quantum dots (QDs) functionalized by oleic acid chemically linked to a siloxane (methacrylate) matrix.

US 2015/0344776 A1 describes nanoparticles having a fist coating layer comprising fatty acid ligands, such as oleic acid, and a second coating layer comprising an organic material having a polar acrylate head group and a non-polar alkyl chain. The second coating layer interacts with the first layer through intercalation of the alkyl chains.

Crouse et al. ("Influencing Solvent Miscibility and Aqueous Stability of Aluminum Nanoparticles through Surface Functionalization with Acrylic Monomers", *ACS Applied Materials in Interfaces*, Vol. 2, No. 9, 2010, 2560-2569) describe aluminium nanoparticles functionalized by 2-carboxyethylacrylate.

WO 2018/056632 A1 describes QDs functionalized with a bifunctional ligand having an anchor group, such as a thiol group, which chemically binds to the surface of the QDs, and a silane functional group that can interact with silane-based materials.

PATENT LITERATURE

1. US 2015/0344776 A1
2. WO 2018/056632 A1

Non-Patent Literature

3. Kim et al. ("Heat- and water-proof quantum dot/siloxane composite film: Effect of quantum dot-siloxane linkage", *Journal of the SID,* 25/2, 2017, 108-116
4. Crouse et al. ("Influencing Solvent Miscibility and Aqueous Stability of Aluminum Nanoparticles through Surface Functionalization with Acrylic Monomers", *ACS Applied Materials in Interfaces*, Vol. 2, No. 9, 2010, 2560-2569

SUMMARY OF THE INVENTION

However, the inventors have newly identified that there is still a need for novel semiconducting light emitting nanoparticles which have improved thermal stability and long-term stability, which have a good solubility, preferably in polar solvents, which can maintain a stable dispersion, in particular in a solution, formulation or film (including after curing), and which can show high quantum yield and luminous efficiency, in particularly when being used in electronic devices, optical devices or biomedical devices.

The present invention was made in view of the problems described above. It is therefore an object of the present invention to provide a semiconducting light emitting nanoparticle which has improved thermal stability and long-term stability, and which shows high quantum yield and luminous efficiency, in particularly when being used electronic devices, optical devices or biomedical devices.

A further object of the present invention is to provide a semiconducting light emitting nanoparticle which has high chemical compatibility with various polymeric systems commonly used in the manufacturing of electronic, optical or biomedical devices, such as (meth)acrylate- or epoxy-based systems, and which has a high solubility in solvents, in particular polar solvents, such as PGMEA, which are commonly used in photolithography.

A further object of the present invention is to provide a semiconducting light emitting nanoparticle which can maintain a stable dispersion in a solution, formulation or film (including after polymerization/curing step).

A further object of the present invention is to provide a polymerizable compound suitable for being applied as stabilizer ligand for or additive to semiconducting light emitting nanoparticles, which can impart increased stability to the nanoparticle surface and which can be polymerized and/or crosslinked to further enhance the stability of the underlying nanoparticle.

A further object of the present invention is to provide a polymerizable compound suitable for being applied as stabilizer ligand for or additive to semiconducting light emitting nanoparticles, which can passivate the nanoparticle surface and provide chemical compatibility to the nanoparticles with various solvents and polymeric systems used in the manufacturing of electronic, optical or biomedical devices, in particular polar solvents, such as PGMEA, and (meth)acrylate- or epoxy-based systems, and which can prevent nanoparticle aggregation and can ensure good dispersion of the nanoparticle in a solution, formulation or film (including after curing).

Further, it is an object of the present invention to provide an optical device having high luminous efficiency, high brightness, high contrast, high reliability and short response times.

A further object of the present invention is to provide a simple process for preparing an optical device.

The present inventors have found that one or more of the above described objects can be addressed by the features as defined in the claims.

Specifically, to solve one or more of the above described problems, the present invention provides for a semiconducting light emitting nanoparticle comprising a core, optionally one or more shell layers, and a compound represented by the following chemical formula (I) as defined herein:

(I)

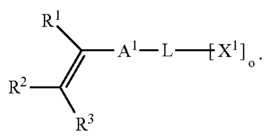

One or more of the above-described problems is also solved by a compound represented by the following chemical formula (III) as defined herein:

(III)

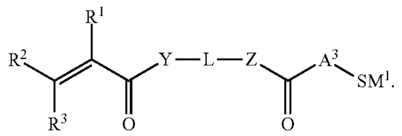

Furthermore, the present invention relates to a composition comprising a semiconducting light emitting nanoparticle according to the present invention and at least one further functional material, and to a composition comprising a semiconducting light emitting nanoparticle, a compound represented by chemical formula (I) as defined herein and at least one further functional material.

In addition, the present invention relates to a formulation comprising a semiconducting light emitting nanoparticle according to the present invention, or a composition as defined herein, and at least one solvent.

The present invention further provides for a use of a semiconducting light emitting nanoparticle or a composition or a formulation according to the present invention in an electronic device, optical device or biomedical device.

Furthermore, the present invention relates to an optical medium and optical device, and to a process for preparing said optical device.

The advantages of the present invention will become more evident from the following detailed description.

DETAILED DESCRIPTION OF THE INVENTION

Figure 1:
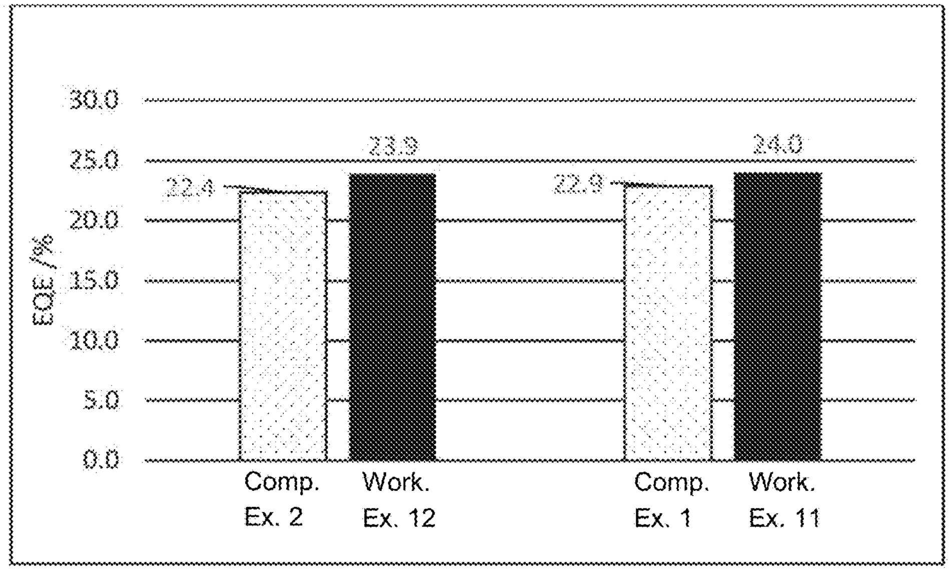
FIG. 1 is a diagram of external quantum efficiency (EQE)/% showing the change of EQE of quantum material containing films obtained from working example 13, each measured at same conditions.

Hereinafter, the best mode for carrying out the present invention is described in detail.

As used herein, a dashed line or an asterisk ("*" or "*") is generally used to denote a linkage or connection point to an adjacent unit or group of a compound, including for example, in case of a polymer, to an adjacent repeating or constitutional unit, or to another group, for example a side chain in case of a monomeric compound.

As used herein, the term "anchor group" denotes an organic functional group capable of interacting with the surface of a semiconducting nanoparticle, thereby binding or chemisorbing the compound comprising the anchor group to the nanoparticle surface, for example via covalent bonding or ionic bonding, or dipole-dipole interaction, without being limited thereto. A compound bound or attached (the terms are used interchangeably herein) or capable of being bound or attached to the nanoparticle surface is referred to herein as a "ligand" or "surface ligand".

The following definitions apply to the chemical groups used as general definitions. They only apply insofar as no more specific definitions are given.

An aryl group in the sense of this invention contains 5 to 40 aromatic ring atoms, of which none is a heteroatom. An aryl group here is taken to mean either a simple aromatic ring, for example benzene, or a condensed (fused) aromatic polycycle, for example naphthalene, phenanthrene, or anthracene. A condensed aromatic polycycle in the sense of the present application consists of two or more simple aromatic rings condensed (fused) with one another. Consequently, an arylene group in the sense of this invention is derived from an aryl group, but has a hydrogen atom removed from two ring carbon atoms, such as phenylene.

A heteroaryl group in the sense of this invention is an aromatic group that contains 5 to 40 aromatic ring atoms, at least one of which is a heteroatom, i.e., a heteroaromatic group. The heteroatoms are preferably selected from N, O and S. A heteroaryl group here is taken to mean either a simple heteroaromatic ring, such as pyridine, pyrimidine or thiophene, or a condensed (fused) heteroaromatic polycycle, such as quinoline or carbazole. A condensed heteroaromatic polycycle in the sense of the present application consists of two or more simple heteroaromatic rings condensed (fused) with one another. Consequently, a heteroarylene group in the sense of this invention is derived from a heteroaryl group, but has a hydrogen atom removed from two ring carbon atoms.

An aryl or heteroaryl group, which may in each case be substituted as defined below and which may be linked to the aromatic or heteroaromatic ring system via any desired positions, or an arylene or heteroarylene group, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An alkaryl or alkarylen group in the sense of this invention is understood to mean an aryl or arylen group as defined above, to which an alkyl group as defined below is bonded, and which may be substituted as defined below.

An alkylheteroaryl or alkylheteroarylen group in the sense of this invention is understood to mean a heteroaryl or a heteroarylene group as defined above, to which an alkyl group as defined below is bonded, and which may be substituted as defined below.

An aromatic ring system in the sense of this invention contains 5 to 40 C aromatic ring atoms in the ring system and does not comprise any heteroatoms as aromatic ring atoms. An aromatic ring system in the sense of this application therefore does not comprise any heteroaryl groups. A heteroaromatic ring system in the sense of this invention contains 5 to 40 aromatic ring atoms, at least one of which is a heteroatom. The heteroatoms are preferably selected from N, O or S. A heteroaromatic ring system is defined as an aromatic ring system above, with the difference that it must obtain at least one heteroatom as one of the aromatic ring atoms.

An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit such as one or more optionally substituted C, Si, N, O or S atoms. The non-aromatic unit in such case comprises preferably less than 10% of the atoms other than H, relative to the total number of atoms other than H of the whole aromatic ring system. Thus, for example, systems such as 9,9'-spirobifluorene, 9,9'-diarylfluorene, triarylamine, diaryl ether, and stilbene are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic ring systems in the sense of this invention, such as, for example, systems such as biphenyl, terphenyl or bipyridine.

For the purposes of the present invention, a straight-chain alkyl group having 1 to 40 C atoms, or a branched or cyclic alkyl group having 3 to 40 C atoms, or a straight-chain alkenyl or alkynyl group having 2 to 40 C atoms, or a branched alkenyl or alkynyl group having 3 to 40 carbon atoms, where, in addition, individual H atoms or $CH_2$ groups in the above-mentioned groups may be substituted as defined below, is preferably taken to mean the radicals methyl, ethyl, n-propyl, i-propyl, n-butyl, i-butyl, s-butyl, t-butyl, 2-methyl-butyl, n-pentyl, s-pentyl, cyclopentyl, neopentyl, n-hexyl, cyclohexyl, neo-hexyl, n-heptyl, cycloheptyl, n-octyl, cyclooctyl, 2-ethylhexyl, trifluoro-methyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. Considering the above definition, a straight-chain alkylene group having 1 to 40 C atoms, a cyclic or branched alkylene group having 3 to 40 C atoms, a straight-chain alkenylene or alkynylene group having 2 to 40 C atoms, or a branched alkenylene group or alkynylene group having 3 to 40 C atoms is taken to mean the respective diradicals of the above-mentioned radicals.

An aralkyl or aralkylene group in the sense of this invention is understood to mean an alkyl or alkylene group as defined above, to which an aryl group as defined above is bonded, and which may be substituted as defined below.

A heteroarylalkyl or heteroarylalkylene group in the sense of this invention is understood to mean an alkyl or alkylene group as defined above, to which a heteroaryl group as defined above is bonded, and which may be substituted as defined below.

An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoro-ethoxy, or 2,2,2-trifluoroethoxy.

According to the present invention a semiconducting light emitting nanoparticle is provided which comprises a core, optionally one or more shell layers, and a compound represented by chemical formula (I)

(I)

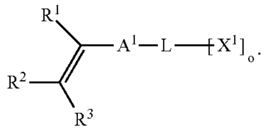

Index "o" is 1, 2 or 3, preferably 1.

Group $R^1$ is H, D, CN a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by $—R^aC{=}CR^a—$, $—C{\equiv}C—$, $Si(R^a)_2$, $Ge(R^a)_2$, $Sn(R^a)_2$, C=O, C=S, C=Se, $C{=}NR^a$, $P({=}O)(R^a)$, SO, $SO_2$, —O—, $NR^a$, —C(=O)O—, or $—C({=}O)NR^a—$, and where one or more H atoms may be replaced by D, F, Cl, Br, I, CN or $NO_2$; an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms may be replaced by D, F, Cl, Br, I, CN or $NO_2$.

Groups $R^2$, $R^3$ are, independently of each other, H, D, CN, a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by $—R^aC{=}CR^a—$, $—C{\equiv}C—$, $Si(R^a)_2$, $Ge(R^a)_2$, $Sn(R^a)_2$, C=O, C=S, C=Se, $C{=}NR^a$, $P({=}O)(R^a)$, SO, $SO_2$, —O—, $NR^a$, —C(=O)O—, or $—C({=}O)NR^a—$, and where one or more H atoms may be replaced by D, F, Cl, Br, I, CN or $NO_2$; or an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms may be replaced by D, F, Cl, Br, I, CN or $NO_2$.

Preferably, one of groups $R^2$ and $R^3$ is H and the other one is as defined above. Even more preferably, both groups $R^2$ and $R^3$ are H.

$A^1$ is divalent group

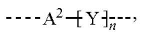

with n=0 or 1, or divalent group

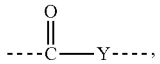

wherein Y is O, NH or S, preferably O or NH, and wherein the dashed lines indicate the bonds to the remainder of the compound (that is, the respective bonds from divalent group $A^1$ to unit C═CR$^1$ and to group L); and wherein $A^2$ is a divalent group selected from an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms of the aromatic or heteroaromatic ring system may be replaced by D, F, Cl, Br, I, CN, $NO_2$.

In a preferred embodiment, $A^1$ is divalent group

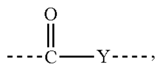

where Y is as defined above.

$R^a$ is at each occurrence, identically or differently, H, D, a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms; a straight-chain alkenyl or alkynyl group having 2 to 40 carbon atoms, preferably 2 to 24 carbon atoms, more preferably 2 to 12 carbon atoms; a branched alkenyl group or alkynyl group having 3 to 40 carbon atoms, preferably 3 to 24 carbon atoms, more preferably 3 to 12 carbon atoms; an aromatic or heteroaromatic ring system having 5 to 40 aromatic ring atoms, preferably 5 to 25 aromatic ring atoms, more preferably 5 to 18 aromatic ring atoms, wherein in each of the above-mentioned groups one or more H atoms may be replaced by D, F, Cl, Br, I, and where two or more adjacent substituents $R^a$ here may optionally form a mono- or polycyclic, aliphatic ring system with one another.

Linking group L is a divalent group selected from a straight-chain alkylene group having 1 to 40 carbon atoms, preferably 3 to 24 carbon atoms, more preferably 4 to 12 carbon atoms; a branched or cyclic alkylene group having 3 to 40 carbon atoms, preferably 4 to 24 carbon atoms, more preferably 5 to 12 carbon atoms; a straight-chain alkenylene or alkynylene group having 2 to 40 carbon atoms, preferably 3 to 24 carbon atoms, more preferably 4 to 12 carbon atoms; or a branched alkenylene group or alkynylene group having 3 to 40 carbon atoms, preferably 4 to 24 carbon atoms, more preferably 5 to 12 carbon atoms, each of which each may be substituted by one or more groups $R^a$, where in each case one or more $CH_2$ groups may be replaced by an arylene group or heteroarylene group having 5 to 40 aromatic ring atoms, preferably 5 to 25 aromatic ring atoms, more preferably 5 to 18 aromatic ring atoms, Si($R^a$)$_2$, Ge($R^a$)$_2$, Sn($R^a$)$_2$, C═O, C═S, C═Se, C═NR$^a$, P(═O)($R^a$), SO, $SO_2$, —O—, NR$^a$, —C(═O)O—, or —C(═O)NR$^a$—, and where one or more H atoms may be replaced by D, F, Cl, Br, I, CN or $NO_2$; an aromatic or heteroaromatic ring system having 5 to 40 aromatic ring atoms, preferably 5 to 25 aromatic ring atoms, more preferably 5 to 18 aromatic ring atoms, an aralkylene group, a heteroaralkylene group, an alkylarylene group or an alkylheteroarylene group, each of which may be substituted by one or more groups $R^a$, and where in each case one or more H atoms may be replaced by D, F, Cl, Br, I, CN, $NO_2$; or a group represented by the following chemical formula (II)

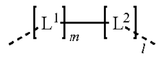
or
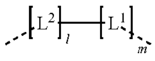
, (II)

wherein m is an integer of 1 to 50, preferably 1 to 25, more preferably 2 to 20, furthermore preferably 4 to 12;

l is an integer of 1 to 25, preferably 1 to 20, more preferably 1 to 12, and furthermore preferably 1 to 8;

$L^1$ is

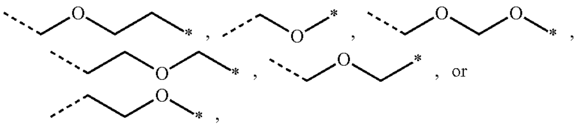

preferably

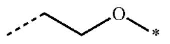
;

$L^2$ is

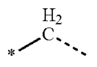
or
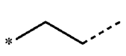
, preferably

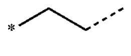
;

wherein a dashed line indicates a bond to the remainder of the compound (that is, a bond from group L, $L^1$ and $L^2$ to group $A^1$ or to group $X^1$) and the symbol "*" marks the bond between groups $L^1$ and $L^2$, and wherein each of $L^1$ and $L^2$ may be substituted by one or more groups $R^a$, where one or more $CH_2$ groups of $L^1$ and $L^2$ may be replaced by $—R^aC═CR^a—$, —C≡C—, $Si(R^a)_2$, $Ge(R^a)_2$, $Sn(R^a)_2$, C═O, C═S, C═Se, $C═NR^a$, $P(═O)(R^a)$, SO, $SO_2$, $NR^a$, or $—C(═O)NR^a—$, and where one or more H atoms in $L^1$ and $L^2$ may be replaced by D, F, Cl, Br, I, CN or $NO_2$.

According to a preferred embodiment, divalent linking group L is selected from a straight-chain alkylene group having 1 to 40 carbon atoms, preferably 3 to 24 carbon atoms, more preferably 4 to 12 carbon atoms; a branched or cyclic alkylene group having 3 to 40 carbon atoms, preferably 4 to 24 carbon atoms, more preferably 5 to 12 carbon atoms; a straight-chain alkenylene or alkynylene group having 2 to 40 carbon atoms, preferably 3 to 24 carbon atoms, more preferably 4 to 12 carbon atoms; or a branched alkenylene group or alkynylene group having 3 to 40 carbon atoms, preferably 4 to 24 carbon atoms, more preferably 5 to 12 carbon atoms, each of which each may be substituted by one or more groups $R^a$, where in each case one or more $CH_2$ groups may be replaced by an arylene group or heteroarylene group having 5 to 40 aromatic ring atoms, preferably 5 to 25 aromatic ring atoms, more preferably 5 to 18 aromatic ring atoms, $Si(R^a)_2$, $Ge(R^a)_2$, $Sn(R^a)_2$, C═O, C═S, C═Se, $C═NR^a$, $P(═O)(R^a)$, SO, $SO_2$, —O—, $NR^a$, —C(═O)O—, or $—C(═O)NR^a—$, and where one or more H atoms may be replaced by D, F, Cl, Br, I, ON or $NO_2$; or a group represented by chemical formula (II),

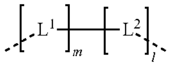

(II)

wherein $L^1$ is

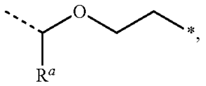,
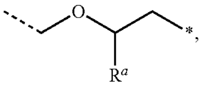,
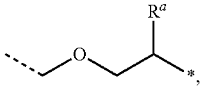,
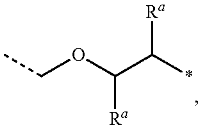,
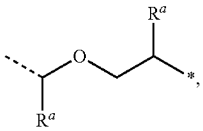,
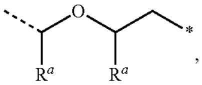,
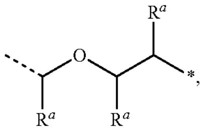,
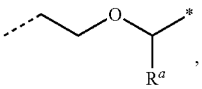,
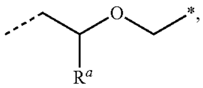,
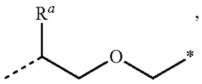,
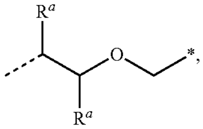
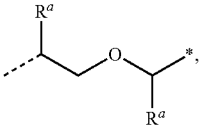, -continued

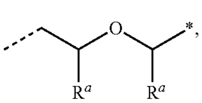,
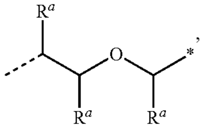,
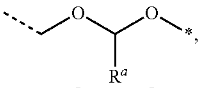,
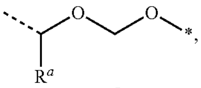,
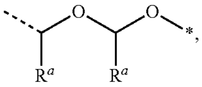,
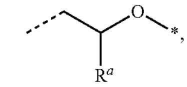,
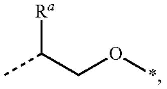,
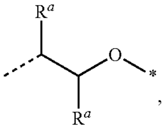,
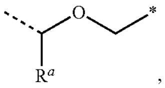,
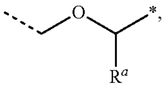,
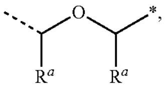, or
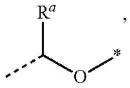, preferably, $L^1$ is

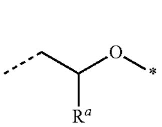,
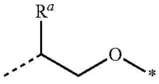 or
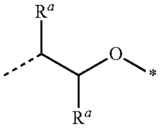;

and $L^2$ is

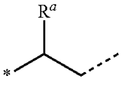 or
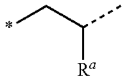, preferably

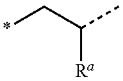

wherein m, l and $R^a$ are as defined above and wherein a dashed line indicates a bond to the remainder of the compound (that is, a bond from group L, $L^1$ and $L^2$ to group $A^1$ or to group $X^1$) and the symbol "*" marks the bond between groups $L^1$ and $L^2$.

$X^1$ is, identically or differently on each occurrence, an anchor group preferably selected from $—COOM^1$, $—PO(OH)(OM^1)$, $—PO(OM^1)_2$, $—OC(S)SM^1$, $—NH_2$, $—NHR^a$, $—N(R^a)_2$, $—SO_3M^1$, $—SM^1$, $—Ar^1—SM^1$, $—OCO\text{-}A^3\text{-}SM^1$, $—COO\text{-}A^3\text{-}SM^1$, $—NH—CO\text{-}A^3\text{-}SM^1$, $SiOR^a$, or $—N(CS_2\,M^1)_2$.

In a preferred embodiment, $X^1$ is, identically or differently on each occurrence, selected from $—OC(S)SM^1$, $—SM^1$, $—Ar^1—SM^1$, $—OCO\text{-}A^3\text{-}SM^1$, $—COO\text{-}A^3\text{-}SM^1$, $—NH—CO\text{-}A^3\text{-}SM^1$, or $—N(CS_2\,M^1)_2$.

$Ar^1$ is a divalent group selected from an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms of the aromatic or heteroaromatic ring system may be replaced by D, F, Cl, Br, I, CN, $NO_2$.

$A^3$ is a divalent group selected from a straight-chain alkylene group having 1 to 40 carbon atoms, preferably 1 to 25 carbon atoms, more preferably 1 to 15 carbon atoms; a branched or cyclic alkylene group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by, $Si(R^a)_2$, $Ge(R^a)_2$, $Sn(R^a)_2$, C═O, C═S, C═Se, $C{=}NR^a$, $P({=}O)(R^a)$, SO, $SO_2$, —O—, $NR^a$, —C(═O)O—, or $-C({=}O)NR^a-$, and where one or more H atoms may be replaced by D, F, Cl, Br, I, CN or $NO_2$; an aromatic or heteroaromatic ring system having 5 to 25 aromatic ring atoms, preferably 5 to 18 aromatic ring atoms, more preferably 5 to 12 aromatic ring atoms, each of which may be substituted by one or more groups $R^a$, and where one or more H atoms of the aromatic or heteroaromatic ring system may be replaced by D, F, Cl, Br, I, CN, $NO_2$.

$M^1$ denotes a hydrogen atom, or a metal cation selected from ½ $Mg^{2+}$, ½ $Cu^{2+}$, ½ $Zn^{2+}$, ½ $Pb^{2+}$, ½ $Sn^{2+}$, ½ $Cd^{2+}$, ⅓ $Bi^{3+}$ or ¼ $Sn^{4+}$, preferably a hydrogen atom, ½ $Mg^{2+}$, ½ $Cu^{2+}$, or ½ $Zn^{2+}$, more preferably a hydrogen atom.

The notation "½ $Mg^{2+}$", "½ $Cu^{2+}$", "½ $Zn^{2+}$" or "½ $Cd^{2+}$", as used herein with respect to $M^1$, should be understood to mean that in the case of a divalent cation, such as $Mg^{2+}$, $Cu^{2+}$, $Zn^{2+}$ or $Cd^{2+}$ (corresponding to "—Mg—", "—Cu—", "—Zn—" or "—Cd—", respectively), then the divalent cation shares its positive charges with two distinct monovalent anionic groups. That is, it shares only one positive charge with a monovalent anionic group $X^1$ and the other positive charge with another monovalent anionic group, for example another monovalent anionic group $X^1$ situated at the same molecule (intra-molecular) or at another different molecule (inter-molecular) of the compound of chemical formula (I). Likewise, a trivalent or tetravalent cation shares its three or four positive charges with anionic groups. For example, in the case of $Mg^{2+}$, the structure can be $-X^1-Mg-X^1-$, where the $X^1$ groups are in the same compound of chemical formula (I) (e.g., where o in chemical formula (I) is 2 for the compound) or where the $X^1$ groups are in different compounds of chemical formula (I) (e.g., where o in chemical formula (I) is 1 for the compounds).

It is believed that the semiconducting light emitting nanoparticles according to the present invention, which comprises a core, optionally one or more shell layers, and a bifunctional, polymerizable compound represented by chemical formula (I) defined herein, show improved thermal stability and long-term stability as well as high quantum yield and luminous efficiency, and therefore can advantageously be applied in electronic devices, optical devices or biomedical devices. Moreover, it has been found that the semiconducting light emitting nanoparticles according to the present invention have high chemical compatibility with various solvents and polymeric systems, in particular (meth) acrylate- or epoxy-based systems, which are typically used as matrix materials in optical devices and, therefore, can well interact with the matrix material and achieve a high degree of crosslinking, show good solubility in solvents, in particular in polar solvents, and do not aggregate but maintain a stable dispersion in a solution, formulation or film (i.e., even after curing).

As used herein the term "polymerizable" means that the respective compound (for example monomeric compound) is capable, preferably upon initiation, of chemically reacting or crosslinking to form polymer chains or three-dimensional networks. Polymerization initiation can be in response to light irradiation or heat, or by means of an initiator compound, without being limited thereto.

According to a further preferred embodiment of the present invention, in chemical formula (I)

$A^1$ is

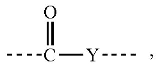

and $X^1$ is, identically or differently on each occurrence, selected from $-OC(S)SM^1$, $-SM^1$, $-Ar^1-SM^1$, $-OCO\text{-}A^3\text{-}SM^1$, $-COO\text{-}A^3\text{-}SM^1$, $-NCO\text{-}A^3\text{-}SM^1$, or $-N(CS_2\,M^1)_2$;

wherein symbols Y, $Ar^1$, $A^3$ and $M^1$ and divalent linking group L are as defined above.

According to a still further preferred embodiment of the present invention, in chemical formula (I)

$A^1$ is

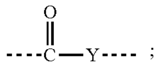

L is selected from a straight-chain alkylene group having 1 to 40 carbon atoms, preferably 3 to 24 carbon atoms, more preferably 4 to 12 carbon atoms; a branched or cyclic alkylene group having 3 to 40 carbon atoms, preferably 4 to 24 carbon atoms, more preferably 5 to 12 carbon atoms; a straight-chain alkenylene or alkynylene group having 2 to 40 carbon atoms, preferably 3 to 24 carbon atoms, more preferably 4 to 12 carbon atoms; or a branched alkenylene group or alkynylene group having 3 to 40 carbon atoms, preferably 4 to 24 carbon atoms, more preferably 5 to 12 carbon atoms, each of which each may be substituted by one or more groups $R^a$, where in each case one or more $CH_2$ groups may be replaced by an arylene group or heteroarylene group having 5 to 40 aromatic ring atoms, preferably 5 to 25 aromatic ring atoms, more preferably 5 to 18 aromatic ring atoms, $Si(R^a)_2$, $Ge(R^a)_2$, $Sn(R^a)_2$, C═O, C═S, C═Se, $C{=}NR^a$, $P({=}O)(R^a)$, SO, $SO_2$, —O—, $NR^a$, —C(═O)O—, or $-C({=}O)NR^a-$, and where one or more H atoms may be replaced by D, F, Cl, Br, I, CN or $NO_2$; or a group represented by chemical formula (II), (II)

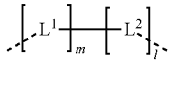

wherein $L^1$ is

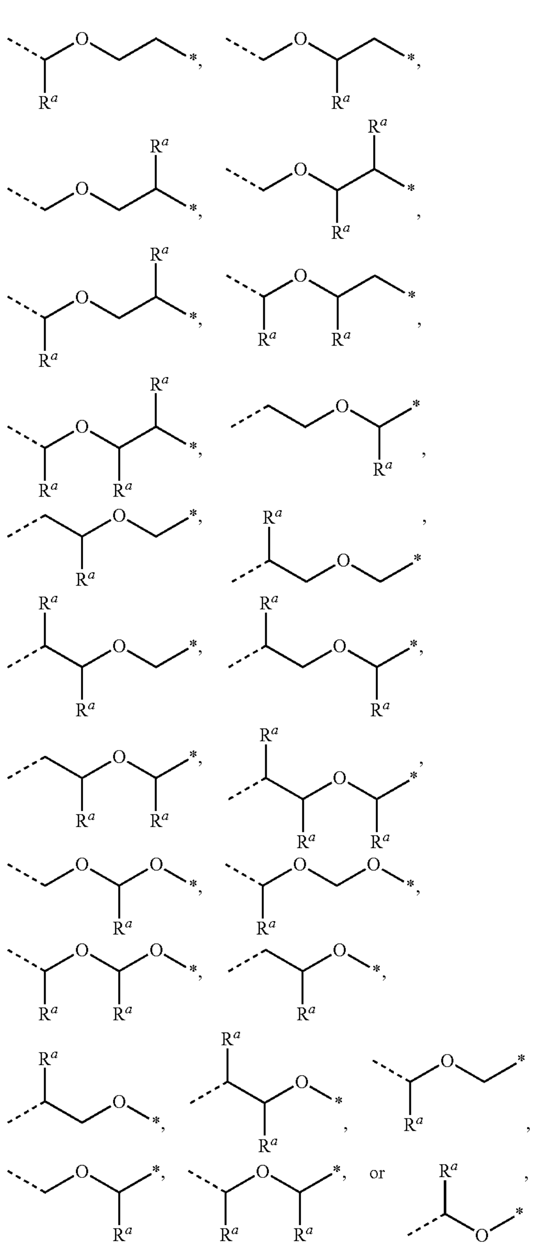

preferably, $L^1$ is

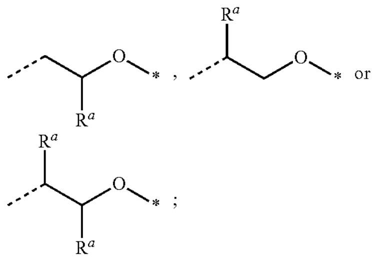

and $L^2$ is

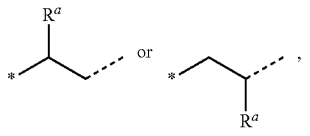

preferably

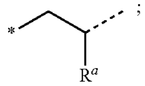

and $X^1$ is, identically or differently on each occurrence, selected from —OC(S)$SM^1$, —$SM^1$, —$Ar^1$—$SM^1$, —OCO-$A^3$-$SM^1$, —NCO-$A^3$-$SM^1$, —COO-$A^3$-$SM^1$, or —$N(CS_2\ M^1)_2$;

wherein symbols and indices m, l, Y, $R^a$, $Ar^1$, $A^3$ and $M^1$ are as defined above.

Further preferably, the compound of chemical formula (I) represents a compound of the following chemical formula (III)

(III)

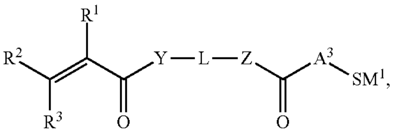

wherein symbols Y, $R^1$, $R^2$, $R^3$, $A^3$, L and $M^1$ are as defined above, and wherein Z is NH or O.

In an even further preferred embodiment of the present invention, the compound of chemical formula (I) or of chemical formula (III) represents a compound of the following chemical formulae (IV), (V-a) or (V-b), preferably chemical formulae (IV), or (V-a), (IV)

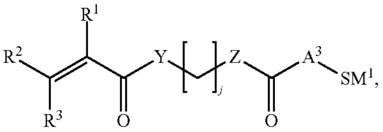

(V-a)

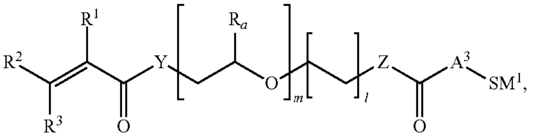

(V-b)

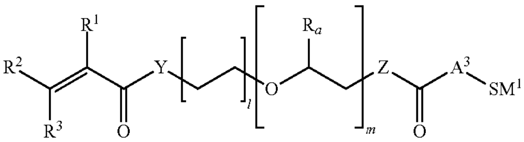

wherein the symbols have the meaning as defined above and index j in chemical formula (IV) is an integer of 1 to 40, preferably 3 to 24, more preferably 4 to 12.

Particularly preferred embodiments of the compound of chemical formula (I) and the compounds of chemical formulae (IV) and (V-a) are the compound represented by the following chemical formulae (IV-1) to (IV-6) and (V-1) to (V-6)

(IV-1)

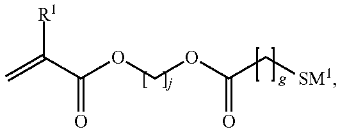

(IV-2)

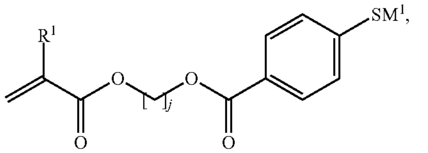

(IV-3)

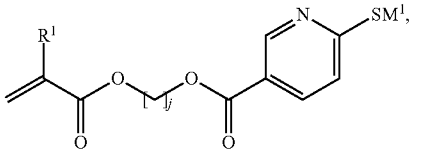

(IV-4)

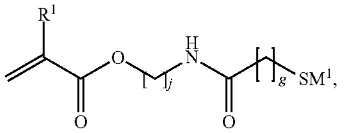

(IV-5)

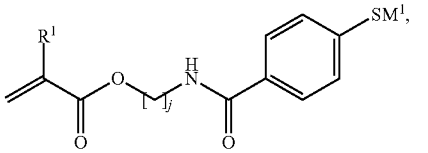

(IV-6)

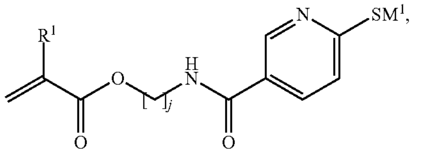

(V-1)

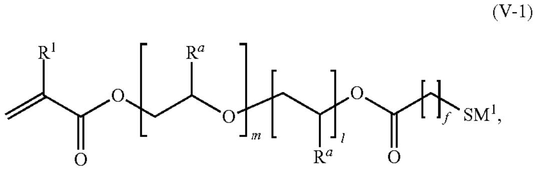

(V-2)

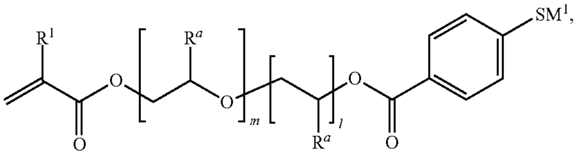

-continued (V-3)

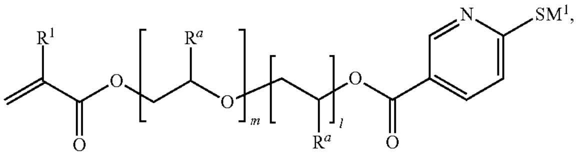

(V-4)

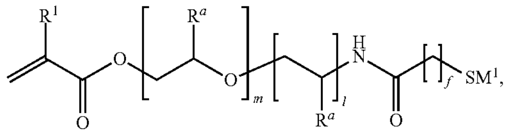

(V-5)

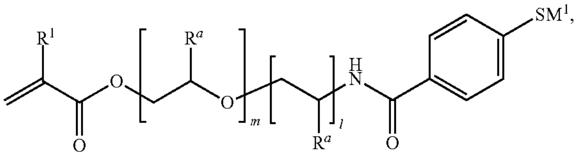

(V-6)

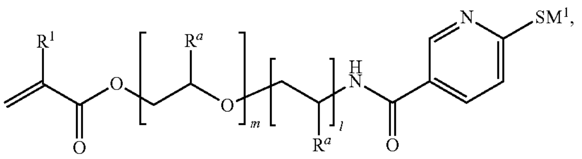

wherein the symbols and indices have the meaning as defined above, and wherein index g and index f are each an integer of 1 to 40, preferably 3 to 24, more preferably 4 to 12.

Particularly preferably, in the compound of chemical formulae (IV-1) to (IV-6) and (V-1) to (V-6) $M^1$ is a hydrogen.

It is further preferable according to the present invention that the compound of chemical formula (I) has a molecular weight in the range of 150 to 2000 Da. More preferably, it has a molecular weight in the range of 150 to 1500 Da, and even more preferably in the range of 200 to 1000 Da.

Semiconducting Light Emitting Nanoparticle

According to the present invention, as an inorganic part of the semiconducting light emitting nanoparticle, a wide variety of publicly known semiconducting light emitting nanoparticles can be used as desired.

A type of shape of the semiconducting light emitting nanoparticle of the present invention is not particularly limited. Any type of semiconducting light emitting nanoparticles, for examples, spherical shaped, elongated shaped, star shaped, polyhedron shaped semiconducting light emitting nanoparticles, can be used.

The semiconducting light emitting nanoparticle of the present invention comprises a core and may optionally comprise one or more shell layers. According to the present invention, the term "shell layer" means the structure covering fully or partially the core. Preferably, said one or more shell layers fully covers said core. The term "core" and "shell" are well known in the art and typically used in the field of quantum materials, such as U.S. Pat. No. 8,221,651 B2.

Said one or more shell layers of the semiconducting light emitting nanoparticle is not particularly limited, and may be a single shell layer, double shell layers, or multishell layers having more than two shell layers, preferably, it is a double shell layers.

According to the present invention, the term "nano" means the size in between 0.1 nm and 999 nm. Preferably, it is from 1 nm to 150 nm.

In a preferred embodiment of the present invention, the semiconducting light emitting nanoparticle of the present invention is a quantum sized material.

According to the present invention, the term "quantum sized" means the size of the semiconductor material itself without compounds or another surface modification, which can show the quantum confinement effect, like described in, for example, ISBN:978-3-662-44822-9.

Preferably, the size of the overall structures of the quantum sized material, is from 1 nm to 100 nm, more preferably, it is from 1 nm to 30 nm, even more preferably, it is from 5 nm to 15 nm.

According to the present invention, said core of the semiconducting light emitting nanoparticle can vary.

For example, CdS, CdSe, CdTe, ZnS, ZnSe, ZnSeS, ZnTe, ZnO, GaAs, GaP, GaSb, HgS, HgSe, HgSe, HgTe, InAs, InP, InPS, InPZnS, InPZn, InPGa, InSb, AlAs, AlP, AlSb, $Cu_2S$, $Cu_2Se$, $CuInS_2$, $CuInSe_2$, $Cu_2(ZnSn)S_4$, $Cu_2(InGa)S_4$, $TiO_2$ alloys and a combination of any of these can be used.

In a preferred embodiment of the present invention, said core of the semiconducting light emitting nanoparticle comprises one or more of group 13 elements of the periodic table and one or more of group 15 elements of the periodic table. For example, GaAs, GaP, GaSb, InAs, InP, InPS, InPZnS, InPZn, InPGa, InSb, AlAs, AlP, AlSb, $CuInS_2$, $CuInSe_2$, $Cu_2(InGa)S_4$, and a combination of any of these.

Even more preferably, the core comprises In and P atoms. For example, InP, InPS, InPZnS, InPZn, InPGa.

The at least one of the shell layers comprises a $1^{st}$ element of group 12, 13 or 14 of the periodic table and a $2^{nd}$ element of group 15 or 16 of the periodic table, preferably, all shall layers comprise a $1^{st}$ element of group 12, 13 or 14 of the periodic table and a $2^{nd}$ element of group 15 or 16 of the periodic table.

In a preferred embodiment of the present invention, at least one of the shell layers comprises a $1^{st}$ element of group 12 of the periodic table and a $2^{nd}$ element of group 16 of the periodic table. For examples, CdS, CdZnS, ZnS, ZnSe, ZnSSe, ZnSSeTe, CdS/ZnS, ZnSe/ZnS, ZnS/ZnSe shell layers can be used. Preferably, all shall layers comprise a $1^{st}$ element of group 12 of the periodic table and a $2^{nd}$ element of group 16 of the periodic table.

More preferably, at least one shell layer is represented by following formula (VI), $$ZnS_xSe_yTe_z, \tag{VI}$$

wherein the formula (I), 0≤x≤1, 0≤y≤1, 0≤z≤1, and x+y+z=1, with even more preferably being of 0≤x≤1, 0≤y≤1, z=0, and x+y=1.

For examples, ZnS, ZnSe, ZnSeS, ZnSeSTe, CdS/ZnS, ZnSe/ZnS, ZnS/ZnSe shell layers can be used preferably.

Preferably, all shell layers are represented by formula (VI).

For example, as a semiconducting light emitting nanoparticle for green and/or red emission use, CdSe/CdS, CdSeS/CdZnS, CdSeS/CdS/ZnS, ZnSe/CdS, CdSe/ZnS, InP/ZnS, InP/ZnSe, InP/ZnSe/ZnS, InP/ZnS/ZnSe, InPZn/ZnS, InPZn/ZnSe/ZnS, InPZn/ZnS/ZnSe, ZnSe/CdS, ZnSe/ZnS semiconducting light emitting nanoparticle or combination of any of these, can be used.

More preferably, it is InP/ZnS, InP/ZnSe, InP/ZnSe/ZnS, InP/ZnS/ZnSe, InPZn/ZnS, InPZn/ZnSe/ZnS, InPZn/ZnS/ZnSe can be used.

In a more preferred embodiment of the present invention, said shell layers of the semiconducting light emitting nanoparticle are double shell layers.

Said semiconducting light emitting nanoparticles are publicly available, for example, from Sigma-Aldrich and/or described in, for example, *ACS Nano,* 2016, 10 (6), pp 5769-5781, Chem. Moter. 2015, 27, 4893-4898, and the international patent application laid-open No. WO2010/095140A.

Additional Compound

According to an embodiment of the present invention, the semiconducting light emitting nanoparticle according to the invention comprises a compound or ligand that is attached onto the outermost nanoparticle surface (that is, the outermost surface of the core or, if present, the shell layer(s)), which compound or ligand is preferably represented by the bifunctional, polymerizable compound of chemical formula (I) as defined herein.

The semiconducting light emitting nanoparticle of the present invention may optionally comprise one or more further types of compounds or ligands, which compounds or ligands are different from the compound represented by chemical formula (I), attached to the outermost surface of the nanoparticle.

Accordingly, the outermost surface of the core or the shell layer(s) of the semiconducting light emitting nanoparticle may be over-coated with different types of compounds together with the compound represented by chemical formula (I).

In case one or more of said further types of compounds or ligands are attached onto the outermost surface of the core or the shell layer(s) of the semiconducting light emitting nanoparticle together with the compound represented by chemical formula (I), the amount of the compound represented by chemical formula (I) is in the range from 30 wt. % to 99.9 wt % of the total compounds attached onto the outermost surface of the core or the shell layer(s), preferably from 50 wt % to 95 wt %, more preferably it is in the range from 60 wt. % to 90 wt. %.

Without wishing to be bound by theory it is believed that such one or more further types of compounds can lead to disperse the semiconducting light emitting nanoparticle in a solvent more easily.

The further types of compounds in common use include phosphines and phosphine oxides such as Trioctylphosphine oxide (TOPO), Trioctylphosphine (TOP), and Tributylphosphine (TBP); phosphonic acids such as Dodecylphosphonic acid (DDPA), Tridecylphosphonic acid (TDPA), Octadecylphosphonic acid (ODPA), and Hexylphosphonic acid (HPA); amines such as Dedecyl amine (DDA), Tetradecyl amine (TDA), Hexadecyl amine (HDA), and Octadecyl amine (ODA), Oleylamine (OLA), thiols such as hexadecane thiol and hexane thiol; carboxylic acids such as oleic acid, stearic acid, myristic acid; acetic acid and a combination of any of these.

Examples of such compounds used as ligand have been described in, for example, the laid-open international patent application No. WO 2012/059931A.

Compound

The present invention furthermore relates to a compound represented by general formula (III)

(III)

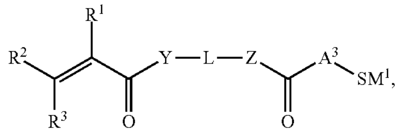

wherein

Y is O, NH or S, preferably O or NH;

Z is O or NH;

$R^1$ is H, D, CN a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by —$R^aC$═$CR^a$—, —C≡C—, $Si(R^a)_2$, $Ge(R^a)_2$, $Sn(R^a)_2$, C═O, C═S, C═Se, C═$NR^a$, P(═O)($R^a$), SO, $SO_2$, —O—, $NR^a$, —C(═O)O—, or —C(═O)$NR^a$—, and where one or more H atoms may be replaced by D, F, Cl, Br, I, CN or $NO_2$; an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms may be replaced by D, F, Cl, Br, I, CN or $NO_2$;

$R^2$, $R^3$ are, independently of each other, H, D, CN, a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by —$R^aC$═$CR^a$—, —C≡C—, $Si(R^a)_2$, $Ge(R^a)_2$, $Sn(R^a)_2$, C═O, C═S, C═Se, C═$NR^a$, P(═O)($R^a$), SO, $SO_2$, —O—, $NR^a$, —C(═O)O—, or —C(═O)$NR^a$—, and where one or more H atoms may be replaced by D, F, Cl, Br, I, CN or $NO_2$;

or an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms may be replaced by D, F, Cl, Br, I, CN or $NO_2$;

$R^a$ is at each occurrence, identically or differently, H, D, a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms; a straight-chain alkenyl or alkynyl group having 2 to 40 carbon atoms, preferably 2 to 24 carbon atoms, more preferably 2 to 12 carbon atoms; a branched alkenyl group or alkynyl group having 3 to 40 carbon atoms, preferably 3 to 24 carbon atoms, more preferably 3 to 12 carbon atoms; an aromatic or heteroaromatic ring system having 5 to 40 aromatic ring atoms, preferably 5 to 25 aromatic ring atoms, more preferably 5 to 18 aromatic ring atoms, wherein in each of the above-mentioned groups one or more H atoms may be replaced by D, F, Cl, Br, I, and where two or more adjacent substituents $R^a$ here may optionally form a mono- or polycyclic, aliphatic ring system with one another;

L is a divalent group selected from a straight-chain alkylene group having 1 to 40 carbon atoms, preferably 3 to 24 carbon atoms, more preferably 4 to 12 carbon atoms; a branched or cyclic alkylene group having 3 to 40 carbon atoms, preferably 4 to 24 carbon atoms, more preferably 5 to 12 carbon atoms; a straight-chain alkenylene or alkynylene group having 2 to 40 carbon atoms, preferably 3 to 24 carbon atoms, more preferably 4 to 12 carbon atoms; or a branched alkenylene group or alkynylene group having 3 to 40 carbon atoms, preferably 4 to 24 carbon atoms, more preferably 5 to 12 carbon atoms, each of which each may be substituted by one or more groups $R^a$, where in each case one or more $CH_2$ groups may be replaced by an arylene group or heteroarylene group having 5 to 40 aromatic ring atoms, preferably 5 to 25 aromatic ring atoms, more preferably 5 to 18 aromatic ring atoms, $Si(R^a)_2$, $Ge(R^a)_2$, $Sn(R^a)_2$, C═O, C═S, C═Se, C═$NR^a$, P(═O)($R^a$), SO, $SO_2$, —O—, $NR^a$, —C(═O)O—, or —C(═O)$NR^a$—, and where one or more H atoms may be replaced by D, F, Cl, Br, I, CN or $NO_2$; an aromatic or heteroaromatic ring system having 5 to 40 aromatic ring atoms, preferably 5 to 25 aromatic ring atoms, more preferably 5 to 18 aromatic ring atoms, an aralkylene group, a heteroaralkylene group, an alkylarylene group or an alkylheteroarylene group, each of which may be substituted by one or more groups $R^a$, and where in each case one or more H atoms may be replaced by D, F, Cl, Br, I, CN, $NO_2$; or a group represented by the following chemical formula (II)

(II)

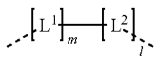 or 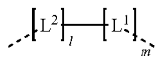

wherein m is an integer of 1 to 50, preferably 1 to 25, more preferably 2 to 20, and furthermore preferably 4 to 12;

l is an integer of 1 to 25, preferably 1 to 20, more preferably 1 to 12, and furthermore preferably 1 to 8;

$L^1$ is

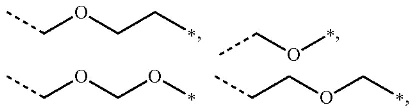

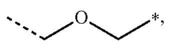 or 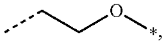

preferably

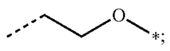

$L^2$ is

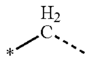 or 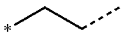, preferably

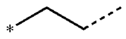;

wherein a dashed line indicates a bond to the remainder of the compound (that is, a bond from group L, $L^1$ and $L^2$ to group Y or group Z) and the symbol "*" marks the bond between groups $L^1$ and $L^2$, and wherein each of $L^1$ and $L^2$ may be substituted by one or more groups $R^a$, where one or more $CH_2$ groups of $L^1$ and $L^2$ may be replaced by —$R^aC$═$CR^a$—, —C≡C—, $Si(R^a)_2$, $Ge(R^a)_2$, $Sn(R^a)_2$, C═O, C═S, C═Se, C═$NR^a$, P(═O)($R^a$), SO, $SO_2$, $NR^a$, or —C(═O)$NR^a$—, and where one or more H atoms in $L^1$ and $L^2$ may be replaced by D, F, Cl, Br, I, CN or $NO_2$;

$A^3$ is a divalent group selected from a straight-chain alkylene group having 1 to 40 carbon atoms, preferably 1 to 25 carbon atoms, more preferably 1 to 15 carbon atoms; a branched or cyclic alkylene group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by, $Si(R^a)_2$, $Ge(R^a)_2$, $Sn(R^a)_2$, C═O, C═S, C═Se, C═$NR^a$, P(═O)($R^a$), SO, $SO_2$, —O—, $NR^a$, —C(═O)O—, or —C(═O)$NR^a$—, and where one or more H atoms may be replaced by D, F, Cl, Br, I, CN or $NO_2$; an aromatic or heteroaromatic ring system having 5 to 25 aromatic ring atoms, preferably 5 to 18 aromatic ring atoms, more preferably 5 to 12 aromatic ring atoms, each of which may be substituted by one or more groups $R^a$, and where one or more H atoms of the aromatic or heteroaromatic ring system may be replaced by D, F, Cl, Br, I, CN, $NO_2$; and $M^1$ denotes a hydrogen atom, or a metal cation selected from ½ $Mg^{2+}$, ½ $Cu^{2+}$, ½ $Zn^{2+}$, ½ $Pb^{2+}$, ½ $Sn^{2+}$, ½ $Cd^{2+}$, ⅓ $Bi^{3+}$ or ¼ $Sn^{4+}$, preferably a hydrogen atom, ½ $Mg^{2+}$, ½ $Cu^{2+}$, or ½ $Zn^{2+}$, more preferably a hydrogen atom.

The preferred embodiments of the compound, symbols and indices of chemical formula (III) defined above in relation to the semiconducting light emitting nanocrystal are likewise preferred in this connection.

Particularly preferably, the compound of chemical formula (III) according to the present invention represents a compound of the chemical formulae (IV), (V-a) or (V-b) as defined above.

Even more preferably, the compound of chemical formula (III) according to the present invention represents one of the compounds of chemical formulae (IV-1) to (IV-6) and (V-1) to (V-6) as defined above.

It is believed that the bifunctional polymerizable compounds of the chemical formula (III) as defined herein, which comprises a thiol/thiolate functional group and a polymerizable acrylate-based functional group, separated from each other by a divalent linking or bridging group (i.e., group L), are particularly suitable for being applied as ligand for or additive to semiconducting light emitting nanoparticles, as they are highly compatibility to polar solvents, such as PGMEA, and to (meth)acrylate- or epoxy-based systems (that is, they can chemically interact with such systems), which are typically used in device manufacturing processes. Due to their high compatibility, these compounds can advantageously be chemically linked to the ((meth)acrylate) matrix material through crosslinking involving the double bond, to thereby impart higher stability to the nanoparticles, in particular after film curing and film heating, and they can prevent nanoparticle aggregation and can ensure good dispersion of the nanoparticles in a solution, formulation or film (including after film curing), to thereby further enhance the stability of the nanoparticles.

Composition

Especially when being used in electronic devices, optical devices or biomedical devices, the semiconducting light emitting nanoparticle according to the present invention may be combined with further functional materials, such as host or matrix materials and/or optically transparent polymers, which are commonly used in electronic device, optical device or biomedical device according to the prior art, to form a composition. A great variety of suitable functional materials is known to those skilled in the art in the field of electronic, optical or biomedical devices, which may be preferably used.

In a first aspect, the present invention thus further provides for a composition comprising the semiconducting light emitting nanoparticle according to the present invention, that is, a semiconducting light emitting nanoparticle comprising a core, optionally one or more shell layers, and a compound represented by chemical formula (I) as defined herein, and at least one further functional material, In an embodiment of this aspect of the invention, the semiconducting light emitting nanoparticle comprises a compound or ligand that is attached onto the outermost nanoparticle surface (that is, the outermost surface of the core or, if present, the shell layer(s)), said compound or ligand preferably being represented by the bifunctional, polymerizable compound of chemical formula (I) as defined herein.

The at least one further functional material is preferably selected from the group consisting of organic light emitting materials, inorganic light emitting materials, charge transporting materials, host or matrix materials, optically transparent polymers, anti-oxidants or stabilizers, radical quenchers, photo initiators or polymerization initiators, wetting and dispersing agents, scattering particles, reflective index adjusting materials, developer-dissolution promoters, scum removers, adhesion enhancers, polymerization inhibitors, defoaming agents, surfactants and sensitizers. Preferably, the at least one further functional material is a host or matrix material, which is more preferably selected from (meth)acrylate monomers or polymers. (Meth)acrylate monomers as represented by chemical formula (VII) defined below are especially preferred.

In the following, preferred examples of the further functional materials that can be used according to the present invention are described, without being limited thereto.

As used herein, a polymerization initiator is a molecule or compound that creates reactive species (free radicals, cations or anions) by different pathways including dissociation and electron transfer in order to initiate or facilitate crosslinking or polymerization reactions. Accordingly, a photoinitiator is a molecule or compound that creates such reactive species when exposed to light (UV or visible light), and a thermo-initiator is a molecule or compound that creates such reactive species when heat is applied.

The polymerization initiator is not particularly limited within the present invention and may be, for example, a photo-initiator, a nucleophilic initiator, a radical initiator or a thermo-initiator, suitable examples of which are known to a person skilled in the art. Preferably, a photo-initiator or thermo-initiator is used.

Suitable wetting and dispersing agents preferably comprise an anchoring group selected from phosphine groups, phosphine oxide groups, phosphate groups, phosphonate groups, thiol groups, tertiary amine groups, carboxyl groups, hetero cyclic groups, silane groups, sulfonic acids, hydroxyl groups, and phosphonic acids. Examples of such preferred wetting and dispersing agent are disclosed, for example, in WO 2017/054898 A1.

According to the present invention, as said organic light emitting materials and charge transporting materials any type of publicly known materials can be used. For example, well known organic fluorescent materials, organic host materials, organic dyes, organic electron transporting materials, organic metal complexes, and organic hole transporting materials may be used preferably.

According to the present invention, as the light scattering particles, any type of publically known light scattering particles having different refractive index from the matrix material of the layer which includes said light scattering particles and can give Mie scattering effects may be used as desired.

Preferably, as the scattering particles small particles of inorganic oxides such as $SiO_2$, $SnO_2$, CuO, CoO, $Al_2O_3$ $TiO_2$, $Fe_2O_3$, $Y_2O_3$, ZnO, MgO; organic particles such as polymerized polystyrene, polymerized PMMA; inorganic hollow oxides such as hollow silica; or a combination of any of these may be used.

The adhesion enhancer has a function of preventing the pattern from being peeled off by stress applied after curing when a cured film is formed from the polymerizable composition of the present invention. As the adhesion enhancer, imidazoles and silane coupling agents are preferably adopted. Examples of the imidazoles include 2-hydroxybenzimidazole, 2-hydroxyethylbenzimidazole, benzimidazole, 2-hydroxyimidazole, imidazole, 2-mercaptoimidazole, and 2-aminoimidazole. Among them, particularly preferred are 2-hydroxybenzimidazole, benzimidazole, 2-hydroxyimidazole and imidazole.

The developer-dissolution promoter or the scum remover has a function of controlling solubility of the formed coating in a developer and thereby of preventing scum from remaining on the substrate after development. As this additive, crown ethers can be adopted. Crown ethers having the simplest structures are represented by the general formula: $(—CH_2—CH_2—O—)_n$. Among them, crown ethers of the formula in which n is 4 to 7 are preferably used in the present invention. Meanwhile, crown ethers are often individually referred to as "x-crown-y-ether" in which x and y represent the total number of atoms forming the ring and the number of oxygen atoms included therein, respectively. In the present invention, the additive can be preferably selected from the group consisting of crown ethers of X=12, 15, 18 and 21 and y=x/3, benzo-condensed products thereof, and cyclohexyl condensed products thereof. Preferred examples of the crown ethers include 2-crown-7-ether, 18-crown-6-ether, 15-crown-5-ether, 12-crown-4-ether, dibenzo-21-crown-7-ether, dibenzo-18-crown-6-ether, dibenzo-15-crown-5-ether, dibenzo-12-crown-4-ether, dicyclohexyl-21-crown-7-ether, dicyclohexyl-18-crown-6-ether, dicyclohexyl-5-crown-5-ether, and dicyclohexyl-12-crown-4-ether. Among them, it is particularly preferred to select the additive from the group consisting of 18-crown-6-ether and 15-crown-5-ether. The amount thereof is preferably 0.05 to 15 weight parts, more preferably 0.1 to 10 weight parts, based on 100 weight parts of the organopolysilicon compound of the present invention.

As the polymerization inhibitor, nitrone derivatives, nitroxide radical derivatives and hydroquinone derivatives, such as, hydroquinone, methylhydroquinone and butyllhydroquinine, can be incorporated. Those can be used singly or in combination of two or more. The amount thereof is preferably 0.1 to 10 weight parts based on 100 weight parts of the organopolysilicon compound of the present invention.

Examples of the defoaming agent include: alcohols ($C_1$ to $C_{18}$); higher fatty acids, such as, oleic acid and stearic acid; higher fatty acid esters, such as, glycerin monolaurate; polyethers, such as, polyethylenglycol (PEG) (Mn: 200 to 10000) and polypropyleneglycol (Mn: 200 to 10000); silicone compounds, such as, dimethyl silicone oil, alkyl-modified silicone oil and fluoro-silicone oil; and organic siloxane surfactants described below in detail. Those can be used singly or in combination of two or more. The amount thereof is preferably 0.1 to 3 weight parts based on 100 weight parts of the organopolysilicon compound of the present invention.

If necessary, the polymerizable composition of the present invention can further contain a surfactant, which is incorporated with the aim of improving coatability, developability and the like The surfactants usable in the present invention are, for example, nonionic, anionic and amphoteric surfactants.

Examples of the nonionic surfactants include: polyoxyethylene alkyl ethers, such as, polyoxyethylene lauryl ether, polyoxyethylene oleyl ether and polyoxyethylene cetyl ether; polyoxyethylene fatty acid diethers; polyoxyethylene fatty acid monoethers; polyoxyethylene-polyoxypropylene block polymer; acetylene alcohol; acetylene glycol derivatives, such as, acetylene glycol, polyethoxyate of acetylene alcohol, and polyethoxyate of acetylene glycol; silicon-containing surfactants, such as, Fluorad ([trademark], manufactured by Sumitomo 3M Limited), MEGAFAC ([trademark], manufactured by DIC Corporation), and Surufuron ([trademark], manufactured by Asahi Glass Co., Ltd.); and organic siloxane surfactants, such as, KP341 ([trademark], manufactured by Shin-Etsu Chemical Co., Ltd.). Examples of the above acetylene glycols include: 3-methyl-1-butyne-3-ol, 3-methyl-1-pentyne-3-ol, 3,6-dimethyl-4-octyne-3,6-diol, 2,4,7,9-tetramethyl-5-decyne-4,7-diol, 3,5-dimethyl-1-hexyne-3-ol, 2,5-dimethyl-3-hexyne-2,5-diol, and 2,5-dimethyl-2,5-hexanediol.

Examples of the anionic surfactants include: ammonium salts and organic amine salts of alkyldiphenylether disulfonic acids, ammonium salts and organic amine salts of alkyldiphenylether sulfonic acids, ammonium salts and organic amine salts of alkylbenzenesulfonic acids, ammonium salts and organic amine salts of polyoxyethylenealkylether sulfuric acids, and ammonium salts and organic amine salts of alkylsulfuric acids. Further, examples of the amphoteric surfactants include 2-alkyl-N-carboxymethyl-N-hydroxyethyl imidazolium betaine, and laurylic acid amidopropyl hydroxy sulfone betaine.

Those surfactants can be used singly or in combination of two or more. The amount thereof is normally 50 to 2000 ppm, preferably 100 to 1000 ppm based on the polymerizable composition of the present invention.

According to necessity, a sensitizer can be incorporated into the polymerizable composition of the present invention. Examples of the sensitizer preferably used in the composition of the present invention include Coumarin, ketocoumarin, derivatives thereof, thiopyrylium salts, and acetophenone. Specifically, concrete examples thereof include: sensitizing dyes, such as, p-bis(o-methylstryl)benzene, 7-dimethylamino-4-methylquinolone-2,7-amino-4-methylcoumarin, 4,6-dimethyl-7-ethylaminocoumarin, 2-(p-dimethylaminostryl)pyridylmethyl iodide, 7-diethylaminocoumarin, 7-diethylamino-4-methylcoumarin, 2,3,5,6-1H,4H-tetrahydro-8-methylquinolidino-<9,9a,1-gh>coumarin, 7-diethylamino-4-trifluoromethylcoumarin, 7-dimethylamino-4-trifluoromethylcoumarin, 7-amino-4-trifluoromethylcoumarin, 2,3,5,6-1H,4H-tetrahydroquinolidino<9,9a,1-gh>Coumarin, 7-ethylamino-6-methyl-4-trifluoromethylcoumarin, 7-ethylamino-4-trifluoromethylcoumarin, 2,3,5,6-1H,4H-tetrahydro-9-carboethoxyquinolidino-<9,9a,1-gh>coumarin, 3-(2'-N-methyl-benzimidazolyl)-7-N,N-diethylaminocoumarin, N-methyl-4-trifluoromethylpiperidino-<3,2-g>Coumarin, 2-(p-dimethylaminostryl)benzo-thiazolylethyl iodide, 3-(2'-benzimidazolyl)-7-N,N-diethylaminocoumarin, 3-(2'-benzothiazolyl)-7-N,N-diethylaminocoumarin, and pyrylium or thiopyrylium salts represented by the following formula.

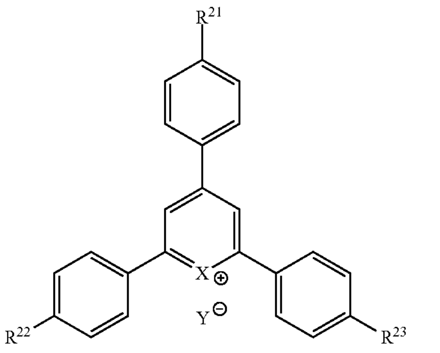

| X | $R_1$ | $R_2$ | $R_3$ | Y |
|---|---|---|---|---|
| S | $OC_4H_9$ | H | H | $BF_4$ |
| S | $OC_4H_9$ | $OCH_3$ | $OCH_3$ | $BF_4$ |
| S | H | $OCH_3$ | $OCH_3$ | $BF_4$ |
| S | $N(CH_3)_2$ | H | H | $ClO_2$ |
| O | $OC_4H_9$ | H | H | $SbF_6$ |

The sensitizing dye makes it possible to carry out patterning by use of inexpensive light sources, such as, a high-pressure mercury lamp (360 to 430 nm). The amount thereof is preferably 0.05 to 15 weight parts, more preferably 0.1 to 10 weight parts based on 100 weight parts of the organopolysilicon compound of the present invention.

As the sensitizer, it is also possible to adopt a compound having an anthracene skeleton as disclosed, for example, in WO 2012/059931 A1 or JP 3820633 B. When the sensitizer having an anthracene skeleton is added, the amount thereof is preferably 0.01 to 5 weight parts based on 100 weight parts of the organopolysilicon compound of the present invention.

Further, if necessary, a stabilizer can be also added into the composition of the present invention. The stabilizer can be freely selected from those generally known. However, in the present invention, aromatic amines are preferred because they have high effect on stabilization. Among those aromatic amines, preferred are pyridine derivatives and particularly preferred are pyridine derivatives having bulky substituent groups at 2- and 6-positions. Concrete examples thereof are as follows:

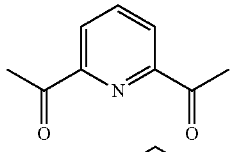
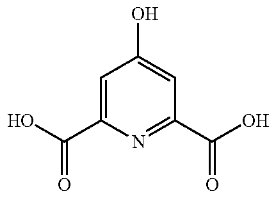
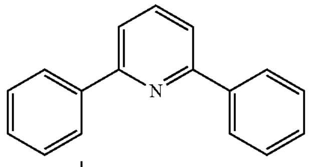
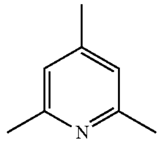
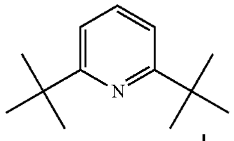
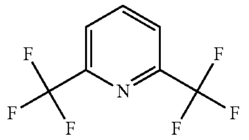
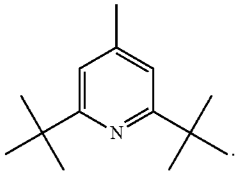.

In a further preferred embodiment of this aspect of the invention, the at least one further functional material is an optically transparent polymer.

According to the present invention, a wide variety of publicly known transparent matrix materials suitable for optical devices can be used preferably as an optically transparent polymer.

As used herein, the term "transparent" means at least around 60% of incident light transmit at the thickness used in an optical medium and at a wavelength or a range of wavelength used during operation of an optical medium. Preferably, it is over 70%, more preferably, over 75%, the most preferably, it is over 80%.

In a preferred embodiment of the present invention, the optical transparent polymer is a transparent matrix material.

As used herein, the term "polymer" means a material having a repeating unit and having the weight average molecular weight (Mw) 1000 g/mol, or more. The molecular weight Mw is determined by means of GPC (=gel permeation chromatography) against an internal polystyrene standard.

In a further preferred embodiment of the present invention, the glass transition temperature (Tg) of the transparent polymer is 70° C. or more and 250° C. or less.

Tg is measured based on changes in the heat capacity observed in Differential scanning colorimetry like described in http://pslc.ws/macrog/dsc.htm; Rickey J Seyler, Assignment of the Glass Transition, ASTM publication code number (PCN) 04-012490-50.

For example, as the transparent polymer for the transparent matrix material, poly(meth)acrylates, epoxys, polyurethanes or polysiloxanes can be used preferably.

Further preferably, the weight average molecular weight (Mw) of the polymer as the transparent matrix material is in the range from 1,000 to 300,000 g/mol, more preferably it is from 10,000 to 250,000 g/mol.

In a further aspect, the present invention also provides for a composition comprising a compound represented by chemical formula (I) as defined herein, or a compound represented by chemical formula (III) as defined herein, or a compound represented by formulae (IV), (V-a) or (V-b) as defined herein; and at least one further functional material, which is preferably selected from the group consisting of organic light emitting materials, inorganic light emitting materials, charge transporting materials, host or matrix materials, optically transparent polymers, anti-oxidants or stabilizers, radical quenchers, photo initiators or polymerization initiators, wetting and dispersing agents, scattering particles, reflective index adjusting materials, developer-dissolution promoters, scum removers, adhesion enhancers, polymerization inhibitors, defoaming agents, surfactants and sensitizers.

The preferred examples of the further functional materials as defined above are likewise preferred in this connection.

In a preferred embodiment of the composition according to this aspect of the invention, the at least one further functional material is a host or matrix material, which is even more preferably selected from (meth)acrylate monomers or polymers. (Meth)acrylate monomers as represented by chemical formula (VII) defined below are especially preferred.

In another aspect, the present invention also provides for a composition comprising a semiconducting light emitting nanoparticle having at least a core and, optionally, one or more shell layers, a compound represented by chemical formula (I) as defined herein (I)

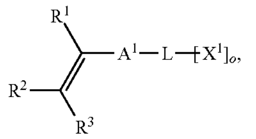

and at least one further functional material, which is preferably selected from the group consisting of organic light emitting materials, inorganic light emitting materials, charge transporting materials, host or matrix materials, optically transparent polymers, anti-oxidants or stabilizers, radical quenchers, photo initiators or polymerization initiators, wetting and dispersing agents, scattering particles, reflective index adjusting materials, developer-dissolution promoters, scum removers, adhesion enhancers, polymerization inhibitors, defoaming agents, surfactants and sensitizers.

The preferred examples of the further functional materials as defined above are likewise preferred in this connection.

As an inorganic part of the semiconducting light emitting nanoparticle comprised in the composition according to this aspect of the present invention, a wide variety of publicly known semiconducting light emitting nanoparticles can be used as desired. In particular, a type of shape of the semiconducting light emitting nanoparticle and its core and optional one or more shell layers may be as defined above in relation to the semiconducting light emitting nanoparticle of the present invention.

In addition, the outermost surface of the core or the shell layer(s) of the semiconducting light emitting nanoparticle comprised in the composition according to this aspect of the present invention may be over-coated with different types of compounds or ligands as defined above in relation to the semiconducting light emitting nanoparticle of the present invention.

In a preferred embodiment of the composition according to this aspect of the invention, the at least one further functional material is a host or matrix material, which is more preferably selected from (meth)acrylate monomers or polymers.

The (meth)acrylate monomer is preferably represented by the following chemical formula (VII)

(VII)

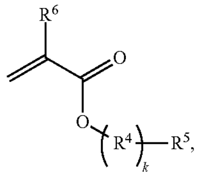

wherein $R^4$ is a straight alkylene chain or alkoxylene chain having 1 to 15 carbon atoms, preferably 1 to 10 carbon atoms, more preferably 1 to 5 carbon atoms;

k is 0 or 1;

$R^5$ is a branched or cyclic alkyl or alkoxy group having 3 to 40 carbon atoms, an aromatic or heteroaromatic ring system having 5 to 60 aromatic ring atoms, which may be substituted by one or more radicals $R^b$;

preferably said cyclic alkyl or alkoxy group is a cyclic alkyl or alkoxy group having 3 to 40 carbon atoms, which may in each case be substituted by one or more radicals $R^b$, where one or more non-adjacent $CH_2$ groups may be replaced by $R^bC{=}CR^b$, C≡C, $Si(R^b)_2$, $Ge(R^b)_2$, $Sn(R^b)_2$, C=O, C=S, C=Se, C—$NR^b$, P(=O)($R^b$), SO, $SO_2$, $NR^b$, OS, or $CONR^b$ and where one or more H atoms may be replaced by D, F, Cl, Br, I, CN or $NO_2$;

$R^b$ is at each occurrence, identically or differently, H, D, or an alkyl group having 1 to 20 carbon atoms, cyclic alkyl or alkoxy group having 3 to 40 carbon atoms, an aromatic ring system having 5 to 60 carbon ring atoms, or a hetero aromatic ring system having 5 to 60 carbon atoms, wherein H atoms may be replaced by D, F, Cl, Br, I; two or more adjacent substituents $R^b$ here may also form a mono- or polycyclic, aliphatic, aromatic or heteroaromatic ring system with one another; and $R^6$ is H or $CH_3$.

Particularly preferred examples of (meth)acrylate monomers to be used as matrix material in the composition according to this aspect of the invention are lauryl acrylate (LA), lauryl methacrylate (LMA), 4-tert-butylcyclohexyl acrylate (TBCH), trimethylolpropane triacrylate (TMPTA), cyclohexyl methacrylate (CHMA), tripropyleneglycol diacrylate (TPGDA), 1,6-hexanediol dimethacrylate (HDDMA), isobornyl acrylate (IBA), isobornyl methacrylate (IBMA), 1,9-nonanediol diacrylate (NDDA), or any combination of one or more thereof.

Further preferably, the (meth)acrylate monomer represented by the chemical formula (VII) used as a matrix material has a viscosity of 25 cP or less at 25° C., preferably in the range from 1 to 25 cP, more preferably from 2 to 20 cP, even more preferably from 2 to 10 cP, and/or a boiling point (B.P.) of 180° C. or more, preferably it is in the range from 180° C. to 350° C., more preferably from 250° C. to 350° C.

According to the present invention, said viscosity can be measured by vibration type viscometer VM-10A (SEKONIC) at room temperature. https://www.sekonic-.co.jp/english/product/viscometer/vm/vm_series.html In a further preferred embodiment of the composition according to this aspect of the invention, the compound of chemical formula (I) represents a compound of the chemical formula (III) as defined herein (III)

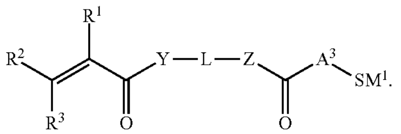

In an even more preferred embodiment of the composition according to this aspect of the invention, in chemical formula (III)

L is selected from chemical formula (II)

(II)

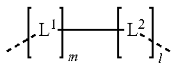

wherein $L^1$ is

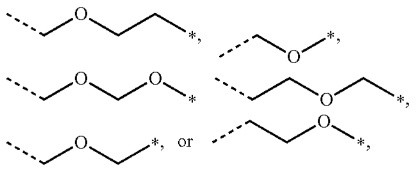

preferably

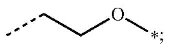

$L^2$ is

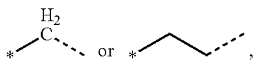

preferably

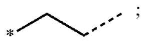

wherein a dashed line indicates a bond to the remainder of the compound (that is, a bond from group L, $L^1$ and $L^2$ to group Y or to group Z) and the symbol "*" marks the bond between groups $L^1$ and $L^2$, and wherein each of $L^1$ and $L^2$ may be substituted by one or more groups $R^a$, where one or more $CH_2$ groups of $L^1$ and $L^2$ may be replaced by $—R^aC{=}CR^a—$, $—C{\equiv}C—$, $Si(R^a)_2$, $Ge(R^a)_2$, $Sn(R^a)_2$, C═O, C═S, C═Se, $C{=}NR^a$, $P({=}O)(R^a)$, SO, $SO_2$, $NR^a$, or $—C({=}O)NR^a—$, and where one or more H atoms in $L^1$ and $L^2$ may be replaced by D, F, Cl, Br, I, CN or $NO_2$; and $M^1$ is H;

and where indices m and l and symbol $R^a$ are as defined herein.

Further preferably, in the composition according to this aspect of the invention $L^1$ is

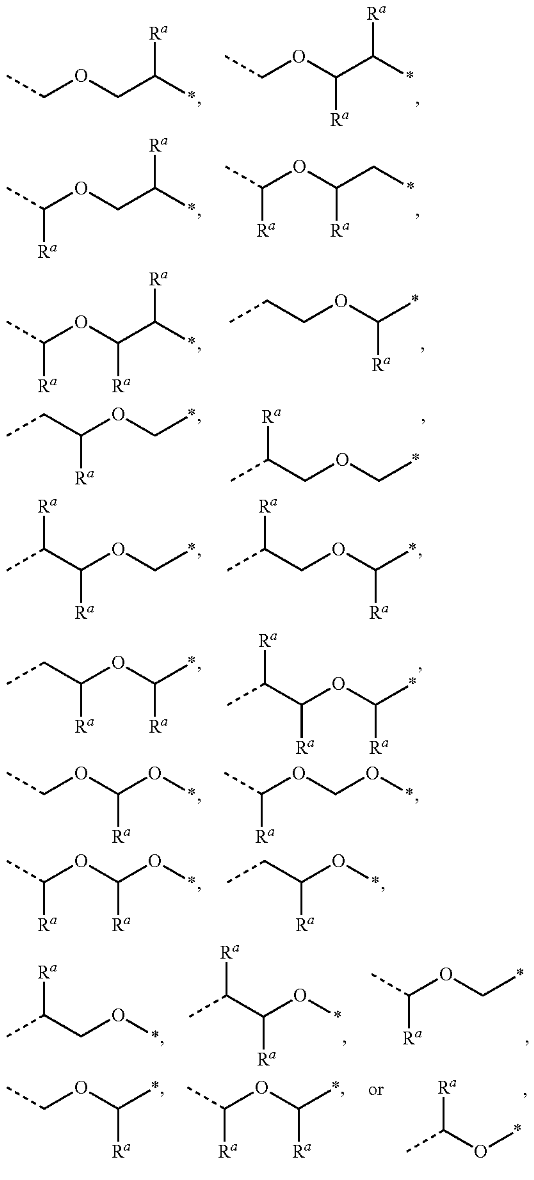

preferably, $L^1$ is

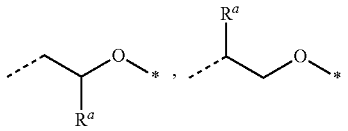

or

-continued

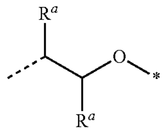

;

and $L^2$ is

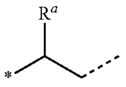

or

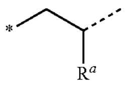

, preferably

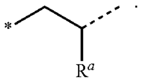

.

In a particular preferred embodiment of the composition according to this aspect of the invention, the compound of chemical formula (I) or (III) represents a compound of chemical formula (V-a) or (V-b), preferably (V-a), (V-a)

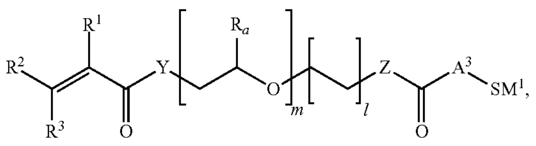

(V-b)

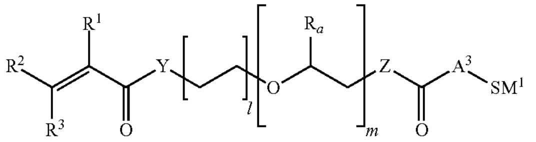

wherein the symbols and indices are as defined herein, and Z is NH or O and $M^1$ is H.

Particularly preferred examples of the compound of chemical formula (V-a) which may be comprised in the composition according to this aspect of the invention are represented by chemical formulae (V-1) to (V-6) as defined above, wherein $M^1$ is H.

It is further preferred according to this aspect of the invention that the composition comprises the compound represented by chemical formula (I) in an amount of 1 to 50 wt. %, more preferably 5 to 40 wt. % and even more preferably 10 to 30 wt. %, based on the total weight of the composition.

Further preferably, the composition according to this aspect of the invention comprises the semiconducting light emitting nanoparticles (inorganic part of the nanoparticles only) in an amount of 1 to 50 wt. %, more preferably 20 to 45 wt. % and even more preferably 25 to 40 wt. %, based on the total weight of the composition.

It has surprisingly been found by the present inventors that when a bifunctional, polymerizable acrylate-based compound of chemical formula (I) as defined herein is used as an additive added directly to a composition which comprises semiconducting light emitting nanoparticles and at least one further functional material, preferably a host or matrix material, which is more preferably selected from (meth) acrylate monomers or polymers, as defined in relation to this aspect of the present invention, an improved stability and improved optical properties, such as high luminous efficiency, of the nanoparticles can be achieved, even after film curing and/or film heating.

Formulation

For the processing of semiconducting light emitting nanoparticle, compounds or compositions according to the invention from a liquid phase, for example by spin coating or by printing methods, formulations comprising the nanoparticles, compounds or compositions of the invention are required. These formulations may, for example, be solutions, dispersions or emulsions.

The present invention thus further relates to a formulation comprising a semiconducting light emitting nanoparticle according to the present invention as defined herein, or a compound or a composition according to the present invention as defined herein, and at least one solvent.

Preferably the at least one solvent is selected from the group consisting of esters such as, PGMEA (propylene glycol methyl ether acetate), ethyl acetate, butyl acetate, amyl acetate, ethylene carbonate, methoxy propyl acetate; ketones such as methyl ethyl ketone (MEK), methyl isobutyl ketone, cyclohexanone; glycols such as ethylene glycol, propylene glycol, butylene glycol, diethylene glycol, triethylene glycol, glycol ethers, hexylene glycol; ethers such as, diethyl ethers, tetrahydofuran, alcohols such as, methanol, ethanol, isopropanol, and butanol; or aromatic, halogenated and aliphatic hydrocarbons, such as toluene, xylene, chloroform, dichloromethane and heptane. It may be further preferable to use mixtures of two or more solvents.

The amount of the solvent in the formulation can be freely controlled depending on the method of coating. For example, if the formulation is to be spray-coated, it can contain the solvent in an amount of 90 wt. % or more. Further, if a slit-coating method, which is often adopted in coating a large substrate, is to be carried out, the content of the solvent is normally 60 wt. % or more, preferably 70 wt. % or more.

The way in which such formulations can be prepared is known to those skilled in the art and is described, for example, in WO 2002/072714, WO 2003/019694 and the literature cited therein.

Use

The present invention further relates to the use of a semiconducting light emitting nanoparticle according to the present invention as defined herein, or a composition or formulation according to the present invention as defined herein, in an electronic device, optical device or in a biomedical device.

In another aspect, the present invention further relates to the use of a compound represented by chemical formula (I) as defined herein, or a compound represented by chemical formula (III) as defined herein, as an additive in a composition which comprises a semiconducting light emitting nanoparticle having at least a core and optionally one or more shell layers, and at least one further functional material, which is preferably selected from the group consisting of organic light emitting materials, inorganic light emitting materials, charge transporting materials, host or matrix materials, optically transparent polymers, anti-oxidants or stabilizers, radical quenchers, photo initiators or polymerization initiators, wetting and dispersing agents, scattering particles, reflective index adjusting materials, developer-dissolution promoters, scum removers, adhesion enhancers, polymerization inhibitors, defoaming agents, surfactants and sensitizers. More preferably, the at least one further functional material is a host or matrix material, which is even more preferably selected from (meth)acrylate monomers or polymers.

The definitions and preferred examples of the further functional material mentioned above in relation to the composition according to the present invention are likewise preferred in this use. The (meth)acrylate monomer is particularly preferably represented by chemical formula (VII) as define above.

As an inorganic part of the semiconducting light emitting nanoparticle according to the use according to this aspect of the present invention, a wide variety of publicly known semiconducting light emitting nanoparticles can be used as desired. In particular, a type of shape of the semiconducting light emitting nanoparticle and its core and optional one or more shell layers may be as defined above in relation to the semiconducting light emitting nanoparticle of the present invention.

In addition, the outermost surface of the core or the shell layer(s) of the semiconducting light emitting nanoparticle comprised in the composition according to this aspect of the present invention may be over-coated with different types of compounds as defined above in relation to the semiconducting light emitting nanoparticle of the present invention.

In a preferred embodiment of the use according to this aspect of the invention, the compound used is a compound of chemical formula (III) as defined herein (III)

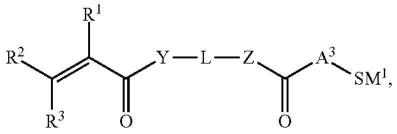

wherein

L is selected from chemical formula (II)

(II)

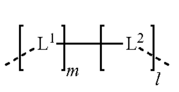

wherein $L^1$ is

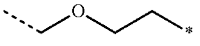 , 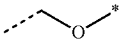 , 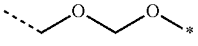

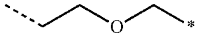 , 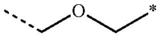 , or

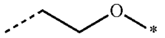 , preferably

;

$L^2$ is

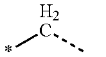 or 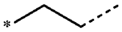 , preferably

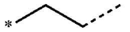 ;

wherein a dashed line indicates a bond to the remainder of the compound (that is, a bond from group L, $L^1$ and $L^2$ to group Y or to group Z) and the symbol "*" marks the bond between groups $L^1$ and $L^2$, and wherein each of $L^1$ and $L^2$ may be substituted by one or more groups $R^a$, where one or more $CH_2$ groups of $L^1$ and $L^2$ may be replaced by —$R^aC$═$CR^a$—, —C≡C—, $Si(R^a)_2$, $Ge(R^a)_2$, $Sn(R^a)_2$, C═O, C═S, C═Se, C═$NR^a$, P(═O)($R^a$), SO, $SO_2$, $NR^a$, or —C(═O)$NR^a$—, and where one or more H atoms in $L^1$ and $L^2$ may be replaced by D, F, Cl, Br, I, CN or $NO_2$; and $M^1$ is H;

and where indices m and l and symbol $R^a$ are as defined above in relation to the compound of the present invention.

In a further preferred embodiment of the use according to this aspect of the invention, $L^1$ is

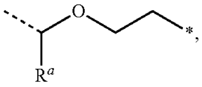 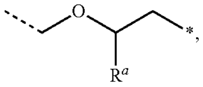

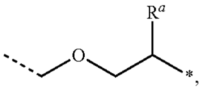 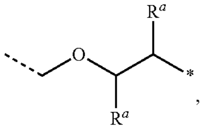

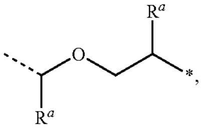 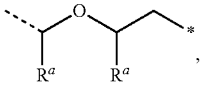

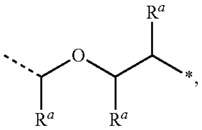 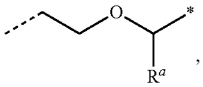

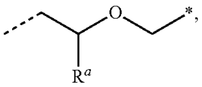 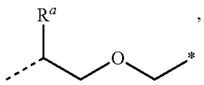

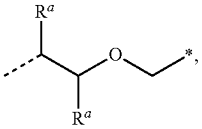 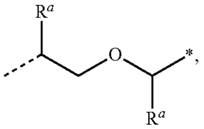

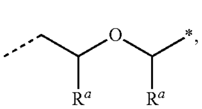 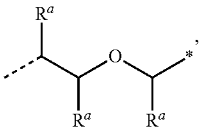

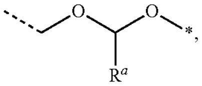 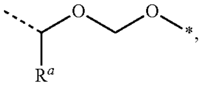

-continued

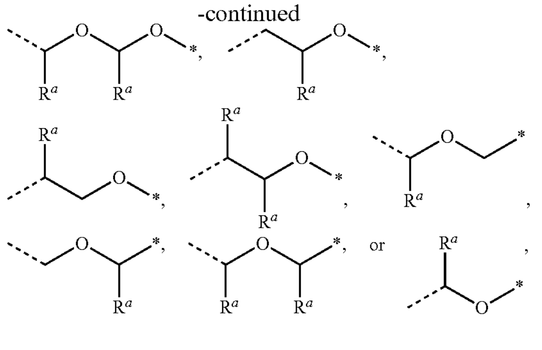

or preferably, $L^1$ is

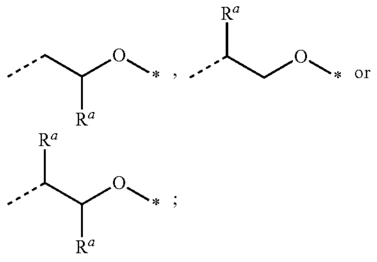

or ;

and $L^2$ is

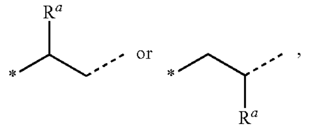

or , preferably

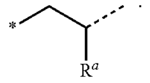

In an even further preferred embodiment of the use according to this aspect of the invention, the compound of chemical formula (I) or (III) represents a compound of chemical formula (V-a) or (V-b), preferably (V-a), (V-a)

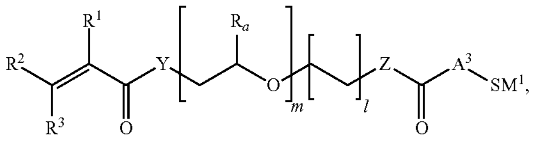

(V-b)

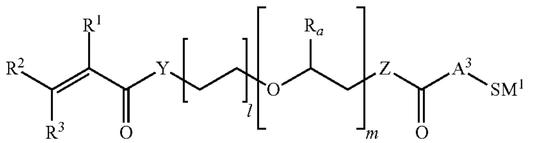

wherein the symbols and indices are as defined above in relation to the compound of the present invention, and Z is NH or O and $M^1$ is H.

Particularly preferred examples of the compound of chemical formula (V-a) used according to this aspect of the invention are represented by chemical formulae (V-1) to (V-6) as defined above, wherein $M^1$ is H.

Optical Medium

The present invention further relates to an optical medium comprising a semiconducting light emitting nanoparticle according to the present invention as defined herein, or a composition or formulation according to the present invention as defined herein.

In a preferred embodiment, the optical medium is an optical film, for example, a color filter, color conversion film, remote phosphor tape, or another film or filter, more preferably it is a color conversion film, even more preferably, it is a pixelated color conversion film.

Optical Device

The present invention further relates to an optical device comprising a semiconducting light emitting nanoparticle according to the present invention as defined herein, or a composition or formulation according to the present invention as defined herein, or said optical medium of the present invention.

In a preferred embodiment of the present invention, the optical device is a liquid crystal display, an Organic Light Emitting Diode (OLED), a backlight unit for displays, a Light Emitting Diode (LED), a Micro Electro Mechanical Systems (MEMS), an electro wetting display, an electroluminescent quantum dot light emitting diode (EL-Q-LED, like described in US 2016/248029 A2, EP 2221355 A1) or an electrophoretic display, a lighting device, and/or a solar cell.

Process

The present invention furthermore provides for a simple process for the preparation of an optical device of the present invention, said process comprising the following steps a) to c), preferably in this sequence:

a) preparing a mixture by mixing a semiconducting light emitting nanoparticle having at least a core and optionally one or more shell layers, at least one further functional material, a compound represented by chemical formula (I) as defined herein and optionally at least one solvent (I)

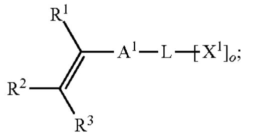

b) providing the mixture onto a substrate;

c) subjecting the mixture obtained to a photo irradiation having a peak light wavelength in the range from 300 to 650 nm, preferably in the range from 320 to 520 nm, more preferably from 350 nm to 500 nm, even more preferably from 360 nm to 470 nm.

The preferred embodiments of the compound, symbols and indices of chemical formula (I) mentioned above in relation to the semiconducting light emitting nanoparticle according to the present invention are likewise preferred in this process.

In particular, preference is given to the compounds represented by chemical formula (III) as defined above, and to the compounds represented by chemical formulae (IV), (V-a) and (V-b) as defined above. Further particular preference is given to the embodiments represented by chemical formulae (IV-1) to (IV-6) and (V-1) to (V-6) as defined above.

According to an embodiment of the process for the preparation of an optical device according to the present invention, the compound represented by chemical formula (I) as defined herein is first mixed with said semiconducting light emitting nanoparticle, before mixing with the at least one further functional material and the optional at least one solvent.

According to another embodiment of the process for the preparation of an optical device according to the present invention, the semiconducting light emitting nanoparticle, the at least one further functional material and the optional at least one solvent are first mixed, before the compound represented by chemical formula (I) as defined herein is added and mixed with the obtained mixture.

Preferably, according to this embodiment of the process of to the invention the compound represented by chemical formula (I) is added in amount of 1 to 50 wt. %, more preferably 5 to 40 wt. % and even more preferably 10 to 30 wt. %, based on the total weight of the composition (without the solvent).

The at least one further functional material is preferably selected from the group consisting of organic light emitting materials, inorganic light emitting materials, charge transporting materials, host or matrix materials, optically transparent polymers, anti-oxidants or stabilizers, radical quenchers, photo initiators or polymerization initiators, wetting and dispersing agents, scattering particles, reflective index adjusting materials, developer-dissolution promoters, scum removers, adhesion enhancers, polymerization inhibitors, defoaming agents, surfactants and sensitizers. Preferably, the at least one further functional material is a host or matrix material, which is more preferably selected from (meth) acrylate monomers or polymers. (Meth)acrylate monomers as represented by chemical formula (VII) defined above are especially preferred in the process for preparing the optical device according to the present invention.

The preferred examples of the further functional materials as defined above in the section “Composition” are likewise preferred in this connection.

The at least one solvent optionally added according to the process for the preparation of an optical device according to the present invention is selected from the group consisting of esters such as, PGMEA (propylene glycol methyl ether acetate), ethyl acetate, butyl acetate, amyl acetate, ethylene carbonate, methoxy propyl acetate; ketones such as methyl ethyl ketone (MEK), methyl isobutyl ketone, cyclohexanone; glycols such as ethylene glycol, propylene glycol, butylene glycol, diethylene glycol, triethylene glycol, glycol ethers, hexylene glycol; ethers such as, diethyl ethers, tetrahydofuran, alcohols such as, methanol, ethanol, isopropanol, and butanol; or aromatic, halogenated and aliphatic hydrocarbons, such as toluene, xylene, chloroform, dichloromethane and heptane.

The light source for light irradiation in step (c) is selected from one or more of artificial light sources, and is preferably selected from a light emitting diode, an organic light emitting diode, a cold cathode fluorescent lamp, or a laser device.

The mixture obtained in step a) may be sealed in a transparent container, such as a vial.

In a preferred embodiment of the present invention, step a), b) and/or c) are carried out in an inert condition, such as nitrogen ($N_2$) or argon (Ar) atmosphere. More preferably, all of steps a) and b) and optionally step c) are carried out in said inert condition.

The irradiation intensity (that is, total luminous flux incident on a surface) of the light irradiated in step c) is preferably in the range from 0.25 to 100 $mW/cm^2$, preferably it is in the range from 0.5 to 50 $mW/cm^2$.

According to the present invention, to provide the photosensitive composition onto the substrate according to step a), any type of publicly known coating method can be used preferably. For examples, immersion coating, gravure coating, roll coating, bar coating, brush coating, spray coating, doctor coating, flow coating, spin coating, and slit coating.

The substrate is not particularly limited, and can be properly selected from, for example, a silicon substrate, a glass substrate, or a polymer film, each of which may be flexible, semi-rigid or rigid. Preferably, a transparent substrate is employed. Publically known transparent substrate suitable for optical devices can be used as desired.

Preferably, as a transparent substrate, a transparent polymer substrate, glass substrate, thin glass substrate stacked on a transparent polymer film, transparent metal oxides (for example, oxide silicone, oxide aluminum, oxide titanium), can be used.

Before the step of photo irradiation and after the step of providing the mixture onto the substrate, a heating step (preheating treatment) may optionally be carried out according to necessity. The preheating is preferably carried out at a temperature of 50 to 150° C., more preferably 90 to 150° C., for 10 seconds to 30 minutes, preferably 10 seconds to 5 minutes, using a hotplate, an oven, a furnace or the like.

Further, after the step of photo irradiation a post-irradiation heating step may optionally be carried according to necessity. The post-irradiation heating is preferably carried out at a temperature of 40 to 150° C., more preferably 60 to 120° C., for 10 seconds to 10 minutes, more preferably 20 seconds to 5 minutes, using a hotplate, an oven, a furnace or the like.

In a further preferred embodiment of the present invention, the step c) is carried out at a temperature below 70° C., preferably in the range from 60° C. to 0° C., more preferably in the range from 50° C. to 20° C., and/or for a time period of 1 second to 1 hour, preferably 10 seconds to 30 min, and more preferably 1 min to 15 min.

PREFERABLE EMBODIMENTS

1. A semiconducting light emitting nanoparticle comprising a core, optionally one or more shell layers, and a compound represented by chemical formula (I)

(I)

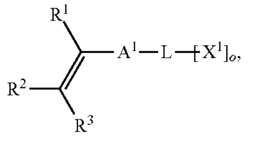

wherein is 1, 2 or 3, preferably 1;

$R^1$ is H, D, CN, a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by $—R^aC═CR^a—$, $—C≡C—$, $Si(R^a)_2$, $Ge(R^a)_2$, $Sn(R^a)_2$, C═O, C═S, C═Se, $C═NR^a$, $P(═O)(R^a)$, SO, $SO_2$, —O—, $NR^a$, —C(═O)O—, or $—C(═O)NR^a—$, and where one or more H atoms may be replaced by D, F, Cl, Br, I, CN or $NO_2$; an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms may be replaced by D, F, Cl, Br, I, CN or $NO_2$;

$R^2$, $R^3$ are, independently of each other, H, D, CN, a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by $—R^aC═CR^a—$, —C≡C—, $Si(R^a)_2$, $Ge(R^a)_2$, $Sn(R^a)_2$, C═O, C═S, C═Se, $C═NR^a$, $P(═O)(R^a)$, SO, $SO_2$, —O—, $NR^a$, —C(═O)O—, or $—C(═O)NR^a—$, and where one or more H atoms may be replaced by D, F, Cl, Br, I, CN or $NO_2$;

or an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms may be replaced by D, F, Cl, Br, I, CN or $NO_2$;

$A^1$ is

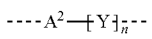 or 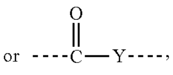, with n=0 or 1;

Y is O, NH, S, preferably O or NH;

$A^2$ is a divalent group selected from an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms of the aromatic or heteroaromatic ring system may be replaced by D, F, Cl, Br, I, CN, $NO_2$;

$R^a$ is at each occurrence, identically or differently, H, D, a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms; a straight-chain alkenyl or alkynyl group having 2 to 40 carbon atoms, preferably 2 to 24 carbon atoms, more preferably 2 to 12 carbon atoms; a branched alkenyl group or alkynyl group having 3 to 40 carbon atoms, preferably 3 to 24 carbon atoms, more preferably 3 to 12 carbon atoms; an aromatic or heteroaromatic ring system having 5 to 40 aromatic ring atoms, preferably 5 to 25 aromatic ring atoms, more preferably 5 to 18 aromatic ring atoms, wherein in each of the above-mentioned groups one or more H atoms may be replaced by D, F, Cl, Br, I, and where two or more adjacent substituents $R^a$ here may optionally form a mono- or polycyclic, aliphatic ring system with one another;

L is a divalent group selected from a straight-chain alkylene group having 1 to 40 carbon atoms, preferably 3 to 24 carbon atoms, more preferably 4 to 12 carbon atoms; a branched or cyclic alkylene group having 3 to 40 carbon atoms, preferably 4 to 24 carbon atoms, more preferably 5 to 12 carbon atoms; a straight-chain alkenylene or alkynylene group having 2 to 40 carbon atoms, preferably 3 to 24 carbon atoms, more preferably 4 to 12 carbon atoms; or a branched alkenylene group or alkynylene group having 3 to 40 carbon atoms, preferably 4 to 24 carbon atoms, more preferably 5 to 12 carbon atoms, each of which each may be substituted by one or more groups $R^a$, where in each case one or more $CH_2$ groups may be replaced by an arylene group or heteroarylene group having 5 to 40 aromatic ring atoms, preferably 5 to 25 aromatic ring atoms, more preferably 5 to 18 aromatic ring atoms, $Si(R^a)_2$, $Ge(R^a)_2$, $Sn(R^a)_2$, C═O, C═S, C═Se, $C═NR^a$, $P(═O)(R^a)$, SO, $SO_2$, —O—, $NR^a$, —C(═O)O—, or $—C(═O)NR^a—$, and where one or more H atoms may be replaced by D, F, Cl, Br, I, CN or $NO_2$; an aromatic or heteroaromatic ring system having 5 to 40 aromatic ring atoms, preferably 5 to 25 aromatic ring atoms, more preferably 5 to 18 aromatic ring atoms, an aralkylene group, a heteroaralkylene group, an alkylarylene group or an alkylheteroarylene group, each of which may be substituted by one or more groups $R^a$, and where in each case one or more H atoms may be replaced by D, F, Cl, Br, I, CN, $NO_2$; or a group represented by the following chemical formula (II)

(II)

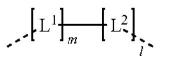 or 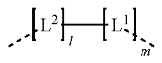

wherein m is an integer of 1 to 50, preferably 1 to 25, more preferably 2 to 20, and furthermore preferably 4 to 12;

l is an integer of 1 to 25, preferably 1 to 20, more preferably 1 to 12, and furthermore preferably 1 to 8;

$L^1$ is

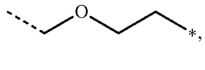, 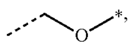,

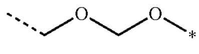, 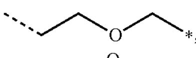,

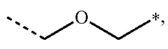, or 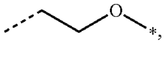, preferably

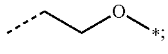;

$L^2$ is

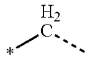

or

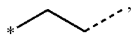

, preferably

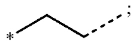

;

wherein a dashed line indicates a bond to the remainder of the compound and the symbol "*" marks the bond between groups $L^1$ and $L^2$, and wherein each of $L^1$ and $L^2$ may be substituted by one or more groups $R^a$, where one or more $CH_2$ groups of $L^1$ and $L^2$ may be replaced by $—R^aC═CR^a—$, —C≡C—, $Si(R^a)_2$, $Ge(R^a)_2$, $Sn(R^a)_2$, C═O, C═S, C═Se, $C═NR^a$, $P(═O)(R^a)$, SO, $SO_2$, $NR^a$, or $—C(═O)NR^a—$, and where one or more H atoms in $L^1$ and $L^2$ may be replaced by D, F, Cl, Br, I, CN or $NO_2$;

$X^1$ is, identically or differently on each occurrence, an anchor group preferably selected from $—COOM^1$, $—PO(OH)(OM^1)$, $—PO(OM^1)_2$, $—OC(S)SM^1$, $—NH_2$, $—NHR^a$, $—N(R^a)_2$, $—SO_3M^1$, $—SM^1$, $—Ar^1—SM^1$, $—OCO\text{-}A^3\text{-}SM^1$, $—COO\text{-}A^3\text{-}SM^1$, $—NCO\text{-}A^3\text{-}SM^1$, $SiOR^a$, or $—N(CS_2\ M^1)_2$;

$Ar^1$ is a divalent group selected from an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms of the aromatic or heteroaromatic ring system may be replaced by D, F, Cl, Br, I, CN, $NO_2$;

$A^3$ is a divalent group selected from a straight-chain alkylene group having 1 to 40 carbon atoms, preferably 1 to 25 carbon atoms, more preferably 1 to 15 carbon atoms; a branched or cyclic alkylene group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by, $Si(R^a)_2$, $Ge(R^a)_2$, $Sn(R^a)_2$, C═O, C═S, C═Se, $C═NR^a$, $P(═O)(R^a)$, SO, $SO_2$, —O—, $NR^a$, —C(═O)O—, or $—C(═O)NR^a—$, and where one or more H atoms may be replaced by D, F, Cl, Br, I, CN or $NO_2$; an aromatic or heteroaromatic ring system having 5 to 25 aromatic ring atoms, preferably 5 to 18 aromatic ring atoms, more preferably 5 to 12 aromatic ring atoms, each of which may be substituted by one or more groups $R^a$, and where one or more H atoms of the aromatic or heteroaromatic ring system may be replaced by D, F, Cl, Br, I, CN, $NO_2$;

$M^1$ denotes a hydrogen atom, or a metal cation selected from ½ $Mg^{2+}$, ½ $Cu^{2+}$, ½ $Zn^{2+}$, ½ $Pb^{2+}$, ½ $Sn^{2+}$, ½ $Cd^{2+}$, ⅓ $Bi^{3+}$ or ¼ $Sn^{4+}$, preferably a hydrogen atom, ½ $Mg^{2+}$, ½ $Cu^{2+}$, or ½ $Zn^{2+}$, more preferably a hydrogen atom.

2. Semiconducting light emitting nanoparticle according to embodiment 1, wherein in chemical formula (I)

$A^1$ is

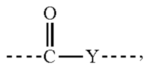

, where Y is as defined above.

3. Semiconducting light emitting nanoparticle according to embodiment 1 or 2, wherein in chemical formula (I)

$X^1$ is, identically or differently on each occurrence, selected from $—OC(S)SM^1$, $—SM^1$, $—Ar^1—SM^1$, $—OCO\text{-}A^3\text{-}SM^1$, $—COO\text{-}A^3\text{-}SM^1$, $—NCO\text{-}A^3\text{-}SM^1$, or $—N(CS_2\ M^1)_2$;

where $Ar^1$, $A^3$ and $M^1$ are as defined in embodiment 1.

4. Semiconducting light emitting nanoparticle according to any one of embodiments 1 to 3, wherein in chemical formula (I)

$A^1$ is

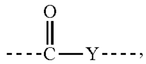

, and $X^1$ is, identically or differently on each occurrence, selected from $—OC(S)SM^1$, $—SM^1$, $—Ar^1—SM^1$, $—OCO\text{-}A^3\text{-}SM^1$, $—COO\text{-}A^3\text{-}SM^1$, $—NCO\text{-}A^3\text{-}SM^1$, or $—N(CS_2\ M^1)_2$;

where Y, $Ar^1$, $A^3$ and $M^1$ are as defined in claim 1.

5. Semiconducting light emitting nanoparticle according to any one of embodiments 1 to 4, wherein in chemical formula (I)

L is selected from a straight-chain alkylene group having 1 to 40 carbon atoms, preferably 3 to 24 carbon atoms, more preferably 4 to 12 carbon atoms; a branched or cyclic alkylene group having 3 to 40 carbon atoms, preferably 4 to 24 carbon atoms, more preferably 5 to 12 carbon atoms; a straight-chain alkenylene or alkynylene group having 2 to 40 carbon atoms, preferably 3 to 24 carbon atoms, more preferably 4 to 12 carbon atoms; or a branched alkenylene group or alkynylene group having 3 to 40 carbon atoms, preferably 4 to 24 carbon atoms, more preferably 5 to 12 carbon atoms, each of which each may be substituted by one or more groups $R^a$, where in each case one or more $CH_2$ groups may be replaced by an arylene group or heteroarylene group having 5 to 40 aromatic ring atoms, preferably 5 to 25 aromatic ring atoms, more preferably 5 to 18 aromatic ring atoms, $Si(R^a)_2$, $Ge(R^a)_2$, $Sn(R^a)_2$, C═O, C═S, C═Se, $C═NR^a$, $P(═O)(R^a)$, SO, $SO_2$, —O—, $NR^a$, —C(═O)O—, or $—C(═O)NR^a—$, and where one or more H atoms may be replaced by D, F, Cl, Br, I, CN or $NO_2$; or a group represented by chemical formula (II), (II)

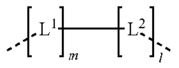

wherein $L^1$ is

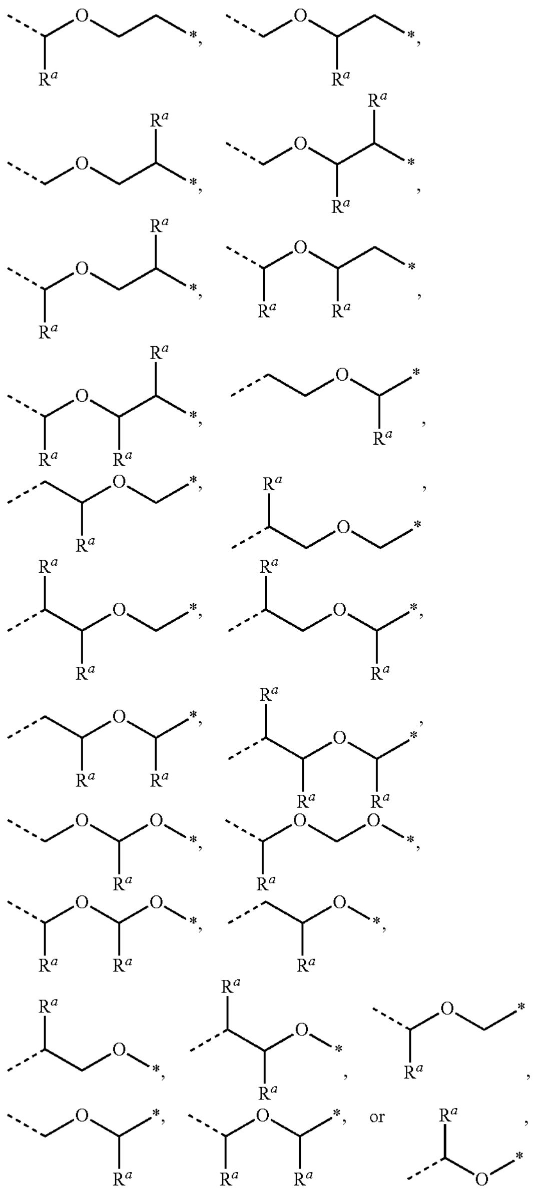

preferably, $L^1$ is

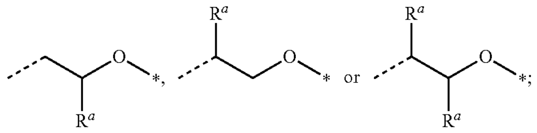

and $L^2$ is

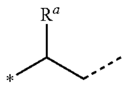
or
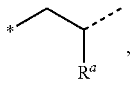
, preferably

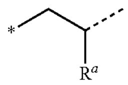

where m, l and $R^a$ are as defined in claim 1.

6. Semiconducting light emitting nanoparticle according to any one of embodiments 1 to 5, wherein in chemical formula (I)

$A^1$ is

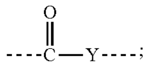

L is selected from a straight-chain alkylene group having 1 to 40 carbon atoms, preferably 3 to 24 carbon atoms, more preferably 4 to 12 carbon atoms; a branched or cyclic alkylene group having 3 to 40 carbon atoms, preferably 4 to 24 carbon atoms, more preferably 5 to 12 carbon atoms; a straight-chain alkenylene or alkynylene group having 2 to 40 carbon atoms, preferably 3 to 24 carbon atoms, more preferably 4 to 12 carbon atoms; or a branched alkenylene group or alkynylene group having 3 to 40 carbon atoms, preferably 4 to 24 carbon atoms, more preferably 5 to 12 carbon atoms, each of which each may be substituted by one or more groups $R^a$, where in each case one or more $CH_2$ groups may be replaced by an arylene group or heteroarylene group having 5 to 40 aromatic ring atoms, preferably 5 to 25 aromatic ring atoms, more preferably 5 to 18 aromatic ring atoms, $Si(R^a)_2$, $Ge(R^a)_2$, $Sn(R^a)_2$, C═O, C═S, C═Se, C═$NR^a$, P(═O)($R^a$), SO, $SO_2$, —O—, $NR^a$, —C(═O)O—, or —C(═O)$NR^a$—, and where one or more H atoms may be replaced by D, F, Cl, Br, I, CN or $NO_2$; or a group represented by chemical formula (II),

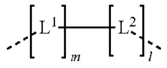
(II)

wherein $L^1$ is

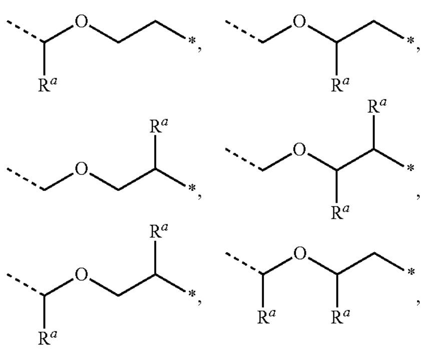

-continued

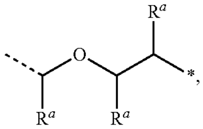, 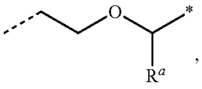, 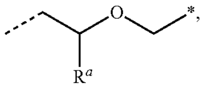, 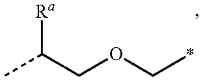, 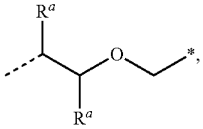, 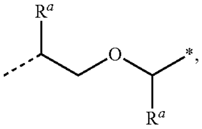, 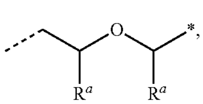, 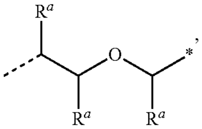, 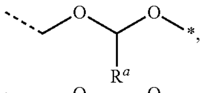, 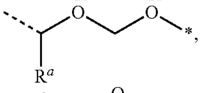, 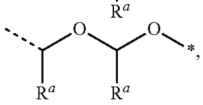, 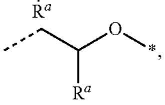, 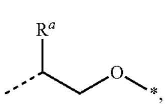, 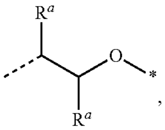, 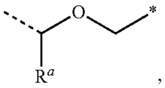, 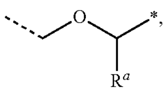, 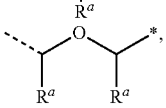, or 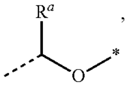, preferably, $L^1$ is

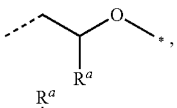, 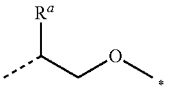 or 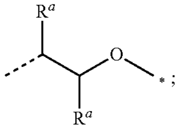;

$L^2$ is

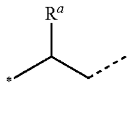 or 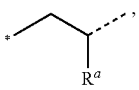, preferably

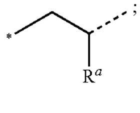;

and $X^1$ is, identically or differently on each occurrence, selected from —OC(S)$SM^1$, —$SM^1$, —$Ar^1$—$SM^1$, —OCO-$A^3$-$SM^1$, —NCO-$A^3$-$SM^1$, —COO-$A^3$-$SM^1$, or —N($CS_2$ $M^1$)$_2$;

where m, l, Y, $R^a$, $Ar^1$, $A^3$ and $M^1$ are as defined in claim 1.

7. Semiconducting light emitting nanoparticle according to any one of embodiments 1 to 6, wherein the compound of chemical formula (I) represents a compound of the following chemical formula (III)

(III)

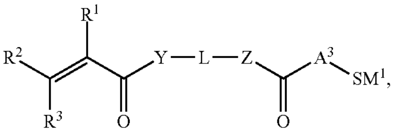

wherein the symbols occurring are as defined in any one of claims 1 to 6, and wherein Z is NH or O.

8. Semiconducting light emitting nanoparticle according to any one of embodiments 1 to 7, wherein the compound of chemical formula (I) represents a compound of the following chemical formulae (IV), (V-a) or (V-b)

(IV)

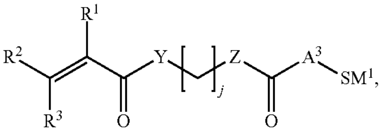

(V-a)

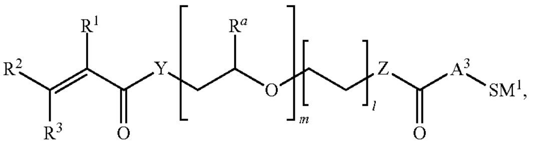

(V-b)

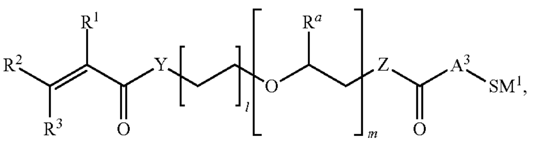

wherein the symbols and indices occurring are as defined in any one of embodiments 1 to 7, and j is an integer of 1 to 40, preferably 3 to 24, more preferably 4 to 12.

9. Semiconducting light emitting nanoparticle according to any one of embodiments 1 to 8, wherein the compound of chemical formula (I) represents a compound of one of the following chemical formulae (IV-1) to (IV-6) and (V-1) to (V-6)

(IV-1)

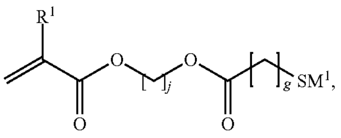

-continued (IV-2)

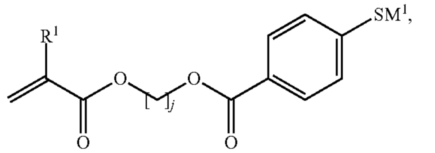

(IV-3)

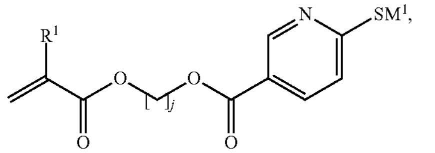

(IV-4)

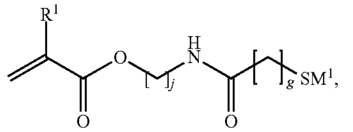

(IV-5)

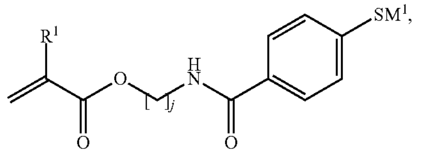

(IV-6)

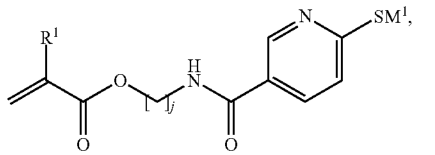

(V-1)

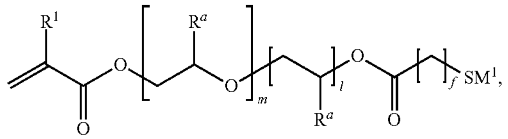

(V-2)

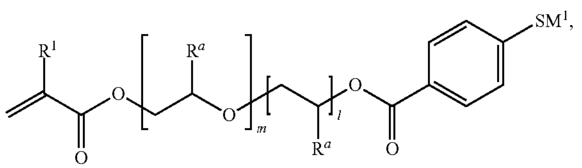

(V-3)

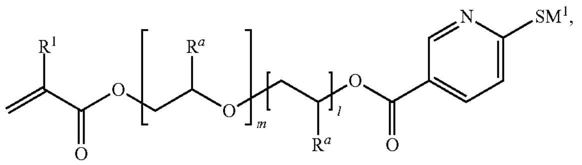

(V-4)

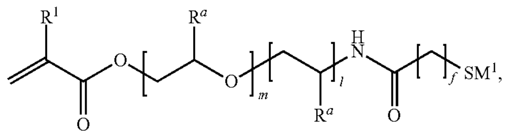

-continued (V-5)

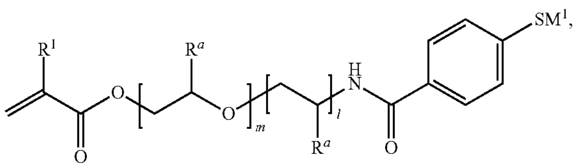

(V-6)

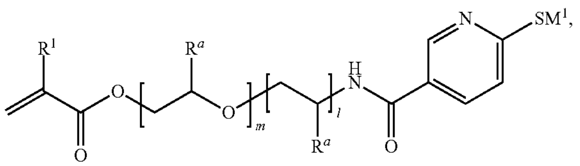

wherein the symbols and indices occurring have the meaning as in any one of embodiments 1 to 8, and wherein indices g and f are identically or differently an integer of 1 to 40, preferably 3 to 24, more preferably 4 to 12.

10. Semiconducting light emitting nanoparticle according to any one of embodiments 1 to 9, wherein the compound of chemical formula (I) has a molecular weight in the range of 150 to 2000 Da, more preferably 150 to 1500 Da, and even more preferably 200 to 1000 Da.

11. Compound represented by general formula (III)

(III)

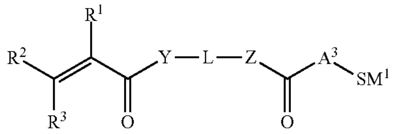

wherein

Y is O, NH or S, preferably O or NH;

Z is O or NH;

$R^1$ is H, D, CN a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by $-R^aC{=}CR^a-$, $-C{\equiv}C-$, $Si(R^a)_2$, $Ge(R^a)_2$, $Sn(R^a)_2$, $C{=}O$, $C{=}S$, $C{=}Se$, $C{=}NR^a$, $P({=}O)(R^a)$, SO, $SO_2$, $-O-$, $NR^a$, $-C({=}O)O-$, or $-C({=}O)NR^a-$, and where one or more H atoms may be replaced by D, F, Cl, Br, I, CN or $NO_2$; an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms may be replaced by D, F, Cl, Br, I, CN or $NO_2$;

$R^2$, $R^3$ are, independently of each other, H, D, CN, a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by —$R^aC$═$CR^a$—, —C≡C—, $Si(R^a)_2$, $Ge(R^a)_2$, $Sn(R^a)_2$, C═O, C═S, C═Se, C═$NR^a$, P(═O)($R^a$), SO, $SO_2$, —O—, $NR^a$, —C(═O)O—, or —C(═O)$NR^a$—, and where one or more H atoms may be replaced by D, F, Cl, Br, I, CN or $NO_2$;

or an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms may be replaced by D, F, Cl, Br, I, CN or $NO_2$;

$R^a$ is at each occurrence, identically or differently, H, D, a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms; a straight-chain alkenyl or alkynyl group having 2 to 40 carbon atoms, preferably 2 to 24 carbon atoms, more preferably 2 to 12 carbon atoms; a branched alkenyl group or alkynyl group having 3 to 40 carbon atoms, preferably 3 to 24 carbon atoms, more preferably 3 to 12 carbon atoms; an aromatic or heteroaromatic ring system having 5 to 40 aromatic ring atoms, preferably 5 to 25 aromatic ring atoms, more preferably 5 to 18 aromatic ring atoms, wherein in each of the above-mentioned groups one or more H atoms may be replaced by D, F, Cl, Br, I, and where two or more adjacent substituents $R^a$ here may optionally form a mono- or polycyclic, aliphatic ring system with one another;

L is a divalent group selected from a straight-chain alkylene group having 1 to 40 carbon atoms, preferably 3 to 24 carbon atoms, more preferably 4 to 12 carbon atoms; a branched or cyclic alkylene group having 3 to 40 carbon atoms, preferably 4 to 24 carbon atoms, more preferably 5 to 12 carbon atoms; a straight-chain alkenylene or alkynylene group having 2 to 40 carbon atoms, preferably 3 to 24 carbon atoms, more preferably 4 to 12 carbon atoms; or a branched alkenylene group or alkynylene group having 3 to 40 carbon atoms, preferably 4 to 24 carbon atoms, more preferably 5 to 12 carbon atoms, each of which each may be substituted by one or more groups $R^a$, where in each case one or more $CH_2$ groups may be replaced by an arylene group or heteroarylene group having 5 to 40 aromatic ring atoms, preferably 5 to 25 aromatic ring atoms, more preferably 5 to 18 aromatic ring atoms, $Si(R^a)_2$, $Ge(R^a)_2$, $Sn(R^a)_2$, C═O, C═S, C═Se, C═$NR^a$, P(═O)($R^a$), SO, $SO_2$, —O—, $NR^a$, —C(═O)O—, or —C(═O)$NR^a$—, and where one or more H atoms may be replaced by D, F, Cl, Br, I, CN or $NO_2$; an aromatic or heteroaromatic ring system having 5 to 40 aromatic ring atoms, preferably 5 to 25 aromatic ring atoms, more preferably 5 to 18 aromatic ring atoms, an aralkylene group, a heteroaralkylene group, an alkylarylene group or an alkylheteroarylene group, each of which may be substituted by one or more groups $R^a$, and where in each case one or more H atoms may be replaced by D, F, Cl, Br, I, CN, $NO_2$; or a group represented by the following chemical formula (II)

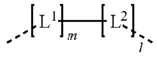 or 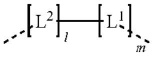

(II)

wherein m is an integer of 1 to 50, preferably 1 to 25, more preferably 2 to 20, and furthermore preferably 4 to 12;

l is an integer of 1 to 25, preferably 1 to 20, more preferably 1 to 12, and furthermore preferably 1 to 8;

$L^1$ is

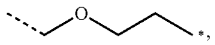 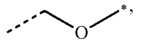

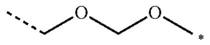 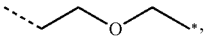

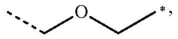 or 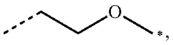

preferably

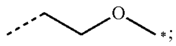

$L^2$ is

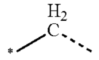 or 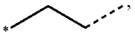

preferably

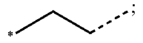

wherein a dashed line indicates a bond to the remainder of the compound and the symbol "*" marks the bond between groups $L^1$ and $L^2$, and wherein each of $L^1$ and $L^2$ may be substituted by one or more groups $R^a$, where one or more $CH_2$ groups of $L^1$ and $L^2$ may be replaced by —$R^aC$═$CR^a$—, —C≡C—, $Si(R^a)_2$, $Ge(R^a)_2$, $Sn(R^a)_2$, C═O, C═S, C═Se, C═$NR^a$, P(═O)($R^a$), SO, $SO_2$, $NR^a$, or —C(═O)$NR^a$—, and where one or more H atoms in $L^1$ and $L^2$ may be replaced by D, F, Cl, Br, I, CN or $NO_2$;

$A^3$ is a divalent group selected from a straight-chain alkylene group having 1 to 40 carbon atoms, preferably 1 to 25 carbon atoms, more preferably 1 to 15 carbon atoms; a branched or cyclic alkylene group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by, $Si(R^a)_2$, $Ge(R^a)_2$, $Sn(R^a)_2$, C═O, C═S, C═Se, C═$NR^a$, P(═O)($R^a$), SO, $SO_2$, —O—, $NR^a$, —C(═O)O—, or —C(═O)$NR^a$—, and where one or more H atoms may be replaced by D, F, Cl, Br, I, CN or $NO_2$; an aromatic or heteroaromatic ring system having 5 to 25 aromatic ring atoms, preferably 5 to 18 aromatic ring atoms, more preferably 5 to 12 aromatic ring atoms, each of which may be substituted by one or more groups $R^a$, and where one or more H atoms of the aromatic or heteroaromatic ring system may be replaced by D, F, Cl, Br, I, CN, $NO_2$; and $M^1$ denotes a hydrogen atom, or a metal cation selected from ½ $Mg^{2+}$, ½ $Cu^{2+}$, ½ $Zn^{2+}$, ½ $Pb^{2+}$, ½ $Sn^{2+}$, ½ $Cd^{2+}$, ⅓ $Bi^{3+}$ or ¼ $Sn^{4+}$, preferably a hydrogen atom, ½ $Mg^{2+}$, ½ $Cu^{2+}$, or ½ $Zn^{2+}$, more preferably a hydrogen atom.

12. Compound according to embodiment 11, which is a compound of one of the following chemical formulae (IV), (V-a) or (V-b)

(IV)

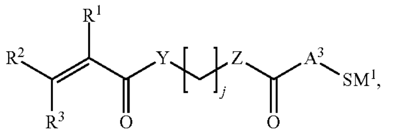

(V-a)

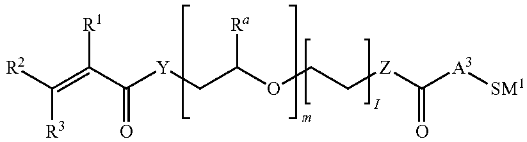

(V-b)

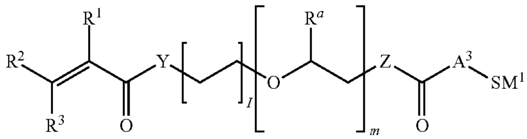

wherein the symbols and indices are as defined in claim 11 and j is an integer of 1 to 40, preferably 3 to 24, more preferably 4 to 12.

13. Composition comprising a nanoparticle according to any one of embodiments 1 to 10, and at least one further functional material, which is preferably selected from the group consisting of organic light emitting materials, inorganic light emitting materials, charge transporting materials, host or matrix materials, optically transparent polymers, anti-oxidants or stabilizers, radical quenchers, photo initiators or polymerization initiators, wetting and dispersing agents, scattering particles, reflective index adjusting materials, developer-dissolution promoters, scum removers, adhesion enhancers, polymerization inhibitors, defoaming agents, surfactants and sensitizers.

14. Composition comprising a compound according to embodiment 11 or 12, and at least one further functional material, which is preferably selected from the group consisting of organic light emitting materials, inorganic light emitting materials, charge transporting materials, host or matrix materials, optically transparent polymers, anti-oxidants or stabilizers, radical quenchers, photo initiators or polymerization initiators, wetting and dispersing agents, scattering particles, reflective index adjusting materials, developer-dissolution promoters, scum removers, adhesion enhancers, polymerization inhibitors, defoaming agents, surfactants and sensitizers.

15. Composition comprising a semiconducting light emitting nanoparticle having at least a core, and optionally one or more shell layers, a compound represented by chemical formula (I)

(I)

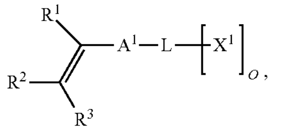

wherein is 1, 2 or 3, preferably 1;

$R^1$ is H, D, CN a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by —$R^aC$═$CR^a$—, —C≡C—, $Si(R^a)_2$, $Ge(R^a)_2$, $Sn(R^a)_2$, C═O, C═S, C═Se, C═$NR^a$, P(═O)($R^a$), SO, $SO_2$, —O—, $NR^a$, —C(═O)O—, or —C(═O)$NR^a$—, and where one or more H atoms may be replaced by D, F, Cl, Br, I, CN or $NO_2$; an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms may be replaced by D, F, Cl, Br, I, CN or $NO_2$;

$R^2$, $R^3$ are, independently of each other, H, D, CN, a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by —$R^aC$═$CR^a$—, —C≡C—, $Si(R^a)_2$, $Ge(R^a)_2$, $Sn(R^a)_2$, C═O, C═S, C═Se, C═$NR^a$, P(═O)($R^a$), SO, $SO_2$, —O—, $NR^a$, —C(═O)O—, or —C(═O)$NR^a$—, and where one or more H atoms may be replaced by D, F, Cl, Br, I, CN or $NO_2$; or an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms may be replaced by D, F, Cl, Br, I, CN or $NO_2$;

$A^1$ is

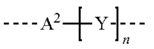

or

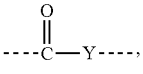

with n=0 or 1;

Y is O, NH, S, preferably O or NH;

$A^2$ is a divalent group selected from an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms of the aromatic or heteroaromatic ring system may be replaced by D, F, Cl, Br, I, CN, $NO_2$;

$R^a$ is at each occurrence, identically or differently, H, D, a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms; a straight-chain alkenyl or alkynyl group having 2 to 40 carbon atoms, preferably 2 to 24 carbon atoms, more preferably 2 to 12 carbon atoms; a branched alkenyl group or alkynyl group having 3 to 40 carbon atoms, preferably 3 to 24 carbon atoms, more preferably 3 to 12 carbon atoms; an aromatic or heteroaromatic ring system having 5 to 40 aromatic ring atoms, preferably 5 to 25 aromatic ring atoms, more preferably 5 to 18 aromatic ring atoms, wherein in each of the above-mentioned groups one or more H atoms may be replaced by D, F, Cl, Br, I, and where two or more adjacent substituents $R^a$ here may optionally form a mono- or polycyclic, aliphatic ring system with one another;

L is a divalent group selected from a straight-chain alkylene group having 1 to 40 carbon atoms, preferably 3 to 24 carbon atoms, more preferably 4 to 12 carbon atoms; a branched or cyclic alkylene group having 3 to 40 carbon atoms, preferably 4 to 24 carbon atoms, more preferably 5 to 12 carbon atoms; a straight-chain alkenylene or alkynylene group having 2 to 40 carbon atoms, preferably 3 to 24 carbon atoms, more preferably 4 to 12 carbon atoms; or a branched alkenylene group or alkynylene group having 3 to 40 carbon atoms, preferably 4 to 24 carbon atoms, more preferably 5 to 12 carbon atoms, each of which each may be substituted by one or more groups $R^a$, where in each case one or more $CH_2$ groups may be replaced by an arylene group or heteroarylene group having 5 to 40 aromatic ring atoms, preferably 5 to 25 aromatic ring atoms, more preferably 5 to 18 aromatic ring atoms, $Si(R^a)_2$, $Ge(R^a)_2$, $Sn(R^a)_2$, C═O, C═S, C═Se, $C{=}NR^a$, $P({=}O)(R^a)$, SO, $SO_2$, —O—, $NR^a$, —C(═O)O—, or $—C({=}O)NR^a—$, and where one or more H atoms may be replaced by D, F, Cl, Br, I, CN or $NO_2$; an aromatic or heteroaromatic ring system having 5 to 40 aromatic ring atoms, preferably 5 to 25 aromatic ring atoms, more preferably 5 to 18 aromatic ring atoms, an aralkylene group, a heteroaralkylene group, an alkylarylene group or an alkylheteroarylene group, each of which may be substituted by one or more groups $R^a$, and where in each case one or more H atoms may be replaced by D, F, Cl, Br, I, CN, $NO_2$; or a group represented by the following chemical formula (II)

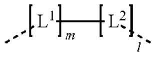 or 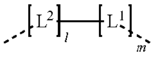 (II)

wherein m is an integer of 1 to 50, preferably 1 to 25, more preferably 2 to 20, and furthermore preferably 4 to 12;

l is an integer of 1 to 25, preferably 1 to 20, more preferably 1 to 12, and furthermore preferably 1 to 8;

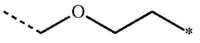, 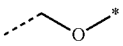, 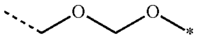

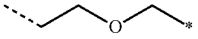, 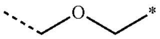, or

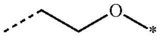, preferably

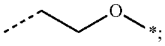;

$L^2$ is

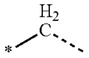 or 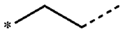, preferably

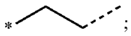;

wherein a dashed line indicates a bond to the remainder of the compound and the symbol "*" marks the bond between groups $L^1$ and $L^2$, and wherein each of $L^1$ and $L^2$ may be substituted by one or more groups $R^a$, where one or more $CH_2$ groups of $L^1$ and $L^2$ may be replaced by $—R^aC{=}CR^a—$, —C≡C—, $Si(R^a)_2$, $Ge(R^a)_2$, $Sn(R^a)_2$, C═O, C═S, C═Se, $C{=}NR^a$, $P({=}O)(R^a)$, SO, $SO_2$, $NR^a$, or $—C({=}O)NR^a—$, and where one or more H atoms in $L^1$ and $L^2$ may be replaced by D, F, Cl, Br, I, CN or $NO_2$;

$X^1$ is, identically or differently on each occurrence, an anchor group preferably selected from $—COOM^1$, $—PO(OH)(OM^1)$, $—PO(OM^1)_2$, $—OC(S)SM^1$, $—NH_2$, $—NHR^a$, $—N(R^a)_2$, $—SO_3M^1$, $—SM^1$, $—Ar^1—SM^1$, $—OCO\text{-}A^3\text{-}SM^1$, $—COO\text{-}A^3\text{-}SM^1$, $—NCO\text{-}A^3\text{-}SM^1$, $SiOR^a$, or $—N(CS_2\,M^1)_2$;

$Ar^1$ is a divalent group selected from an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms of the aromatic or heteroaromatic ring system may be replaced by D, F, Cl, Br, I, CN, $NO_2$;

$A^3$ is a divalent group selected from a straight-chain alkylene group having 1 to 40 carbon atoms, preferably 1 to 25 carbon atoms, more preferably 1 to 15 carbon atoms; a branched or cyclic alkylene group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by, $Si(R^a)_2$, $Ge(R^a)_2$, $Sn(R^a)_2$, C═O, C═S, C═Se, $C{=}NR^a$, $P({=}O)(R^a)$, SO, $SO_2$, —O—, $NR^a$, —C(═O)O—, or $—C({=}O)NR^a—$, and where one or more H atoms may be replaced by D, F, Cl, Br, I, CN or $NO_2$; an aromatic or heteroaromatic ring system having 5 to 25 aromatic ring atoms, preferably 5 to 18 aromatic ring atoms, more preferably 5 to 12 aromatic ring atoms, each of which may be substituted by one or more groups $R^a$, and where one or more H atoms of the aromatic or heteroaromatic ring system may be replaced by D, F, Cl, Br, I, CN, $NO_2$;

$M^1$ denotes a hydrogen atom, or a metal cation selected from ½ $Mg^{2+}$, ½ $Cu^{2+}$, ½ $Zn^{2+}$, ½ $Pb^{2+}$, ½ $Sn^{2+}$, ½ $Cd^{2+}$, ⅓ $Bi^{3+}$ or ¼ $Sn^{4+}$, preferably a hydrogen atom, ½ $Mg^{2+}$, ½ $Cu^{2+}$, or ½ $Zn^{2+}$, more preferably a hydrogen atom;

and at least one further functional material, which is preferably selected from the group consisting of organic light emitting materials, inorganic light emitting materials, charge transporting materials, host or matrix materials, optically transparent polymers, antioxidants or stabilizers, radical quenchers, photo initiators or polymerization initiators, wetting and dispersing agents, scattering particles, reflective index adjusting materials, developer-dissolution promoters, scum removers, adhesion enhancers, polymerization inhibitors, defoaming agents, surfactants and sensitizers.

16. Composition according to embodiment 15, wherein the compound of chemical formula (I) represents a compound of the following chemical formula (III)

(III)

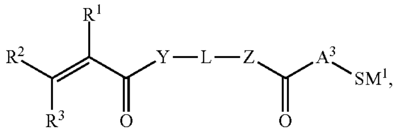

wherein the symbols occurring are as defined in embodiment 15, and wherein Z is NH or O.

17. Composition according to embodiment 15 or 16, wherein

L is selected from chemical formula (II)

(II)

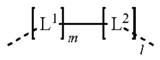

wherein $L^1$ is

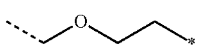 , 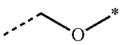 , 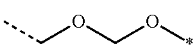

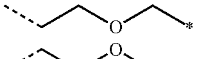 , 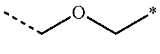 , or

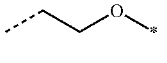 , preferably

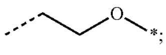 ;

$L^2$ is

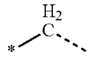 or 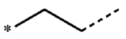 , preferably

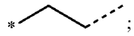 ;

wherein a dashed line indicates a bond to the remainder of the compound and the symbol "*" marks the bond between groups $L^1$ and $L^2$, and wherein each of $L^1$ and $L^2$ may be substituted by one or more groups $R^a$, where one or more $CH_2$ groups of $L^1$ and $L^2$ may be replaced by $-R^aC{=}CR^a-$, $-C{\equiv}C-$, $Si(R^a)_2$, $Ge(R^a)_2$, $Sn(R^a)_2$, C=O, C=S, C=Se, $C{=}NR^a$, $P({=}O)(R^a)$, SO, $SO_2$, $NR^a$, or $-C({=}O)NR^a-$, and where one or more H atoms in $L^1$ and $L^2$ may be replaced by D, F, Cl, Br, I, CN or $NO_2$; and $M^1$ is H, where m, l and $R^a$ are as defined in embodiment 15.

18. Composition according to any one of embodiments 15 to 17, wherein the composition comprises the compound represented by chemical formula (I) in an amount of 1 to 30 wt. % based on the total weight of the composition.

19. Composition according to embodiment 13, or composition according to embodiment 14, or composition according to any one of embodiments 15 to 18, wherein the at least one further functional material is a host or matrix material, which is preferably selected from (meth)acrylate monomers or polymers.

20. Formulation comprising a nanoparticle according to any one of embodiments 1 to 10, or a compound according to embodiment 11 or 12, or a composition according to any one of embodiments 13 to 19, and at least one solvent, which is preferably selected from the group consisting of esters such as, PGMEA (propylene glycol methyl ether acetate), ethyl acetate, butyl acetate, amyl acetate, ethylene carbonate, methoxy propyl acetate; ketones such as methyl ethyl ketone (MEK), methyl isobutyl ketone, cyclohexanone; glycols such as ethylene glycol, propylene glycol, butylene glycol, diethylene glycol, triethylene glycol, glycol ethers, hexylene glycol; ethers such as, diethyl ethers, tetrahydofuran, alcohols such as, methanol, ethanol, isopropanol, and butanol; or aromatic, halogenated and aliphatic hydrocarbons, such as toluene, xylene, chloroform, dichloromethane and heptane.

21. Use of a compound according to embodiment 11 as an additive in a composition which comprises a semiconducting light emitting nanoparticle having at least a core and optionally one or more shell layers, and at least one further functional material.

22. Use of a nanoparticle according to any one of embodiments 1 to 10, or a composition according to any one of embodiments 12 to 19, or a formulation according to embodiment 20, in an electronic device, optical device or biomedical device.

23. Optical medium comprising a nanoparticle according to any one of embodiments 1 to 10, or a compound according to embodiment 11 or 12, or a composition according to any one of embodiments 12 to 19, or a formulation according to embodiment 20.

24. Optical device comprising a nanoparticle according to any one of embodiments 1 to 10, or a compound according to embodiment 11 or 12, or a composition according to any one of embodiments 12 to 19, or a formulation according to embodiment 20, or said optical medium according to embodiment 23.

25. Process for the preparation of an optical device according to embodiment 24, comprising the following steps a) to c):

a) preparing a mixture by mixing a semiconducting light emitting nanoparticle having at least a core and optionally one or more shell layers, at least one further functional material, a compound represented by chemical formula (I) defined below and, optionally, at least one solvent;

b) providing the mixture onto a substrate;

c) subjecting the mixture obtained to a photo irradiation having a peak light wavelength in the range from 300 to 650 nm, preferably in the range from 320 to 520 nm, more preferably from 350 nm to 500 nm, even more preferably from 360 nm to 470 nm:

(I)

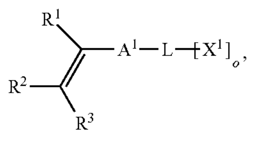

wherein is 1, 2 or 3, preferably 1;

$R^1$ is H, D, CN a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by $—R^aC{=}CR^a—$, —C≡C—, $Si(R^a)_2$, $Ge(R^a)_2$, $Sn(R^a)_2$, C═O, C═S, C═Se, $C{=}NR^a$, $P({=}O)(R^a)$, SO, $SO_2$, —O—, $NR^a$, —C(═O)O—, or $—C({=}O)NR^a—$, and where one or more H atoms may be replaced by D, F, Cl, Br, I, CN or $NO_2$; an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms may be replaced by D, F, Cl, Br, I, CN or $NO_2$;

$R^2$, $R^3$ are, independently of each other, H, D, CN, a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by $—R^aC{=}CR^a—$, —C≡C—, $Si(R^a)_2$, $Ge(R^a)_2$, $Sn(R^a)_2$, C═O, C═S, C═Se, $C{=}NR^a$, $P({=}O)(R^a)$, SO, $SO_2$, —O—, $NR^a$, —C(═O)O—, or $—C({=}O)NR^a—$, and where one or more H atoms may be replaced by D, F, Cl, Br, I, CN or $NO_2$; or an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms may be replaced by D, F, Cl, Br, I, CN or $NO_2$;

$A^1$ is

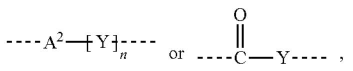

with n=0 or 1;

Y is O, NH, S, preferably O or NH;

$A^2$ is a divalent group selected from an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms of the aromatic or heteroaromatic ring system may be replaced by D, F, Cl, Br, I, CN, $NO_2$;

$R^a$ is at each occurrence, identically or differently, H, D, a straight chain alkyl or alkoxy group having 1 to 40 carbon atoms, preferably 1 to 25 carbon atoms, more preferably 1 to 15 carbon atoms; a branched or cyclic alkyl or alkoxy group having 3 to 40 carbon atoms, preferably 3 to 25 carbon atoms, more preferably 3 to 15 carbon atoms; a straight-chain alkenyl or alkynyl group having 2 to 40 carbon atoms, preferably 2 to 24 carbon atoms, more preferably 2 to 12 carbon atoms; a branched alkenyl group or alkynyl group having 3 to 40 carbon atoms, preferably 3 to 24 carbon atoms, more preferably 3 to 12 carbon atoms; an aromatic or heteroaromatic ring system having 5 to 40 aromatic ring atoms, preferably 5 to 25 aromatic ring atoms, more preferably 5 to 18 aromatic ring atoms, wherein in each of the above-mentioned groups one or more H atoms may be replaced by D, F, Cl, Br, I, and where two or more adjacent substituents $R^a$ here may optionally form a mono- or polycyclic, aliphatic ring system with one another;

L is a divalent group selected from a straight-chain alkylene group having 1 to 40 carbon atoms, preferably 3 to 24 carbon atoms, more preferably 4 to 12 carbon atoms; a branched or cyclic alkylene group having 3 to 40 carbon atoms, preferably 4 to 24 carbon atoms, more preferably 5 to 12 carbon atoms; a straight-chain alkenylene or alkynylene group having 2 to 40 carbon atoms, preferably 3 to 24 carbon atoms, more preferably 4 to 12 carbon atoms; or a branched alkenylene group or alkynylene group having 3 to 40 carbon atoms, preferably 4 to 24 carbon atoms, more preferably 5 to 12 carbon atoms, each of which each may be substituted by one or more groups $R^a$, where in each case one or more $CH_2$ groups may be replaced by an arylene group or heteroarylene group having 5 to 40 aromatic ring atoms, preferably 5 to 25 aromatic ring atoms, more preferably 5 to 18 aromatic ring atoms, $Si(R^a)_2$, $Ge(R^a)_2$, $Sn(R^a)_2$, C═O, C═S, C═Se, $C{=}NR^a$, $P({=}O)(R^a)$, SO, $SO_2$, —O—, $NR^a$, —C(═O)O—, or $—C({=}O)NR^a—$, and where one or more H atoms may be replaced by D, F, Cl, Br, I, CN or $NO_2$; an aromatic or heteroaromatic ring system having 5 to 40 aromatic ring atoms, preferably 5 to 25 aromatic ring atoms, more preferably 5 to 18 aromatic ring atoms, an aralkylene group, a heteroaralkylene group, an alkylarylene group or an alkylheteroarylene group, each of which may be substituted by one or more groups $R^a$, and where in each case one or more H atoms may be replaced by D, F, Cl, Br, I, CN, $NO_2$; or a group represented by the following chemical formula (II)

(II)

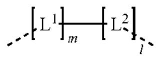 or 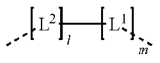

wherein m is an integer of 1 to 50, preferably 1 to 25, more preferably 2 to 20, and furthermore preferably 4 to 12;

l is an integer of 1 to 25, preferably 1 to 20, more preferably 1 to 12, and furthermore preferably 1 to 8;

$L^1$ is

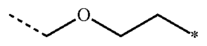, 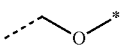, 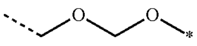

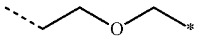, 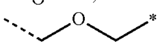, or

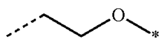, preferably

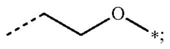;

$L^2$ is

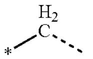 or 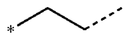, preferably

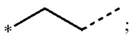;

wherein a dashed line indicates a bond to the remainder of the compound and the symbol "*" marks the bond between groups $L^1$ and $L^2$, and wherein each of $L^1$ and $L^2$ may be substituted by one or more groups $R^a$, where one or more $CH_2$ groups of $L^1$ and $L^2$ may be replaced by $—R^aC{=}CR^a—$, —C≡C—, $Si(R^a)_2$, $Ge(R^a)_2$, $Sn(R^a)_2$, C=O, C=S, C=Se, $C{=}NR^a$, $P({=}O)(R^a)$, SO, $SO_2$, $NR^a$, or $—C({=}O)NR^a—$, and where one or more H atoms in $L^1$ and $L^2$ may be replaced by D, F, Cl, Br, I, CN or $NO_2$;

$X^1$ is, identically or differently on each occurrence, an anchor group preferably selected from $—COOM^1$, $—PO(OH)(OM^1)$, $—PO(OM^1)_2$, $—OC(S)SM^1$, $—NH_2$, $—NHR^a$, $—N(R^a)_2$, $—SO_3M^1$, $—SM^1$, $—Ar^1—SM^1$, $—OCO\text{-}A^3\text{-}SM^1$, $—COO\text{-}A^3\text{-}SM^1$, $—NCO\text{-}A^3\text{-}SM^1$, $SiOR^a$, or $—N(CS_2M^1)_2$;

$Ar^1$ is a divalent group selected from an aromatic ring system or a heteroaromatic ring system having 5 to 40 aromatic ring atoms, preferably 5 to 25 aromatic ring atoms, more preferably 5 to 18 aromatic ring atoms, each of which may be substituted by one or more groups $R^a$, and where one or more H atoms of the aromatic or heteroaromatic ring system may be replaced by D, F, Cl, Br, I, CN, $NO_2$;

$A^3$ is a divalent group selected from a straight-chain alkylene group having 1 to 40 carbon atoms, preferably 1 to 25 carbon atoms, more preferably 1 to 15 carbon atoms; a branched or cyclic alkylene group having 3 to 40 carbon atoms, preferably 3 to 25 carbon atoms, more preferably 3 to 15 carbon atoms, each of which may be substituted by one or more groups $R^a$, where in each case one or more $CH_2$ groups may be replaced by, $Si(R^a)_2$, $Ge(R^a)_2$, $Sn(R^a)_2$, C=O, C=S, C=Se, $C{=}NR^a$, $P({=}O)(R^a)$, SO, $SO_2$, —O—, $NR^a$, —C(=O)O—, or $—C({=}O)NR^a—$, and where one or more H atoms may be replaced by D, F, Cl, Br, I, CN or $NO_2$; an aromatic or heteroaromatic ring system having 5 to 25 aromatic ring atoms, preferably 5 to 18 aromatic ring atoms, more preferably 5 to 12 aromatic ring atoms, each of which may be substituted by one or more groups $R^a$, and where one or more H atoms of the aromatic or heteroaromatic ring system may be replaced by D, F, Cl, Br, I, CN, $NO_2$;

$M^1$ denotes a hydrogen atom, or a metal cation selected from ½ $Mg^{2+}$, ½ $Cu^{2+}$, ½ $Zn^{2+}$, ½ $Pb^{2+}$, ½ $Sn^{2+}$, ½ $Cd^{2+}$, ⅓ $Bi^{3+}$ or ¼ $Sn^{4+}$, preferably a hydrogen atom, ½ $Mg^{2+}$, ½ $Cu^{2+}$, or ½ $Zn^{2+}$, more preferably a hydrogen atom.

27. Process according to embodiment 26, wherein the at least one further functional material is selected from the group consisting of organic light emitting materials, inorganic light emitting materials, charge transporting materials, host or matrix materials, optically transparent polymers, anti-oxidants or stabilizers, radical quenchers, photo initiators or polymerization initiators, wetting and dispersing agents, scattering particles, reflective index adjusting materials, developer-dissolution promoters, scum removers, adhesion enhancers, polymerization inhibitors, defoaming agents, surfactants and sensitizers, and preferably is selected from host or matrix materials, which are more preferably selected from (meth)methacrylate monomers or polymers; and/or wherein the at least one optional solvent is selected from the group consisting of esters such as, PGMEA (propylene glycol methyl ether acetate), ethyl acetate, butyl acetate, amyl acetate, ethylene carbonate, methoxy propyl acetate; ketones such as methyl ethyl ketone (MEK), methyl isobutyl ketone, cyclohexanone; glycols such as ethylene glycol, propylene glycol, butylene glycol, diethylene glycol, triethylene glycol, glycol ethers, hexylene glycol; ethers such as, diethyl ethers, tetrahydofuran, alcohols such as, methanol, ethanol, isopropanol, and butanol; or aromatic, halogenated and aliphatic hydrocarbons, such as toluene, xylene, chloroform, dichloromethane and heptane.

Effect of the Invention

The present invention provides one or more of the technical effects listed below:

a novel semiconducting light emitting nanoparticle, which can show high quantum yield and high luminous efficiency, in particularly when being used in electronic devices, optical devices or biomedical devices;

a novel semiconducting light emitting nanoparticle, which has improved thermal stability;

- a novel semiconducting light emitting nanoparticle, which has improved long-term stability;
- a novel semiconducting light emitting nanoparticle, which has good solubility, preferably in polar solvents;
- a novel semiconducting light emitting nanoparticle, which has high chemical compatibility with various polymeric systems commonly used in the manufacturing of electronic, optical or biomedical devices, in particular (meth)acrylate- or epoxy-based systems;
- a novel semiconducting light emitting nanoparticle, which can maintain a stable dispersion in a solution, formulation or film (including after film curing); a novel compound, which can impart increased stability to the surface of a nanoparticle and which can be polymerized and/or crosslinked to further enhance the stability of the underlying nanoparticle;
- a novel compound, which can passivate the nanoparticle surface and provide chemical compatibility to the nanoparticles with various solvents and polymeric systems used in the manufacturing of electronic, optical or biomedical devices, in particular polar solvents and (meth)acrylate- or epoxy-based systems;
- a novel compound, which can prevent nanoparticle aggregation and can ensure good dispersion of the nanoparticle in a solution, formulation or film (including after film curing);
- an optical device, which has high luminous efficiency, high brightness, high contrast, high reliability and short response times; and
- a simple preparation process for making an optical device.

The invention is described in more detail in reference to the following examples, which are only illustrative and do not limit the scope of the invention.

WORKING EXAMPLES

Compounds Used in the Examples:

TABLE 1

| Compounds related to chemical formula (I) used in the examples: | |
|---|---|
| Compound number | Chemical structure |
| (1) | 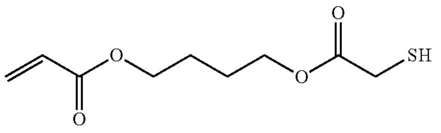 |
| (2) | 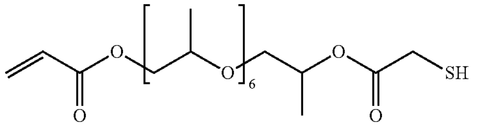 |

Working Example 1—Preparation of 4-[(2-sulfanylacetyl)oxy]butyl prop-2-enoate (1)

In the absence of light, 180 mL of extra dry toluene, benzene-1,4-diol (0.038 g, 0.01 eq.), 4-hydroxybutyl prop-2-enoate (5.3 g, 1 eq.) and 2-sulfanylacetic acid (2.3 g, 0.67 eq.) are added under argon atmosphere and while stirring into a 250 mL round bottom flask connected to a Dean-Stark apparatus. To this mixture, 4-methylbenzene-1-sulfonic acid (0.25 g, 0.04 eq.) is added. The mixture thus obtained is then boiled under reflux and under argon atmosphere for 18 hours with stirring. Then, heating is stopped, and the system is allowed to cool to room temperature (without external cooling). In the next step, the mixture is washed with distilled water, and after phase separation, drying with $MgSO_4$ and filtration using a Buchner funnel apparatus, benzene-1,4-diol (0.010 g) is added. The solvent is then removed using a rotary evaporator at 5 mbar and 30° C. 7.1 g of pure 4-[(2-sulfanylacetyl)oxy]butyl prop-2-enoate (yield: 87.9%) is obtained.

Working Example 2—Preparation of 2,5,8,11,14,17-hexamethyl-20-[(2-sulfanylacetyl)oxy]-3,6,9,12,15,18-hexaoxahenicosan-1-yl prop-2-enoate (2)

In the absence of light, 180 mL extra dry toluene, benzene-1,4-diol (0.050 g, 0.03 eq.), 20-hydroxy-2,5,8,11,14,17-hexamethyl-3,6,9,12,15,18-hexaoxahenicosan-1-yl prop-2-enoate (7.65 g, 1 eq.) and 2-sulfanylacetic acid (0.98 g, 0.67 eq.) are added under argon atmosphere into a 250 mL round bottom flask connected to a Dean-Stark apparatus while stirring. Then, 4-methylbenzene-1-sulfonic acid (0.2 g, 0.07 eq.) is added. The mixture thus obtained is then boiled under reflux and under argon atmosphere for 18 hours with stirring. Then, heating is stop and the system is allowed to cool to room temperature (without external cooling). In the next step, the mixture is washed with distilled water, and after phase separation, drying with $MgSO_4$ and filtration using a Buchner funnel apparatus, benzene-1,4-diol (0.010 g) is added. The solvent is removed using a rotary evaporator at 5 mbar and 30° C. 8 g of pure 2,5,8,11,14,17-hexamethyl-20-[(2-sulfanylacetyl)oxy]-3,6,9,12,15,18-hexaoxa-henicosan-1-yl prop-2-enoate (yield: 90.5%) is obtained as a product.

Working Example 3—Functionalization of Quantum Material with Compound (1) and Compound (2) as Ligands 298 μL (contains 30 mg inorganics) quantum dots (QDs) solution (red light emitting QDs manufactured as described in WO 2014/162208 and/or U.S. Pat. No. 9,343,301 BB, denoted herein as "red QDs@native") is mixed with 30 mg of compound (1) or (2) and stirred for 16 hours under inert atmosphere and at room temperature. In the sample containing compound (1), some precipitate is formed, which is removed by centrifuge (5500 rpm, 5 min) and the supernatant is collected. In the sample containing compound (2), no precipitate forms. The thus obtained QDs functionalized with either compound (1) or (2) as ligands are denoted as red QDs@ligand#1 and #2, respectively (in each case, TGA shows 60 wt. % ligands, based on the total weight of the QDs). The amount of organic ligands (compound (1) or (2)) is calculated using thermal gravimetric analysis (TGA) (model TGA2, Metler Toledo). Quantum materials are dissolved in toluene. Quantum yield is measured using Hamamatsu absolute quantum yield spectrometer (model: Quantaurus C11347). The results of the quantum yield measurements are summarized in Table 2 below.

Working Example 4—Stability Measurements of QDs ("Red QDs@Native", "Red QDs@Ligand#1" and "Red QDs@Ligand#2") in Hydrophobic Ink Formulation (Formulation 1)

Ink formulation preparation: A hydrophobic ink formulation (denoted herein as "formulation 1") is prepared by mixing TBCH (4-tertbutylcyclohexyl acrylate), LA (lauryl acrylate) and trimethylolpropane triacrylate (TMPTA) in a weight ratio of 67.5:27.5:5, respectively. Then, 1% wt. of photoinitiator Irgacure819 is dissolved in the ink formulation.

The following synthesis (including film preparation and thermal stability test) is carried out with each QDs obtained from working example 5 (i.e, "red QDs@native", "red QDs@ligand#1" and "red QDs@ligand#2") QDs obtained from working example 3 are dried under vacuum. The dried QDs are mixed with ink formulation 1 in a concentration of 30 wt. % (organic and inorganic weight) (this mixture is denoted as "QDs@TBCH-1").

Film preparation: A glass substrate (4×4 cm) is coated with QDs@TBCH-1 to form a film with a thickness of approximately 10 μm. Polymerization of the monomers is conducted by irradiation with UV light (365 nm wavelength) for 10 minutes under inert conditions (argon). The quantum yield after film curing is measured (at the same day) using a Hamamatsu absolute quantum yield spectrometer (model: Quantaurus C11347). The results of the quantum yield measurements are summarized in Table 3 below.

Thermal stability test: The film obtained after UV curing is placed in a tube oven under argon atmosphere and heated to 180° C. for 0.5 hour. The quantum yield of the heated film is measured 1 day after heating, and in specific cases 1 week after heating. The results of the quantum yield measurements are summarized in Table 3 below.

Working Example 5—Stability Measurements of QDs ("Red QDS@Native", "Red Ds@Ligand#1", "Red QDs@Ligand#2") in Hydrophobic Ink Formulation (Formulation 2)

Ink formulation preparation: A hydrophobic ink formulation (denoted herein as "formulation 2") is prepared by dissolving 1 wt. % of Irgacure819 with isobornyl acrylate (IBOA). QDs obtained from working example 3 ("red QDS@native", "red QDs@ligand#1", "red QDs@ligand#2") are dried under vacuum. Each of the dried QDs are mixed with ink formulation 2 in a concentration of 30 wt. % (organic and inorganic weight).

Film preparation: Same as in working example 4. The results of the quantum yield measurements are summarized in Table 3 below.

Thermal stability test: Same as in working example 4. The results of the quantum yield measurements are summarized in Table 3 below.

Working Example 6—Functionalization of Quantum Material with Compound (2) as Ligand 500 μL (contains 30 mg inorganics) QDs solution (green light emitting QDs manufactured as described in WO 2014/162208 and/or U.S. Pat. No. 9,343,301 BB, denoted as "green QDs@native") is mixed with 30 mg (or 15 mg) of compound (2) and stirred for 16 hours under inert atmosphere at room temperature. No precipitate is formed. In one part of the sample, the excess of compound (2) is not washed away. The thus obtained QDs functionalized with compound (2) as ligand are denoted as "green QDs@ligand#2 no wash" (TGA shows 55 wt. % ligands, based on the total weight of the ODs). In the other part, 1 mL of anhydrous ethanol is added followed by centrifuging (5500 rpm, 5 min) to separate the QDs. The supernatant is removed and the solid obtained is dried under vacuum. The thus obtained QDs functionalized with compound (2) as ligand are denoted as "green QDs@ligand#2 after wash" (TGA shows 30 wt. % ligands based on the total weight of the QDs). The amount of organic ligands (compound (2)) is calculated using thermal gravimetric analysis (TGA) (model TGA2, Metler Toledo). Quantum materials are dissolved in 1 mL toluene. Quantum yield is measured using a Hamamatsu absolute quantum yield spectrometer (model: Quantaurus C11347). The results of the quantum yield measurements are summarized in Table 2 below.

Working Example 7—Stability Measurements of QDs ("Green QDs@Native", "Green QDs@Ligand#2 No Wash", "Green QDs@Ligand#2 after Wash") in Ink Formulation 1

The following synthesis (including film preparation and thermal stability test) is carried out with each QDs obtained from working example 6 (i.e, "green QDs@native", "green QDs@ligand#4 no wash", "green QDs@ligand#2 after wash").

QDs obtained from working example 6 are dried under vacuum. The dried QDs are mixed with ink formulation 1 in a concentration of 30 wt. % (organic and inorganic weight) (this mixture is denoted as "QDs@TBCH-2").

Film preparation: A glass substrate (4×4 cm) is coated with QDs@TBCH-2 to form a film with a thickness of about 10 μm. Polymerization of the monomers is conducted by irradiation with UV light (365 nm wavelength) for 10 minutes in inert conditions (argon). The quantum yield after film curing is measured (at the same day) using a Hamamatsu absolute quantum yield spectrometer (model: Quantaurus C11347). The results of the quantum yield measurements are summarized in Table 3 below.

Thermal stability test: The film obtained after UV curing is placed in a tube oven under argon atmosphere and heated to 180° C. for 0.5 hour. The quantum yield of the heated film is measured 1 day after heating, and in specific cases 1 week after heating. The results of the quantum yield measurements are summarized in Table 3 below.

Working Example 8—Stability Measurements of QDs ("Green QDs@Native") in Ink Formulation 1 with Compound (2) as an Additive QDs (green QDs@native) from working example 6 are dried and dissolved in ink formulation 1 in a concentration of 30 wt. % (organic and inorganic weight). 30 μL of compound (2) is added directly to the ink (this mixture is denoted as "QDs@TBCH-3").

Film preparation: A glass substrate (4×4 cm) is coated using a hand bar coater with 25 μL of QDs@TBCH-3 to form a film with a thickness of about 10 μm. Polymerization of the monomers is conducted by irradiation with UV light (365 nm wavelength) for 10 minutes in inert conditions (argon). The quantum yield after film curing is measured (at the same day) using a Hamamatsu absolute quantum yield spectrometer (model: Quantaurus C11347). The result of the quantum yield measurement is summarized in Table 3 below.

Thermal stability test: The film obtained film after UV curing is placed in a tube oven under argon atmosphere and heated to 180° C. for 0.5 hours. The quantum yield of the heated film is measured 1 day after heating. The result of the quantum yield measurement is summarized in Table 3 below.

Working Example 9—Stability Measurements of QDs ("Green QDs@Native") in Ink Formulation 2

QDs ("green QDs@native") from working example 6 are dried and dissolved in ink formulation 2 in a concentration of 30 wt. % (organic and inorganic weight).

Film preparation and thermal stability test are performed as described in working example 8. The results of the quantum yield measurements are summarized in Table 3 below.

Working Example 10—Stability Measurements of QDs ("Green QDs@Native) in Ink Formulation 2 with Compound (2) as an Additive QDs ("green QDs@native") from working example 6 are dried and dissolved in ink formulation 2 in a concentration of 30 wt. % (organic and inorganic weight). 30 μL of compound (2) is added directly to the ink formulation.

Film preparation and thermal stability test are performed as described in working example 8. The results of the quantum yield measurements are summarized in Table 3 below.

Working Example 11—Preparation of Monomer Mixture Ink with 33.1 wt % of Green Cd-Free QM and 26.5 wt % of Compound (2) as an Additive 0.39 g of 4-tert-butylcyclohexyl acrylate (TBCH, BASF), 0.95 g of lauryl acrylate (LA, Sigma Aldrich), and 0.07 g of trimethylolpropane triacrylate (TMPTA, Sigma Aldrich) are mixed, and 0.01 g of dispersing agent (MD-1000, Otsuka Chemical) is dispersed into the obtained mixture by stirring and sonicating. Then, 0.15 g of scattering beads (CR-67, Ishihara Sangyo) is mixed with the obtained mixture by sonicating and milling with zirconium beads. 13.9 ml of green Cd-free QM toluene solution (green light emitting QDs manufactured as described in WO 2014/162208 and/or U.S. Pat. No. 9,343,301 BB, denoted as "green QDs@native"), containing 1.32 g of solid QM, is mixed with the obtained mixture by sonicating, and toluene is evaporated at 40° C. under low pressure. Finally, 1.06 g of compound (2) prepared according to Working Example 2, 0.03 g of photo-initiator (Omnirad 819, IGM RESINS B.V.) and 0.02 g of stabilizer (Irganox1010, BASF) are mixed with the obtained mixture by stirring and sonicating.

Comparative Example 1—Preparation of Monomer Mixture Ink with 33.1 wt % of Green Cd-Free QM 0.68 g of 4-tert-butylcyclohexyl acrylate (TBCH, BASF), 1.67 g of lauryl acrylate (LA, Sigma Aldrich), and 0.12 g of trimethylolpropane triacrylate (TMPTA, Sigma Aldrich) are mixed, and 0.01 g of dispersing agent (MD-1000, Otsuka Chemical) is dispersed into the obtained mixture by stirring and sonicating. Then 0.15 g of scattering beads (CR-67, Ishihara Sangyo) is mixed with the obtained mixture by sonicating and milling with zirconium beads. 13.9 ml of green Cd-free QM toluene solution (green light emitting QDs manufactured as described in WO 2014/162208 and/or U.S. Pat. No. 9,343,301 BB, denoted as "green QDs@native"), containing 1.32 g of solid QM, is mixed with the obtained mixture by sonicating, and toluene is evaporated at 40° C. under low pressure. Finally, 0.03 g of photo-initiator (Omnirad 819, IGM RESINS B.V.) and 0.02 g of stabilizer (Irganox1010, BASF) are mixed with the obtained mixture by stirring and sonicating.

Working Example 12—Preparation of Monomer Mixture Ink with 38.1 wt % of Green Cd-Free QM and 15.3 wt % of Compound (2) as an Additive 0.45 g of 4-tert-butylcyclohexyl acrylate (TBCH, BASF), 1.10 g of lauryl acrylate (LA, Sigma Aldrich), and 0.08 g of trimethylolpropane triacrylate (TMPTA, Sigma Aldrich) are mixed, and 0.01 g of dispersing agent (MD-1000, Otsuka Chemical) is dispersed into the obtained mixture by stirring and sonicating. Then 0.17 g of scattering beads (CR-67, Ishihara Sangyo) is mixed with the obtained mixture by sonicating and milling with zirconium beads. 16.0 ml of green Cd-free QM toluene solution (green light emitting QDs manufactured as described in WO 2014/162208 and/or U.S. Pat. No. 9,343,301 BB, denoted as "green QDs@native"), containing 1.53 g of solid QM, is mixed with the obtained mixture by sonicating, and toluene is evaporated at 40° C. under low pressure. Finally, 0.61 g of compound (2) prepared according to Working Example 2, 0.03 g of photo-initiator (Omnirad 819, IGM RESINS B.V.) and 0.03 g of stabilizer (Irganox1010, BASF) are mixed with the obtained mixture by stirring and sonicating.

Comparative Example 2—Preparation of Monomer Mixture Ink with 38.1 wt % of Green Cd-Free QM 0.61 g of 4-tert-butylcyclohexyl acrylate (TBCH, BASF), 1.51 g of lauryl acrylate (LA, Sigma Aldrich), and 0.11 g of trimethylolpropane triacrylate (TMPTA, Sigma Aldrich) are mixed, and 0.01 g of dispersing agent (MD-1000, Otsuka Chemical) is dispersed into the obtained mixture by stirring and sonicating. Then 0.17 g of scattering beads (CR-67, Ishihara Sangyo) is mixed with the obtained mixture by sonicating and milling with zirconium beads. 16.0 ml of green Cd-free QM toluene solution (green light emitting QDs manufactured as described in WO 2014/162208 and/or U.S. Pat. No. 9,343,301 BB, denoted as "green QDs@native"), containing 1.53 g of solid QM, is mixed with the obtained mixture by sonicating, and toluene is evaporated at 40° C. under low pressure. Finally, 0.03 g of photo-initiator (Omnirad 819, IGM RESINS B.V.) and 0.03 g of stabilizer (Irganox1010, BASF) are mixed with the obtained mixture by stirring and sonicating.

The compositions of the monomer mixture inks prepared according to working examples 11 and 12 and comparative examples 1 and 2 are presented in Table 4 below.

Working Example 13—Optical Measurements

Film preparation: Each of the monomer mixture inks obtained from working examples 11 and 12 and comparative examples 1 and 2 are injected into a cell, which is sandwiched between glass substrates with sealant, by capillary injection to form respective films with a thickness of about 15 μm. Polymerization of the monomers is conducted by irradiation with UV light (3.9 $mW/cm^2$ at 365 nm (i-line)) for 200 sec. under inert conditions ($N_2$).

Optical Measurements:

External quantum efficiency of the films prepared is measured by a EQE measurement system contains halogen lamp (LUMOLUX fuse optik) with band pass filter (CWL: 450 nm/FWHM:10 nm), integrating sphere (ISP-50-8-R, Ocean Optics) and spectrometer (USB-4000, Ocean Optics).

Emission spectra of the films prepared are measured by a blue excitation light at 450 nm illuminated on glass side of the film through optical fiber. The diameter of the illuminating area is around 5 mm. The size of the film substrate is larger than the a port of integrating sphere. Green emission light from the QD film and non-absorbed blue excitation light come into a integrating sphere. Integrated light is transported to a spectrometer through optical fiber.

Figure 2:
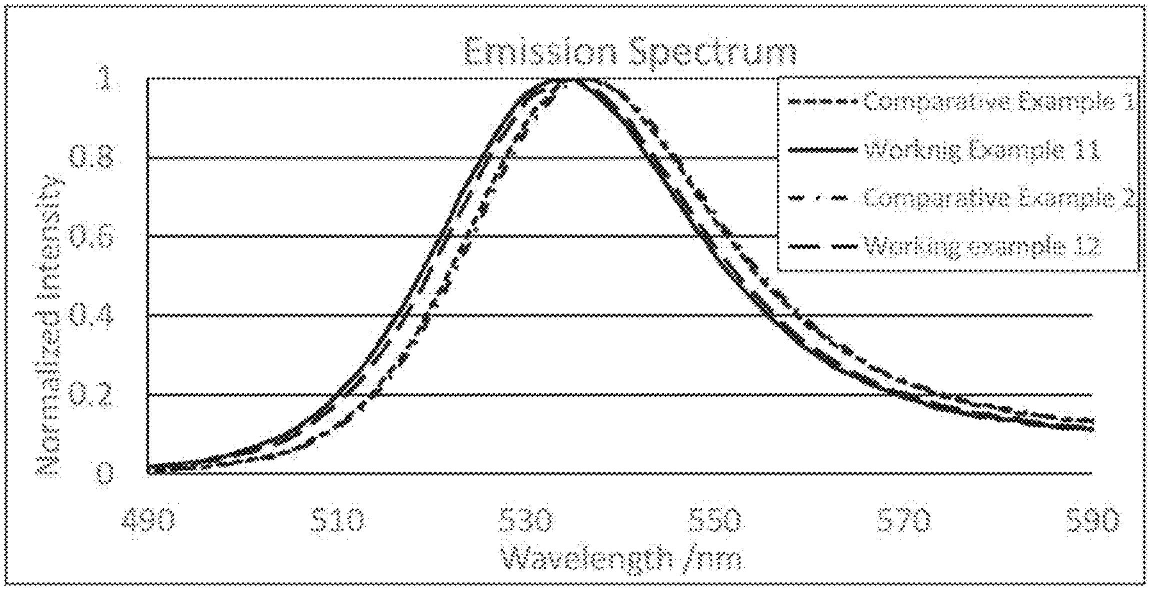
FIG. 2 is an emission spectrum of normalized intensity over wavelength showing a shift of maximum intensity of quantum material containing films obtained from working examples 13, each measured at same conditions.
Figure 3:
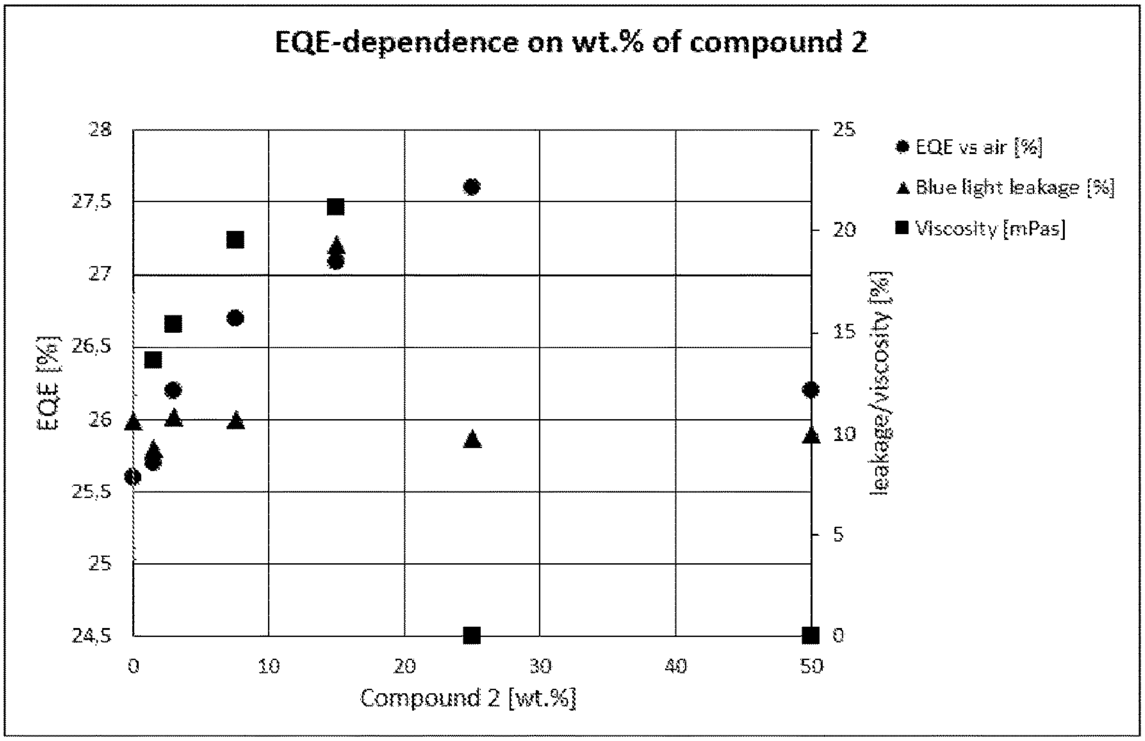
FIG. 3 shows EQE measurement results of working example 14.

The results of the optical measurements of the quantum material containing films prepared using the monomer mixture inks obtained in working examples 11 and 12 and comparative examples 1 and 2 are shown in FIGS. 1 and 2.

Experimental Results:

TABLE 2

Quantum yield for QDs functionalized with acrylate-thiol ligands and ligands amount:

| Samples | QY (%) in toluene solution | Amount of compound (1) or (2) (wt. %)* |
|---|---|---|
| Work.Ex. 3-red QDs@native | 68 | 30 |
| Work.Ex. 3-red QDs@ligand#1 | 68 | 60 |
| Work.Ex. 3-red QDs@ligand#2 | 68 | 60 |
| Work.Ex. 6-green QDs@native | 63 | 30 |
| Work.Ex. 6-green QDs@ ligand#2 no wash | 66 | 55 |
| Work.Ex. 6-green QDs@ ligand#2 after wash | 66 | 30 |

*based on the total weight of the QD

TABLE 3

Results of quantum yield measurements of QDs (red and green) film after UV curing and heating

| Work. Ex. No. | Samples | Quantum yield (%) Film after curing* | Film 1 day after heating | Film 1 week after heating | Amount of compound (1) or (2) (wt. %)** |
|---|---|---|---|---|---|
| 4 | red QDs@native | 68 | 51 | | |
| 4 | red QDs@ligand#1 | 70 | 67 | | |
| 4 | red QDs@ligand#2 | 66 | 60 | | |
| 5 | red QDs@native | 68 | 51 | | |
| 5 | red QDs@ligand#1 | 70 | 66 | | |
| 5 | red QDs@ligand#2 | 71 | 65 | | |
| 7 | green QDs@native | 64 | 53 | 47 | |
| 7 | green QDs@ligand#2 no wash | 64 | 60 | 60 | |
| 7 | green QDs@ligand#2 after wash | 63 | 58 | | |
| 8 | green QDs@ native + compound (2) | 63 | 61 | | |
| 9 | green QDs@native | 58 | 42 | | |
| 10 | green QDs@ native + compound (2) | 64 | 57 | | |

(*QY measured 5 to 15 min after curing;
**based on the total weight of the ink formulation), calculated using TGA; model TGA2, Metler Toledo)

As can be seen from the results presented in Tables 2 and 3, in all experiments the quantum yield of red or green QDs does not significantly drop after film UV-curing (in specific cases QY is even higher after curing). On the other hand, the results presented in Table 3 show that a drop in quantum yield is observed upon heating of the cured films (1 day after heating). However, while the drop in quantum yield is very significant for the QDs with native ligands, the drop is significantly reduced (that is, QY stability is increased) for QDs according to the present invention, i.e., after ligand exchange with bifunctional acrylate-based compounds as defined herein (here, thiol-acrylate compounds (1) or (2)), indicating that the thermal stability of QDs according to the present invention (i.e., after ligand exchange with bifunctional acrylate-based compounds of chemical formula (I) as defined herein) is significantly increased. Specifically, as can be seen from working examples 4 and 5 in Table 3, bifunctional acrylate-based ligands according to the present invention can contribute to higher stability of red QDs in IBOA-containing ink formulation (formulation 2) as well as in TBCH/LA/TMPTA-containing ink formulation (formulation 1). Furthermore, as can be seen from working example 7, bifunctional acrylate-based ligands according to the present invention can contribute to higher stability of green QDs in TBCH/LA/TMPTA formulation (formulation 1), even 1 week after heating ("green QDs@ligand#2 no wash"). A comparison of the experimental results from working examples 7 and 8 as well as 9 and 10 also reveals that higher stability is also obtained in such cases where bifunctional acrylate-based compounds of chemical formula (I) as defined herein (here, thiol-acrylate compound (2)) are used according to the present invention as an additive added directly to a QDs-containing ink formulation.

TABLE 4 compositions of the monomer mixture inks prepared in working examples 11 and 12 and comparative examples 1 and 2.

| | | Comp. Ex. 1 (wt %) | Work. Ex. 11 (wt %) | Comp. Ex. 2 (wt %) | Work. Ex. 12 (wt %) |
|---|---|---|---|---|---|
| Green QDs | "green QDs@native" | 33.1 | 33.1 | 38.1 | 38.1 |
| Monomer | TBCH | 17.0 | 9.7 | 15.4 | 11.2 |
| | LA | 41.7 | 23.8 | 37.7 | 27.4 |
| | TMPTA | 3.1 | 1.8 | 2.8 | 2.0 |
| Scattering Beads | CR-67 | 3.6 | 3.6 | 4.3 | 4.3 |
| Dispersant | MD-1000 | 0.2 | 0.2 | 0.2 | 0.2 |
| Photo-initiator | Omnirad 819 | 0.7 | 0.7 | 0.8 | 0.8 |
| Stabilizer | Irganox 1010 | 0.6 | 0.6 | 0.7 | 0.7 |
| Additive | Compound (2) | — | 26.5 | — | 15.3 |

FIG. 1 is a diagram of external quantum efficiency (EQE)/% demonstrating the change of EQE of QDs-containing films obtained from working example 13 using the inks prepared in working examples 11 and 12 and comparative examples 1 and 2.

FIG. 2 is an emission spectrum of normalized intensity over wavelength demonstrating the shift of maximum intensity of QDs-containing films obtained from working examples 13 using the inks prepared in working examples 11 and 12 and comparative examples 1 and 2.

As can be seen from the measurement results presented in FIGS. 1 and 2, when a bifunctional, polymerizable acrylate-based compound of chemical formula (I) as defined herein (here, thiol-acrylate compound (2)) is used according to the present invention as an additive added directly to a QDs-containing ink formulation (working examples 11 and 12), increase of EQE by 1 to 2% and reduction of red-shift by 1 to 2 nm in wavelength is achieved compared to ink formulations which do not contain such compound (comparative examples 1 and 2).

Working Example 14—Preparation of Monomer Mixture Inks

Monomer mixture inks are prepared in the same manner as described in the section of working example 11 except for that 1.5, 3, 7.5, 15, 25 and 25 wt. % of compound 2 are used as an additive. As a comparative example, monomer mixture ink without compound 2 (0 wt. %) is also prepared.

EQE measurements are carried out in the same manner as described in the working example 13.

TABLE 5

Table 5 shows the results of EQE measurements.

| Compound 2 [wt. %] | EQE [%] |
|---|---|
| 0 | 25.6 |
| 1.5 | 25.7 |
| 3 | 26.2 |
| 7.5 | 26.7 |
| 15 | 27.09 |
| 25 | 27.6 |
| 50 | 26.2 |

The invention claimed is:

1. A semiconducting light emitting nanoparticle comprising a core, optionally one or more shell layers, and a compound (I'), wherein the compound (I') represents:

(i) a compound of the following chemical formula (III):

(III)

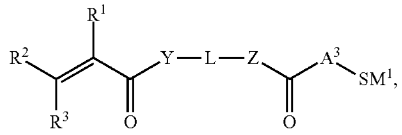

(ii) a compound of the following chemical formulae (IV), (V-a) or (V-b):

(IV)

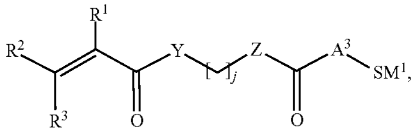

(V-a)

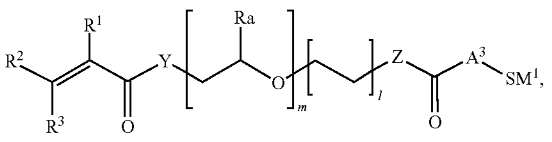

(V-b)

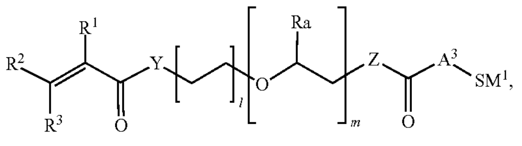

or (iii) a compound of one of the following chemical formulae (IV-1) to (IV-6) and (V-1) to (V-6):

(IV-1)

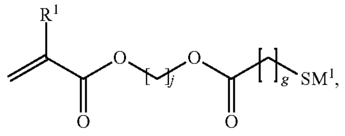

(IV-2)

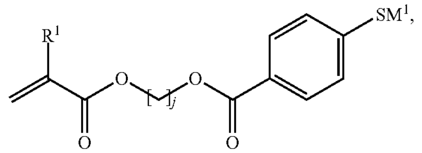

(IV-3)

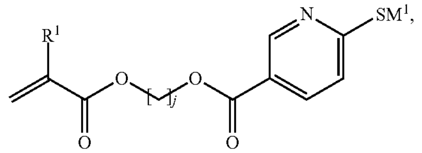

(IV-4)

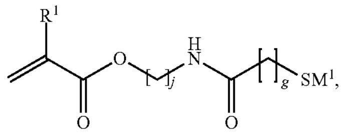

(IV-5)

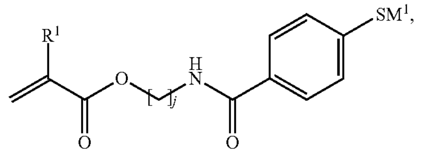

(IV-6)

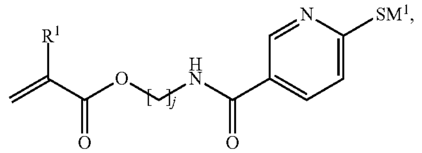

(V-1)

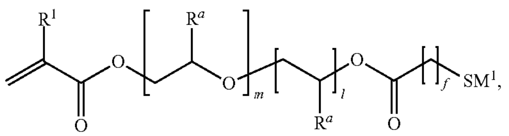

(V-2)

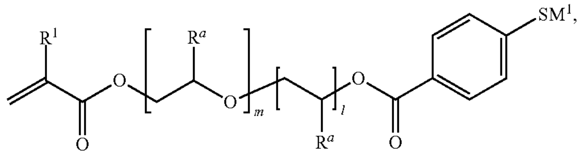

(V-3)

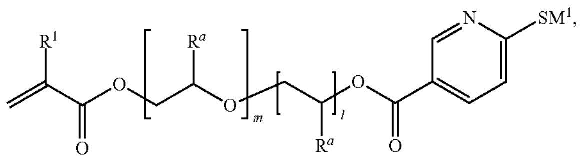

-continued (V-4)

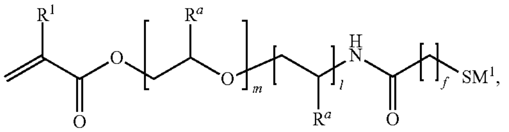

(V-5)

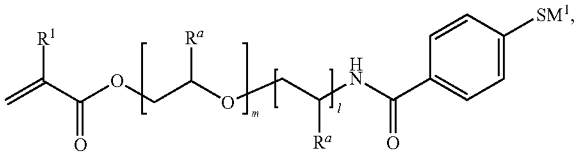

(V-6)

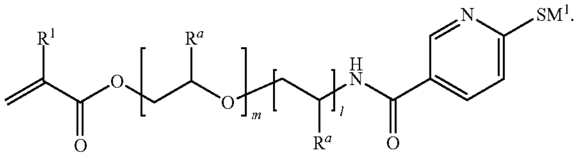

wherein $R^1$ is H, D, CN, a straight chain alkyl or alkoxy group having 1 to 40 carbon atoms, a branched or cyclic alkyl or alkoxy group having 3 to 40 carbon atoms, each of which may be substituted by one or more groups $R^a$, where in each case one or more $CH_2$ groups may each be replaced by —$R^a$C═C$R^a$—, —C≡C—, Si($R^a$)$_2$, Ge($R^a$)$_2$, Sn($R^a$)$_2$, C═O, C═S, C═Se, C═N$R^a$, P(═O)($R^a$), SO, $SO_2$, —O—, N$R^a$, —C(═O)O, or —C(═O)N$R^a$—, and where one or more H atoms may be replaced by D, F, Cl, Br, I, CN or $NO_2$; an aromatic ring system or a heteroaromatic ring system having 5 to 40 aromatic ring atoms, each of which may be substituted by one or more groups $R^a$, and where one or more H atoms may each be replaced by D, F, Cl, Br, I, CN or $NO_2$;

$R^2$, $R^3$ are, independently of each other, H, D, CN, a straight chain alkyl or alkoxy group having 1 to 40 carbon atoms, a branched or cyclic alkyl or alkoxy group having 3 to 40 carbon atoms, each of which may be substituted by one or more groups $R^a$, where in each case one or more $CH_2$ groups may each be replaced by —$R^a$C═C$R^a$—, —C≡C—, Si($R^a$)$_2$, Ge($R^a$)$_2$, Sn($R^a$)$_2$, C═O, C═S, C═Se, C═N$R^a$, P(═O)($R^a$), SO, $SO_2$, —O—, N$R^a$, —C(═O)O—, or —C(═O)N$R^a$—, and where one or more H atoms may each be replaced by D, F, Cl, Br, I, CN, or $NO_2$; or an aromatic ring system or a heteroaromatic ring system having 5 to 40 aromatic ring atoms, each of which may be substituted by one or more groups $R^a$, and where one or more H atoms may each be replaced by D, F, Cl, Br, I, CN, or $NO_2$;

Y is O, NH, or S;

$R^a$ is at each occurrence, identically or differently, H, D, a straight chain alkyl or alkoxy group having 1 to 40 carbon atoms, a branched or cyclic alkyl or alkoxy group having 3 to 40 carbon atoms, a straight-chain alkenyl or alkynyl group having 2 to 40 carbon atoms, a branched alkenyl group or alkynyl group having 3 to 40 carbon atoms, an aromatic or heteroaromatic ring system having 5 to 40 aromatic ring atoms, wherein in each of the above-mentioned groups one or more H atoms may each be replaced by D, F, Cl, Br, I, and where two or more adjacent substituents $R^a$ here may optionally form a mono- or polycyclic, aliphatic ring system with one another;

L is a divalent group selected from a straight-chain alkylene group having 1 to 40 carbon atoms, a branched or cyclic alkylene group having 3 to 40 carbon atoms, a straight-chain alkenylene or alkynylene group having 2 to 40 carbon atoms, or a branched alkenylene group or alkynylene group having 3 to 40 carbon atoms, each of which each may be substituted by one or more groups $R^a$, where in each case one or more $CH_2$ groups may each be replaced by an arylene group or heteroarylene group having 5 to 40 aromatic ring atoms, Si($R^a$)$_2$, Ge($R^a$)$_2$, Sn($R^a$)$_2$, C═O, C═S, C═Se, C═N$R^a$, P(═O)($R^a$), SO, $SO_2$, —O—, N$R^a$, —C(═O)O—, or —C(═O)N$R^a$—, and where one or more H atoms may each be replaced by D, F, Cl, Br, I, CN or $NO_2$; an aromatic or heteroaromatic ring system having 5 to 40 aromatic ring atoms, an aralkylene group, a heteroaralkylene group, an alkylarylene group or an alkylheteroarylene group, each of which may be substituted by one or more groups $R^a$, and where in each case one or more H atoms may each be replaced by D, F, Cl, Br, I, CN, $NO_2$; or a group represented by the following chemical formula (II):

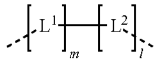

(II)

wherein m is an integer of 1 to 50;

l is an integer of 1 to 25;

$L^1$ is

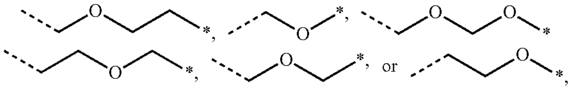

$L^2$ is

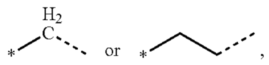

wherein a dashed line indicates a bond to the remainder of the compound and the symbol "*" marks the bond between groups $L^1$ and $L^2$, and wherein each of $L^1$ and $L^2$ may be substituted by one or more groups $R^a$, where one or more $CH_2$ groups of $L^1$ and $L^2$ may each be replaced by —$R^a$C═C$R^a$, —C≡C—, Si($R^a$)$_2$, Ge($R^a$)$_2$, Sn($R^a$)$_2$, C═O, C═S, C═Se, C═N$R^a$, P(═O)($R^a$), SO, $SO_2$, N$R^a$, or —C(═O)N$R^a$—, and where one or more H atoms in $L^1$ and $L^2$ may each be replaced by D, F, Cl, Br, I, CN or $NO_2$;

$A^3$ is a divalent group selected from a straight-chain alkylene group having 1 to 40 carbon atoms, a branched or cyclic alkylene group having 3 to 40 carbon atoms, each of which may be substituted by one or more groups $R^a$, where in each case one or more $CH_2$ groups may each be replaced by, Si($R^a$)$_2$, Ge($R^a$)$_2$, Sn($R^a$)$_2$, C═O, C═S, C═Se, C═N$R^a$, P(═O)($R^a$), SO, $SO_2$, —O—, $NR^a$, —C(═O)O—, or —C(═O)$NR^a$—, and where one or more H atoms may each be replaced by D, F, Cl, Br, I, CN, or $NO_2$; an aromatic or heteroaromatic ring system having 5 to 25 aromatic ring atoms, each of which may be substituted by one or more groups $R^a$, and where one or more H atoms of the aromatic or heteroaromatic ring system may each be replaced by D, F, Cl, Br, I, CN, or $NO_2$;

$M^1$ denotes a hydrogen atom, or a metal cation selected from ½ $Mg^{2+}$, ½ $Cu^{2+}$, ½ $Zn^{2+}$, ½ $Pb^{2+}$, ½ $Sn^{2+}$, ½ $Cd^{2+}$, ⅓ $Bi^{3+}$ or ¼ $Sn^{4+}$;

Z is NH or O;

j is an integer of 1 to 40; and indices g and f are identically or differently an integer of 1 to 40.

2. The semiconducting light emitting nanoparticle according to claim 1, wherein the compound (I') represents a compound of the following chemical formula (III):

(III)

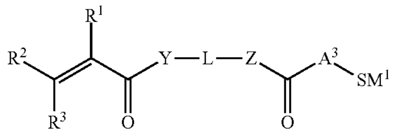

wherein the symbols occurring are as defined in claim 1.

3. The semiconducting light emitting nanoparticle according to claim 1, wherein the compound (I') represents a compound of the following chemical formulae (IV), (V-a) or (V-b):

(IV)

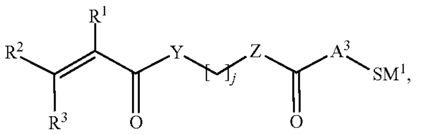

(V-a)

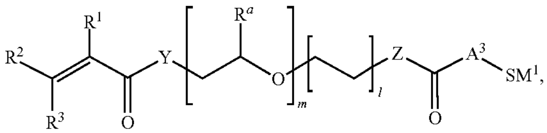

(V-b)

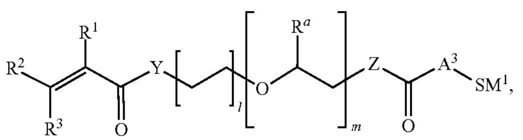

wherein the symbols and indices occurring are as defined in claim 1.

4. The semiconducting light emitting nanoparticle according to claim 1, wherein the compound (I') represents a compound of one of the following chemical formulae (IV-1) to (IV-6) and (V-1) to (V-6):

(IV-1)

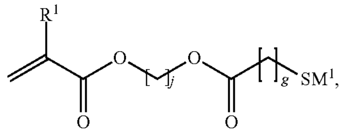

(IV-2)

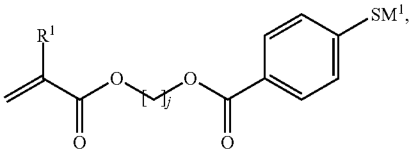

(IV-3)

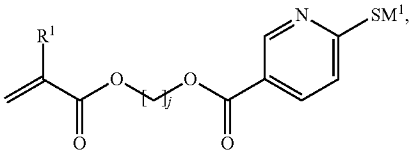

(IV-4)

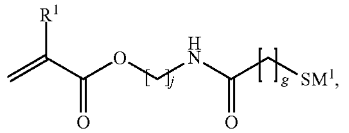

(IV-5)

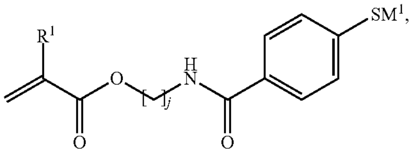

(IV-6)

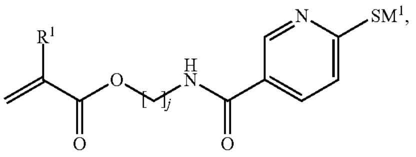

(V-1)

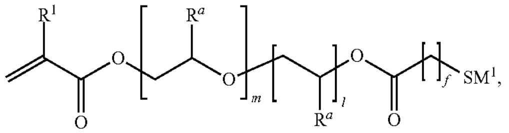

(V-2)

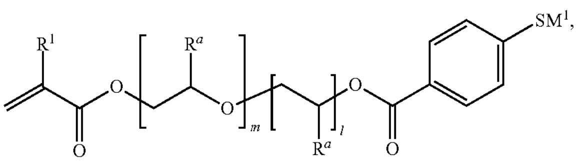

(V-3)

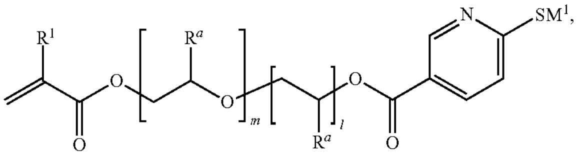

-continued (V-4)

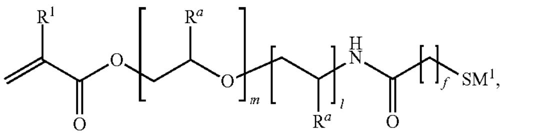

(V-5)

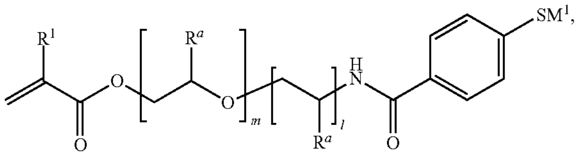

(V-6)

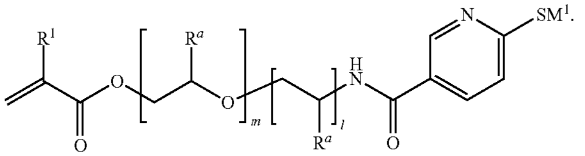

wherein the symbols and indices occurring have the meaning as in claim 1.

5. A composition comprising a nanoparticle according to claim 1 and at least one further functional material selected from the group consisting of organic light emitting materials, inorganic light emitting materials, charge transporting materials, host or matrix materials, optically transparent polymers, anti-oxidants or stabilizers, radical quenchers, photo initiators or polymerization initiators, wetting and dispersing agents, scattering particles, reflective index adjusting materials, developer-dissolution promoters, scum removers, adhesion enhancers, polymerization inhibitors, defoaming agents, surfactants and sensitizers.

6. The composition according to claim 5, wherein the at least one further functional material is a host or matrix material selected from (meth)acrylate monomers or polymers.

7. A composition comprising a semiconducting light emitting nanoparticle having at least a core, and optionally one or more shell layers, a compound (I') represented by chemical formula (III):

(III)

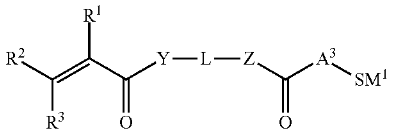

wherein $R^1$ is H, D, CN a straight chain alkyl or alkoxy group having 1 to 40 carbon atoms, a branched or cyclic alkyl or alkoxy group having 3 to 40 carbon atoms, each of which may be substituted by one or more groups $R^a$, where in each case one or more $CH_2$ groups may each be replaced by —$R^a$C═C$R^a$—, —C≡C—, Si$(R^a)_2$, Ge$(R^a)_2$, Sn$(R^a)_2$, C═O, C═S, C═Se, C═N$R^a$, P(═O)($R^a$), SO, $SO_2$, —O—, N$R^a$, C(═O)O, or C(═O)N$R^a$—, and where one or more H atoms may each be replaced by D, F, Cl, Br, I, CN, or $NO_2$; an aromatic ring system or a heteroaromatic ring system having 5 to 40 aromatic ring atoms, each of which may be substituted by one or more groups $R^a$, and where one or more H atoms may each be replaced by D, F, Cl, Br, I, CN, or $NO_2$;

$R^2$, $R^3$ are, independently of each other, H, D, CN, a straight chain alkyl or alkoxy group having 1 to 40 carbon atoms, a branched or cyclic alkyl or alkoxy group having 3 to 40 carbon atoms, each of which may be substituted by one or more groups $R^a$, where in each case one or more $CH_2$ groups may each be replaced by —$R^a$C═C$R^a$—, —C≡—C, Si$(R^a)_2$, Ge$(R^a)_2$, Sn$(R^a)_2$, C═O, C═S, C═Se, C═N$R^a$, P(═O)($R^a$), SO, $SO_2$, —O—, N$R^a$, —C(═O)O—, or —C(═O)N$R^a$—, and where one or more H atoms may each be replaced by D, F, Cl, Br, I, CN, or $NO_2$; or an aromatic ring system or a heteroaromatic ring system having 5 to 40 aromatic ring atoms, each of which may be substituted by one or more groups $R^a$, and where one or more H atoms may each be replaced by D, F, Cl, Br, I, CN, or $NO_2$;

Y is O, NH, or S;

$R^a$ is at each occurrence, identically or differently, H, D, a straight chain alkyl or alkoxy group having 1 to 40 carbon atoms, a branched or cyclic alkyl or alkoxy group having 3 to 40 carbon atoms, a straight-chain alkenyl or alkynyl group having 2 to 40 carbon atoms, a branched alkenyl group or alkynyl group having 3 to 40 carbon atoms, an aromatic or heteroaromatic ring system having 5 to 40 aromatic ring atoms, wherein in each of the above-mentioned groups one or more H atoms may each be replaced by D, F, Cl, Br, or I, and where two or more adjacent substituents $R^a$ here may optionally form a mono- or polycyclic, aliphatic ring system with one another;

L is a divalent group selected from a straight-chain alkylene group having 1 to 40 carbon atoms, a branched or cyclic alkylene group having 3 to 40 carbon atoms, a straight-chain alkenylene or alkynylene group having 2 to 40 carbon atoms, or a branched alkenylene group or alkynylene group having 3 to 40 carbon atoms, each of which each may be substituted by one or more groups $R^a$, where in each case one or more $CH_2$ groups may each be replaced by an arylene group or heteroarylene group having 5 to 40 aromatic ring atoms, Si$(R^a)_2$, Ge$(R^a)_2$, Sn$(R^a)_2$, C═O, C═S, C═Se, C═N$R^a$, P(═O)($R^a$), SO, $SO_2$, —O—, N$R^a$, —C(═O)O—, or —C(═O)N$R^a$—, and where one or more H atoms may each be replaced by D, F, Cl, Br, I, CN, or $NO_2$; an aromatic or heteroaromatic ring system having 5 to 40 aromatic ring atoms, an aralkylene group, a heteroaralkylene group, an alkylarylene group or an alkylheteroarylene group, each of which may be substituted by one or more groups $R^a$, and where in each case one or more H atoms may each be replaced by D, F, Cl, Br, I, CN, or $NO_2$; or a group represented by the following chemical formula (II)

(II)

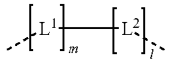

wherein m is an integer of 1 to 50;

l is an integer of 1 to 25;

$L^1$ is

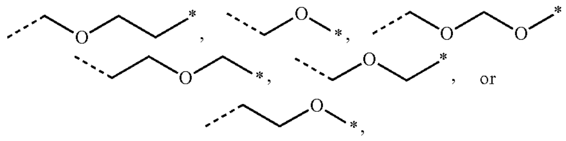

$L^2$ is

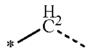

or

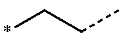

wherein a dashed line indicates a bond to the remainder of the compound and the symbol "*" marks the bond between groups $L^1$ and $L^2$, and wherein each of $L^1$ and $L^2$ may be substituted by one or more groups $R^a$, where one or more $CH_2$ groups of $L^1$ and $L^2$ may each be replaced by —$R^aC$═$CR^a$—, —C≡C—, $Si(R^a)_2$, $Ge(R^a)_2$, $Sn(R^a)_2$, C═O, C═S, C═Se, C═$NR^a$, P(═O)($R^a$), SO, $SO_2$, $NR^a$, or —C(═O)$NR^a$—, and where one or more H atoms in $L^1$ and $L^2$ may each be replaced by D, F, Cl, Br, I, CN, or $NO_2$;

$A^3$ is a divalent group selected from a straight-chain alkylene group having 1 to 40 carbon atoms, a branched or cyclic alkylene group having 3 to 40 carbon atoms, each of which may be substituted by one or more groups $R^a$, where in each case one or more $CH_2$ groups may each be replaced by, $Si(R^a)_2$, $Ge(R^a)_2$, $Sn(R^a)_2$, C═O, C═S, C═Se, C═$NR^a$, P(═O)($R^a$), SO, $SO_2$, —O—, $NR^a$, —C(═O)O—, or —C(═O)$NR^a$—, and where one or more H atoms may each be replaced by D, F, Cl, Br, I, CN, or $NO_2$; an aromatic or heteroaromatic ring system having 5 to 25 aromatic ring atoms, each of which may be substituted by one or more groups $R^a$, and where one or more H atoms of the aromatic or heteroaromatic ring system may each be replaced by D, F, Cl, Br, I, CN, or $NO_2$; and $M^1$ denotes a hydrogen atom; and Z is NH or O;

and at least one further functional material selected from the group consisting of organic light emitting materials, inorganic light emitting materials, charge transporting materials, host or matrix materials, optically transparent polymers, anti-oxidants or stabilizers, radical quenchers, photo initiators or polymerization initiators, wetting and dispersing agents, scattering particles, reflective index adjusting materials, developer-dissolution promoters, scum removers, adhesion enhancers, polymerization inhibitors, defoaming agents, surfactants and sensitizers.

8. The composition according to claim 7, wherein the at least one further functional material is a host or matrix material, selected from (meth)acrylate monomers or polymers.

9. A formulation comprising a nanoparticle according to claim 1 and at least one solvent selected from the group consisting of esters, ketones, glycols, ethers, and aromatic, halogenated and aliphatic hydrocarbons.

10. An optical medium comprising a nanoparticle according to claim 1.

11. An optical device comprising a nanoparticle according to claim 1.

12. A process for the preparation of an optical device according to claim 11, comprising:

a) preparing a mixture by mixing a semiconducting light emitting nanoparticle having at least a core and optionally one or more shell layers, at least one further functional material, a compound (I') defined below and, optionally, at least one solvent;

b) providing the mixture onto a substrate; and c) subjecting the mixture obtained to a photo irradiation having a peak light wavelength in the range from 300 to 650 nm;

wherein the compound (I') represents:

(i) a compound of the following chemical formula (III):

(III)

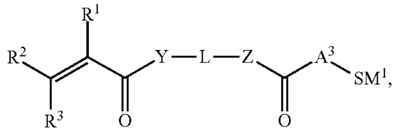

(ii) a compound of the following chemical formulae (IV), (V-a) or (V-b):

(IV)

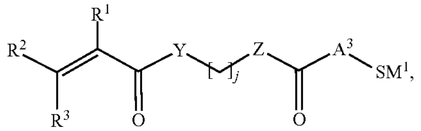

(V-a)

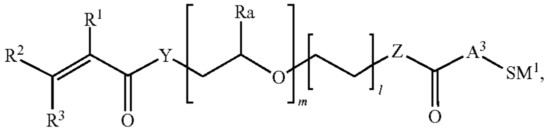

(V-b)

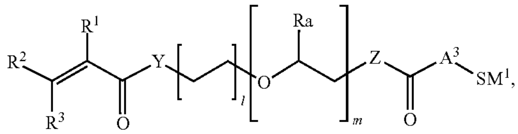

(iii) a compound of one of the following chemical formulae (IV-1) to (IV-6) and (V-1) to (V-6):

(IV-1)

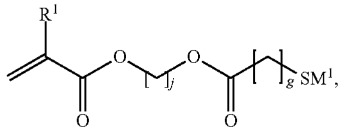

(IV-2)

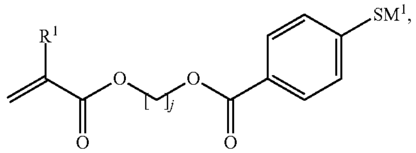

-continued (IV-3)

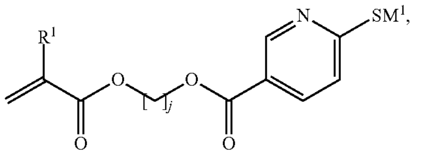

(IV-4)

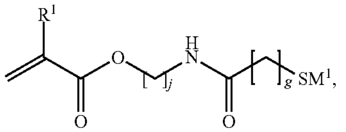

(IV-5)

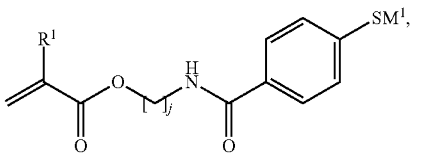

(IV-6)

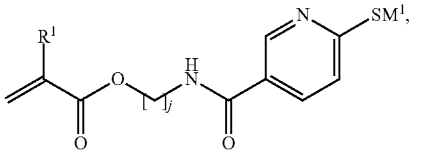

(V-1)

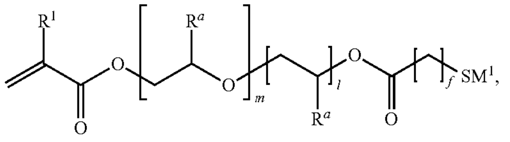

(V-2)

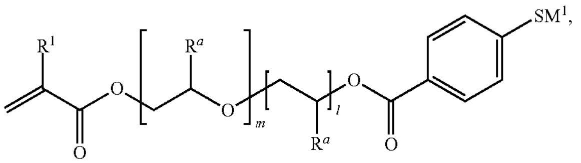

(V-3)

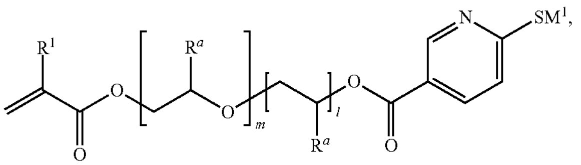

(V-4)

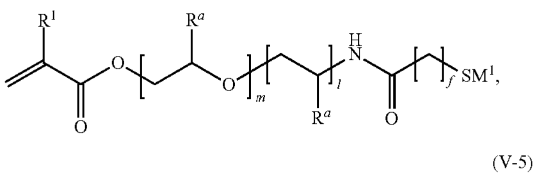

(V-5)

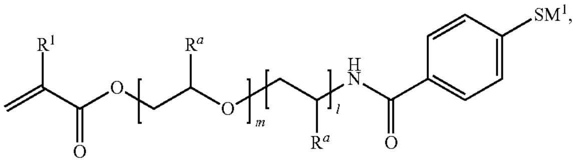

-continued (V-6)

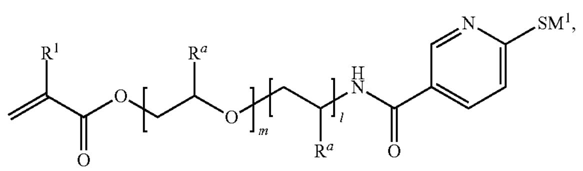

wherein $R^1$ is H, D, CN, a straight chain alkyl or alkoxy group having 1 to 40 carbon atoms, a branched or cyclic alkyl or alkoxy group having 3 to 40 carbon atoms, each of which may be substituted by one or more groups $R^a$, where in each case one or more $CH_2$ groups may each be replaced by $—R^aC{=}CR^a—$, —C≡C—, $Si(R^a)_2$, $Ge(R^a)_2$, $Sn(R^a)_2$, C═O, C═S, C═Se, $C{=}NR^a$, $P({=}O)(R^a)$, SO, $SO_2$, —O—, $NR^a$, —C(═O)O—, or $—C({=}O)NR^a—$, and where one or more H atoms may be replaced by D, F, Cl, Br, I, CN or $NO_2$; an aromatic ring system or a heteroaromatic ring system having 5 to 40 aromatic ring atoms, each of which may be substituted by one or more groups $R^a$, and where one or more H atoms may each be replaced by D, F, Cl, Br, I, CN or $NO_2$;

$R^2$, $R^3$ are, independently of each other, H, D, CN, a straight chain alkyl or alkoxy group having 1 to 40 carbon atoms, a branched or cyclic alkyl or alkoxy group having 3 to 40 carbon atoms, each of which may be substituted by one or more groups $R^a$, where in each case one or more $CH_2$ groups may each be replaced by $—R^aC{=}CR^a—$, —C≡C—, $Si(R^a)_2$, $Ge(R^a)_2$, $Sn(R^a)_2$, C═O, C═S, C═Se, $C{=}NR^a$, $P({=}O)(R^a)$, SO, $SO_2$, —O—, $NR^a$, —C(═O)O—, or $—C({=}O)NR^a—$, and where one or more H atoms may each be replaced by D, F, Cl, Br, I, CN, or $NO_2$; or an aromatic ring system or a heteroaromatic ring system having 5 to 40 aromatic ring atoms, each of which may be substituted by one or more groups $R^a$, and where one or more H atoms may each be replaced by D, F, Cl, Br, I, CN, or $NO_2$;

Y is O, NH, or S;

$R^a$ is at each occurrence, identically or differently, H, D, a straight chain alkyl or alkoxy group having 1 to 40 carbon atoms, a branched or cyclic alkyl or alkoxy group having 3 to 40 carbon atoms, a straight-chain alkenyl or alkynyl group having 2 to 40 carbon atoms, a branched alkenyl group or alkynyl group having 3 to 40 carbon atoms, an aromatic or heteroaromatic ring system having 5 to 40 aromatic ring atoms, wherein in each of the above-mentioned groups one or more H atoms may each be replaced by D, F, Cl, Br, I, and where two or more adjacent substituents $R^a$ here may optionally form a mono- or polycyclic, aliphatic ring system with one another;

L is a divalent group selected from a straight-chain alkylene group having 1 to 40 carbon atoms, a branched or cyclic alkylene group having 3 to 40 carbon atoms, a straight-chain alkenylene or alkynylene group having 2 to 40 carbon atoms, or a branched alkenylene group or alkynylene group having 3 to 40 carbon atoms, each of which each may be substituted by one or more groups $R^a$, where in each case one or more $CH_2$ groups may each be replaced by an arylene group or heteroarylene group having 5 to 40 aromatic ring atoms, $Si(R^a)_2$, $Ge(R^a)_2$, $Sn(R^a)_2$, C═O, C═S, C═Se, C═NR$^a$, P(═O)(R$^a$), SO, SO$_2$, —O—, NR$^a$, —C(═O)O—, or —C(═O)NR$^a$—, and where one or more H atoms may each be replaced by D, F, Cl, Br, I, CN or NO$_2$; an aromatic or heteroaromatic ring system having 5 to 40 aromatic ring atoms, an aralkylene group, a heteroaralkylene group, an alkylarylene group or an alkylheteroarylene group, each of which may be substituted by one or more groups R$^a$, and where in each case one or more H atoms may each be replaced by D, F, Cl, Br, I, CN, NO$_2$; or a group represented by the following chemical formula (II):

(II)

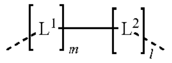

wherein m is an integer of 1 to 50;

l is an integer of 1 to 25;

L$^1$ is

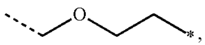,
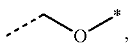,
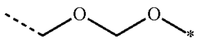
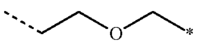,
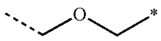, or
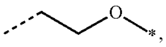,

L$^2$ is

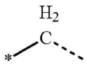 or 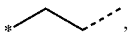, wherein a dashed line indicates a bond to the remainder of the compound and the symbol "*" marks the bond between groups L$^1$ and L$^2$, and wherein each of L$^1$ and L$^2$ may be substituted by one or more groups R$^a$, where one or more CH$_2$ groups of L$^1$ and L$^2$ may each be replaced by —R$^a$C═CR$^a$—, —C≡C—, Si(R$^a$)$_2$, Ge(R$^a$)$_2$, Sn(R$^a$)$_2$, C═O, C═S, C═Se, C═NR$^a$, P(═O)(R$^a$), SO, SO$_2$, NR$^a$, or —C(═O)NR$^a$—, and where one or more H atoms in L$^1$ and L$^2$ may each be replaced by D, F, Cl, Br, I, CN or NO$_2$;

A$^3$ is a divalent group selected from a straight-chain alkylene group having 1 to 40 carbon atoms, a branched or cyclic alkylene group having 3 to 40 carbon atoms, each of which may be substituted by one or more groups R$^a$, where in each case one or more CH$_2$ groups may each be replaced by, Si(R$^a$)$_2$, Ge(R$^a$)$_2$, Sn(R$^a$)$_2$, C═O, C═S, C═Se, C═NR$^a$, P(═O)(R$^a$), SO, SO$_2$, —O—, NR$^a$, —C(═O)O—, or —C(═O)NR$^a$—, and where one or more H atoms may each be replaced by D, F, Cl, Br, I, CN, or NO$_2$; an aromatic or heteroaromatic ring system having 5 to 25 aromatic ring atoms, each of which may be substituted by one or more groups R$^a$, and where one or more H atoms of the aromatic or heteroaromatic ring system may each be replaced by D, F, Cl, Br, I, CN, or NO$_2$;

M$^1$ denotes a hydrogen atom, or a metal cation selected from ½ Mg$^{2+}$, ½ Cu$^{2+}$, ½ Zn$^{2+}$, ½ Pb$^{2+}$, ½ Sn$^{2+}$, ½ Cd$^{2+}$, ⅓ Bi$^{3+}$ or ¼ Sn$^{4+}$;

Z is NH or O;

j is an integer of 1 to 40; and indices g and f are identically or differently an integer of 1 to 40.

* * * * *